United States Patent
Yancey et al.

(10) Patent No.: US 11,083,551 B2
(45) Date of Patent: Aug. 10, 2021

(54) SCANNING DEVICE

(71) Applicant: SDC U.S. SmilePay SPV, Nashville, TN (US)

(72) Inventors: Christopher Yancey, Nashville, TN (US); Jordan Katzman, Nashville, TN (US)

(73) Assignee: SDC U.S. SmilePay SPV, Nashville, TN (US)

( * ) Notice: Subject to any disclaimer, the term of this patent is extended or adjusted under 35 U.S.C. 154(b) by 0 days.

(21) Appl. No.: 17/106,635

(22) Filed: Nov. 30, 2020

(65) Prior Publication Data

US 2021/0077233 A1    Mar. 18, 2021

Related U.S. Application Data

(63) Continuation of application No. 16/711,173, filed on Dec. 11, 2019, now Pat. No. 10,849,723.

(60) Provisional application No. 62/844,694, filed on May 7, 2019.

(51) Int. Cl.
*A61C 13/00*    (2006.01)
*G06T 7/00*    (2017.01)
*A61C 7/00*    (2006.01)

(52) U.S. Cl.
CPC .......... *A61C 13/0004* (2013.01); *A61C 7/002* (2013.01); *G06T 7/0012* (2013.01); *G06T 2207/30036* (2013.01)

(58) Field of Classification Search
None
See application file for complete search history.

(56) References Cited

U.S. PATENT DOCUMENTS

| | | | |
|---|---|---|---|
| 6,386,867 B1 | 5/2002 | Durbin et al. |
| 6,532,299 B1 | 3/2003 | Sachdeva et al. |
| 6,632,089 B2 | 10/2003 | Rubbert et al. |
| 6,648,640 B2 | 11/2003 | Rubbert et al. |
| 6,695,613 B2 | 2/2004 | Taub et al. |
| 6,697,164 B1 | 2/2004 | Babayoff et al. |
| 6,788,986 B1 | 9/2004 | Traber et al. |
| 6,845,175 B2 | 1/2005 | Kopelman et al. |
| 6,879,712 B2 | 4/2005 | Tuncay et al. |
| 6,940,611 B2 | 9/2005 | Babayoff et al. |
| 7,029,275 B2 | 4/2006 | Rubbert et al. |
| 7,068,825 B2 | 6/2006 | Rubbert et al. |
| 7,092,107 B2 | 8/2006 | Babayoff et al. |
| 7,092,780 B2 | 8/2006 | Ganley et al. |
| 7,156,655 B2 | 1/2007 | Sachdeva et al. |
| 7,230,725 B2 | 6/2007 | Babayoff et al. |

(Continued)

OTHER PUBLICATIONS

US 9,420,939 B1, 08/2016, Kopelman et al. (withdrawn)

(Continued)

*Primary Examiner* — Carlos R Ortiz Rodriguez
(74) *Attorney, Agent, or Firm* — Foley & Lardner LLP

(57) ABSTRACT

A system comprising a scanning device is operable by a user to scan teeth of the user to acquire images of the teeth. The scanning device comprises a camera operable to acquire the images, a guide configured to orient the camera with respect to the teeth to facilitate acquisition of the images, and a server system configured to receive the images acquired by the scanning device and to develop a treatment plan for the user based on the received images.

29 Claims, 39 Drawing Sheets

(56) References Cited

U.S. PATENT DOCUMENTS

| | | |
|---|---|---|
| 7,255,558 B2 | 8/2007 | Babayoff et al. |
| 7,286,954 B2 | 10/2007 | Kopelman et al. |
| 7,312,924 B2 | 12/2007 | Trissel |
| 7,319,529 B2 | 1/2008 | Babayoff |
| 7,328,077 B2 | 2/2008 | Durbin et al. |
| 7,442,041 B2 | 10/2008 | Imgrund et al. |
| 7,471,821 B2 | 12/2008 | Rubbert et al. |
| 7,477,402 B2 | 1/2009 | Babayoff et al. |
| 7,494,338 B2 | 2/2009 | Durbin et al. |
| 7,511,829 B2 | 3/2009 | Babayoff |
| 7,625,335 B2 | 12/2009 | Deichmann et al. |
| 7,695,281 B2 | 4/2010 | Burger et al. |
| 7,717,708 B2 | 5/2010 | Sachdeva et al. |
| 7,724,378 B2 | 5/2010 | Babayoff |
| 7,740,476 B2 | 6/2010 | Rubbert et al. |
| 7,890,290 B2 | 2/2011 | Kopelman et al. |
| 7,946,846 B2 | 5/2011 | Babayoff et al. |
| 7,956,862 B2 | 6/2011 | Zhang et al. |
| 7,965,860 B2 | 6/2011 | Holzner et al. |
| 8,102,538 B2 | 1/2012 | Babayoff |
| 8,206,152 B2 | 6/2012 | Holzner et al. |
| 8,255,071 B2 | 8/2012 | Kaigler, Sr. |
| 8,353,703 B2 | 1/2013 | Amber et al. |
| 8,363,228 B2 | 1/2013 | Babayoff |
| 8,451,456 B2 | 5/2013 | Babayoff |
| 8,454,365 B2 * | 6/2013 | Boerjes .................. A61C 11/08 433/223 |
| 8,487,962 B2 | 7/2013 | Quadling et al. |
| 8,520,925 B2 | 8/2013 | Duret |
| 8,532,355 B2 | 9/2013 | Quadling et al. |
| 8,582,870 B2 | 11/2013 | Glor et al. |
| 8,675,207 B2 | 3/2014 | Babayoff |
| 8,706,672 B2 | 4/2014 | Malfliet et al. |
| 8,837,026 B2 | 9/2014 | Fisker et al. |
| 8,932,058 B2 | 1/2015 | Fisker et al. |
| 8,948,482 B2 | 2/2015 | Levin |
| 8,992,215 B2 | 3/2015 | Chapoulaud et al. |
| 8,994,717 B2 | 3/2015 | Holzner et al. |
| 8,998,608 B2 | 4/2015 | Imgrund et al. |
| 9,050,158 B2 | 6/2015 | Nowak et al. |
| 9,138,299 B2 | 9/2015 | Van Lierde et al. |
| 9,180,624 B2 | 11/2015 | Fisker et al. |
| 9,192,305 B2 | 11/2015 | Levin |
| 9,214,014 B2 | 12/2015 | Levin |
| 9,308,055 B2 | 4/2016 | Fisker et al. |
| 9,336,336 B2 | 5/2016 | Deichmann et al. |
| 9,390,063 B2 | 7/2016 | Hultgren et al. |
| 9,393,087 B2 | 7/2016 | Moalem |
| 9,412,166 B2 | 8/2016 | Getto et al. |
| 9,431,887 B2 | 8/2016 | Boltanski |
| 9,439,568 B2 | 9/2016 | Atiya et al. |
| 9,451,873 B1 | 9/2016 | Kopelman et al. |
| 9,491,863 B2 | 11/2016 | Boltanski |
| 9,510,757 B2 | 12/2016 | Kopelman et al. |
| 9,529,970 B2 | 12/2016 | Andreiko |
| 9,566,138 B2 | 2/2017 | Fisker |
| 9,589,329 B2 | 3/2017 | Levin |
| 9,642,685 B2 | 5/2017 | Brodkin |
| 9,660,418 B2 | 5/2017 | Atiya et al. |
| 9,668,829 B2 | 6/2017 | Kopelman |
| 9,671,220 B2 | 6/2017 | Gandyra et al. |
| 9,672,444 B2 | 6/2017 | Mehl |
| 9,683,835 B2 | 6/2017 | Kopelman et al. |
| 9,687,324 B2 | 6/2017 | Fisker et al. |
| 9,693,839 B2 | 7/2017 | Atiya et al. |
| 9,694,539 B2 | 7/2017 | Van Lierde et al. |
| 9,709,803 B2 | 7/2017 | Boltanski |
| 9,717,402 B2 | 8/2017 | Lampert et al. |
| 9,724,177 B2 | 8/2017 | Levin |
| 9,767,223 B2 | 9/2017 | Fisker et al. |
| 9,801,698 B2 | 10/2017 | Levin |
| 9,805,167 B2 | 10/2017 | Van Lierde et al. |
| 9,830,688 B2 | 11/2017 | Levin |
| 9,833,301 B2 | 12/2017 | Fisker et al. |
| 9,844,419 B2 | 12/2017 | Andreiko |
| 9,861,457 B2 | 1/2018 | Fisker et al. |
| 9,872,745 B2 | 1/2018 | Fisker et al. |
| 9,934,360 B2 | 4/2018 | Lajoie et al. |
| 9,937,020 B2 | 4/2018 | Choi |
| 9,937,021 B2 | 4/2018 | Babayoff et al. |
| 9,978,172 B2 | 5/2018 | Adamson et al. |
| 9,987,108 B2 | 6/2018 | Levin |
| 10,004,572 B2 | 6/2018 | Kopelman et al. |
| 10,022,916 B2 | 7/2018 | Powell et al. |
| 10,058,404 B2 | 8/2018 | Atiya et al. |
| 10,064,553 B2 | 9/2018 | Fisker et al. |
| 10,098,521 B2 | 10/2018 | Clausen et al. |
| 10,098,714 B2 | 10/2018 | Kuo |
| 10,104,363 B2 | 10/2018 | Fisker et al. |
| 10,105,196 B2 | 10/2018 | Fisker |
| 10,105,199 B2 | 10/2018 | Boltanski |
| 10,108,269 B2 | 10/2018 | Sabina et al. |
| 10,111,581 B2 | 10/2018 | Makmel |
| 10,111,714 B2 | 10/2018 | Kopelman et al. |
| 10,117,581 B2 | 11/2018 | Kopelman et al. |
| 10,123,706 B2 | 11/2018 | Elbaz et al. |
| 10,136,972 B2 | 11/2018 | Sabina et al. |
| 10,148,066 B2 | 12/2018 | Atiya et al. |
| 10,159,546 B2 | 12/2018 | Kopelman et al. |
| 10,179,034 B2 | 1/2019 | Schiemann |
| 10,188,490 B2 | 1/2019 | Kopelman |
| 10,213,275 B2 | 2/2019 | Groscurth et al. |
| 10,219,875 B1 | 3/2019 | Kopelman et al. |
| 10,238,296 B2 | 3/2019 | Van Der Poel et al. |
| 10,242,128 B2 | 3/2019 | Fisker et al. |
| 10,258,437 B2 | 4/2019 | Atiya et al. |
| 10,258,439 B1 | 4/2019 | Kitching et al. |
| 10,275,862 B2 | 4/2019 | Levin |
| 10,288,875 B2 | 5/2019 | Boltanski |
| 10,299,865 B2 | 5/2019 | Deichmann et al. |
| 10,311,162 B2 | 6/2019 | Fisker |
| 10,327,873 B2 | 6/2019 | Fisker |
| 10,380,212 B2 | 8/2019 | Elbaz et al. |
| 10,426,328 B2 | 10/2019 | Lampert et al. |
| 10,453,269 B2 | 10/2019 | Furst |
| 10,456,043 B2 | 10/2019 | Atiya et al. |
| 10,470,846 B2 | 11/2019 | Kopelman et al. |
| 10,485,415 B2 | 11/2019 | Lampert et al. |
| 10,485,639 B2 | 11/2019 | Levin |
| 2007/0203663 A1 | 8/2007 | Kopelman et al. |
| 2009/0298017 A1 | 12/2009 | Boerjes et al. |
| 2010/0239136 A1 | 9/2010 | Gandyra et al. |
| 2014/0272765 A1 | 9/2014 | Andreiko et al. |
| 2015/0150660 A1 | 6/2015 | Fisker et al. |
| 2016/0000332 A1 | 1/2016 | Atiya et al. |
| 2016/0008111 A1 | 1/2016 | Jumpertz |
| 2016/0217708 A1 | 7/2016 | Levin et al. |
| 2016/0224690 A1 | 8/2016 | Lee et al. |
| 2016/0256240 A1 | 9/2016 | Shivapuja et al. |
| 2016/0295191 A1 | 10/2016 | Babayoff |
| 2016/0324605 A1 | 11/2016 | Fisker et al. |
| 2017/0319293 A1 | 11/2017 | Fisker |
| 2018/0028065 A1 | 2/2018 | Elbaz et al. |
| 2018/0125610 A1 | 5/2018 | Carrier et al. |
| 2018/0153409 A1 | 6/2018 | Kopelman et al. |
| 2018/0168780 A1 | 6/2018 | Kopelman et al. |
| 2018/0168781 A1 | 6/2018 | Kopelman et al. |
| 2018/0192964 A1 | 7/2018 | Stalder et al. |
| 2018/0206949 A1 | 7/2018 | Jordan |
| 2018/0280124 A1 | 10/2018 | Babayoff et al. |
| 2018/0338820 A1 | 11/2018 | Boltanski |
| 2018/0353062 A1 | 12/2018 | Makmel |
| 2018/0360411 A1 | 12/2018 | Abkai |
| 2018/0367786 A1 | 12/2018 | Furst et al. |
| 2019/0008617 A1 | 1/2019 | Kopelman et al. |
| 2019/0011996 A1 | 1/2019 | Sabina et al. |
| 2019/0015179 A1 | 1/2019 | Kuo |
| 2019/0029524 A1 | 1/2019 | Kopelman et al. |
| 2019/0043190 A1 | 2/2019 | Sabina et al. |
| 2019/0060042 A1 | 2/2019 | Fisker et al. |
| 2019/0076026 A1 | 3/2019 | Elbaz et al. |
| 2019/0095539 A1 | 3/2019 | Elbaz et al. |
| 2019/0107932 A1 | 4/2019 | Wen et al. |
| 2019/0117349 A1 | 4/2019 | Fisker et al. |

(56) References Cited

U.S. PATENT DOCUMENTS

2019/0133429 A1    5/2019    Dillon et al.
2019/0133726 A1    5/2019    Holmstrom et al.
2019/0142257 A1    5/2019    Vinther et al.

OTHER PUBLICATIONS

Dental Monitoring, "A Scanbox Demo", May 5, 2019, https://www.youtube.com/watch?v=MsCfv2PDQ0o, 37 pages of screenshots.
International Search Report and Written Opinion for PCT/US2020/031720, dated Aug. 6, 2020, 11 pages.
Moylan et al., "Accuracy of a smartphone-based orthodontic treatment-monitoring application: A pilot study," The EH Angle Education and Research Foundation, In., Mar. 19, 2019, https://dental-monitoring.com/wp-content/uploads/2019/05/100218-710.1-1.pdf, 7 pages.
Smiletronix Technologies LTD, Smiletronix homepage: https://www.smiletronix.com/, 2019, 11 pages of screenshots.

* cited by examiner

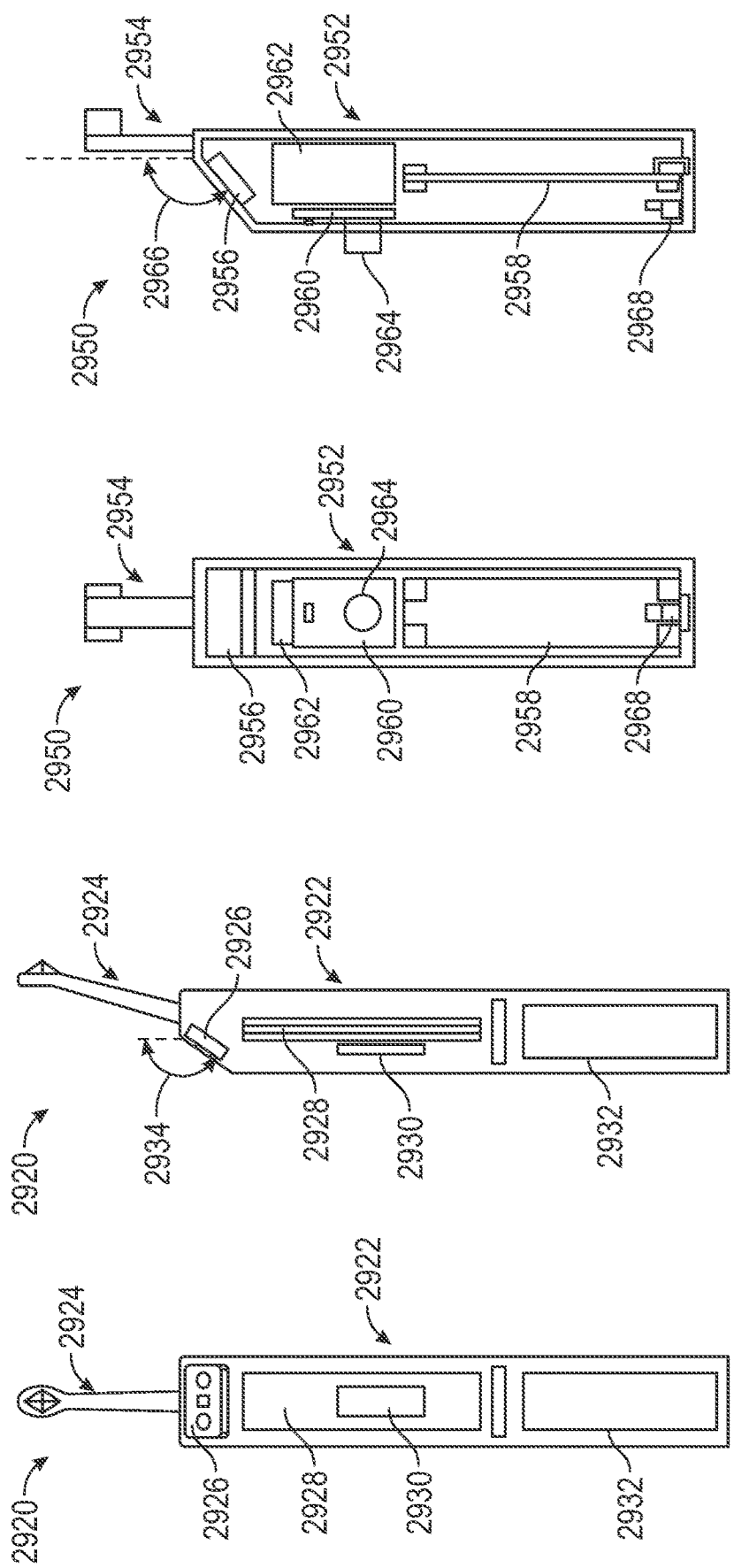

SCANNING DEVICE

CROSS-REFERENCE TO RELATED APPLICATIONS

This application is a continuation of U.S. patent application Ser. No. 16/711,173, filed Dec. 11, 2019, which claims the benefit of and priority to U.S. Provisional Application No. 62/844,694, filed May 7, 2019, which are each hereby incorporated by reference in their entirety.

BACKGROUND

Dental aligners are plastic trays custom made to fit tightly over the teeth of a user to force the teeth to move to a desired location. Creating a three-dimensional model of teeth is useful in creating dental aligners. Conventional ways to create a three-dimensional model of teeth include making a physical impression of the teeth or taking an intraoral scan of the teeth.

To make a physical impression of teeth, a patient must either go to the office of an orthodontic professional to take the impression or use an at-home dental impression kit. To scan teeth intraorally, the orthodontic professional inserts a scanning device into the mouth of the patient such that images of the teeth can be captured from inside the mouth. Scanning teeth in the office of an orthodontic or dental professional is inconvenient (e.g., the user must travel to the office), costly (e.g., the user must pay the professional for the service), and limiting (e.g., if a scan is incomplete or corrupted, the user must take time to travel back to the office for an additional scan). Using an at-home dental impression kit can be difficult for a user to execute properly, which can result in the need for repeat impressions.

A scanning device for a user to accurately scan the user's own teeth without requiring a visit to a dental or orthodontic professional is desirable to avoid the complications associated with physical impressions and scanning in a professional setting.

SUMMARY

An embodiment relates to a system comprising a scanning device operable by a user to scan teeth of the user to acquire images of the teeth. The scanning device comprises a camera operable to acquire the images, a guide configured to orient the camera with respect to the teeth to facilitate acquisition of the images, and a server system configured to receive the images acquired by the scanning device and to develop a treatment plan for the user based on the received images.

Another embodiment relates to a scanning device comprising a body configured to be held by a user to scan teeth of the user to acquire images of the teeth. The scanning device also includes a camera operable to acquire the images and a guide configured to orient the camera with respect to the teeth to facilitate acquisition of the images. The scanning device also includes a communications circuit configured to communicate the images to a server system for development of a treatment plan for the user.

Another embodiment relates to a method comprising providing a scanning device to a user that is operable by the user to scan teeth of the user. The scanning device comprises a camera coupled to a body of the scanning device, the camera configured to acquire images of the teeth of the user. A guide is coupled to the body, the guide configured to contact a guide set of teeth and maintain the camera at a substantially constant distance from a tooth being scanned in a scanning set of teeth in the mouth of the user. The method further comprises communicating the images from the scanning device to a mobile device of the user, communicating the images from the mobile device of the user to a server system, generating an orthodontic treatment plan based on the images communicated to the server system, and manufacturing one or more aligners based on the orthodontic treatment plan.

BRIEF DESCRIPTION OF THE DRAWINGS

FIGS. 29A-B are illustrations of a front and a side view, respectively, of an arrangement of internal components in a scanning device, according to some embodiments.

FIGS. 30A-B are illustrations of a front and a side view, respectively, of another arrangement of internal components in another scanning device, according to some embodiments.

DETAILED DESCRIPTION

Figure 1A:
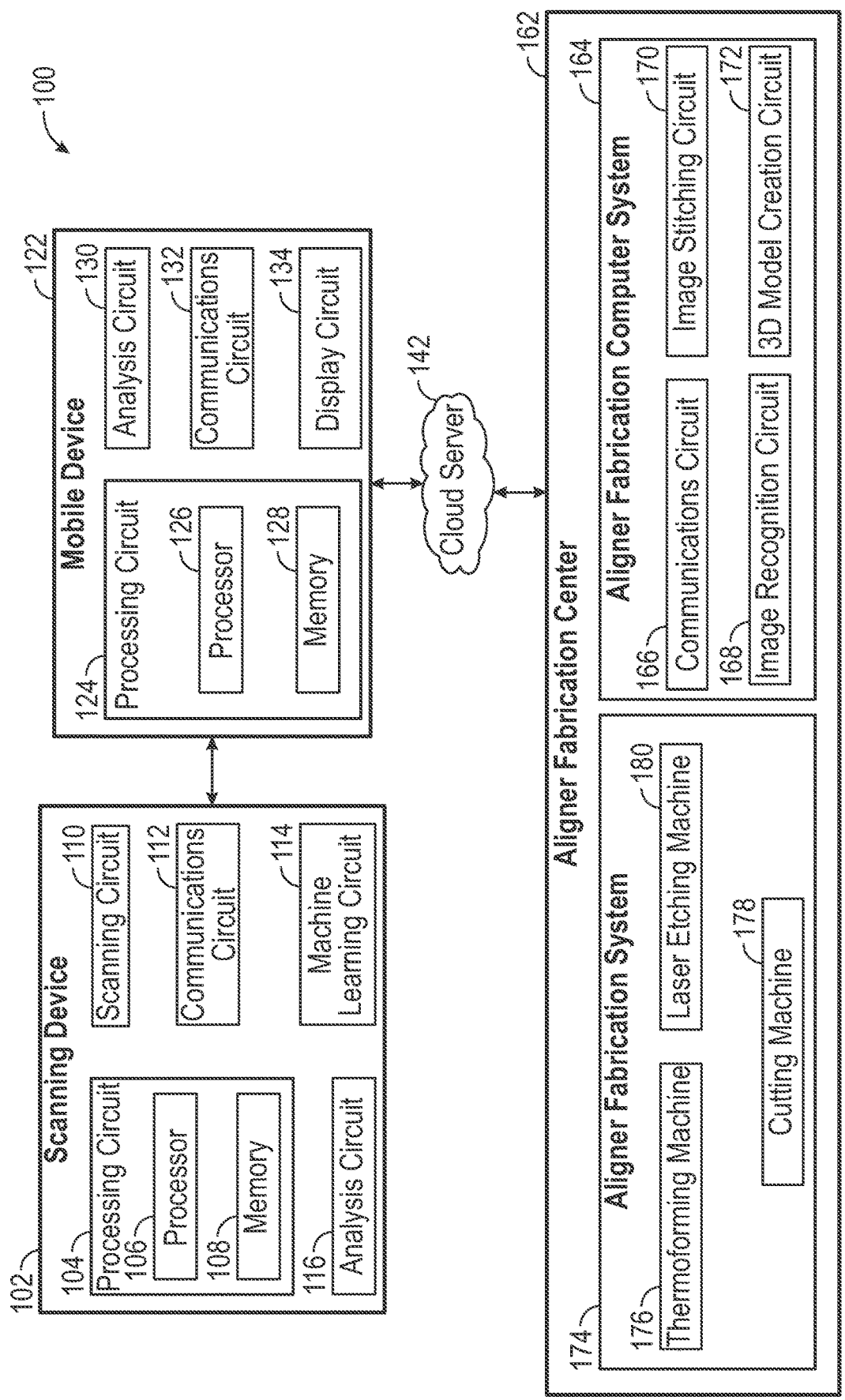
FIG. 1A is a block diagram of a system for extraoral scanning of teeth, according to some embodiments.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

For a patient to begin a treatment plan using dental aligners, it is beneficial to create a three-dimensional ("3D") model of the teeth of the patient. As described, the 3-D model can be generated using conventional impression techniques or a scanning device. However, a patient may need to visit an orthodontic professional to have the impressions taken or teeth scanned with the scanning device. In some instances, a patient may need to visit a different location where a scan is conducted by a professional that has been trained in the scanning process (e.g., a professional that is not a dental or orthodontic professional). In another example, a professional trained in the scanning process may bring a scanner to the patient to conduct a scan. A conventional scanner is generally large and can require significant structural support (e.g., attachment to a vehicle or a rolling cart, etc.). In either instance, the scan must be scheduled such that a professional trained in use of a scanner (e.g., a dental or orthodontic professional, an individual with specific training, etc.) can conduct the scan of the patient. A patient may therefore be more interested in scanning teeth with a portable device (e.g., a device that does not require structural support, and is significantly lighter than a conventional device such that the entire device can be held in the hand of the patient) that can be operated by the user (e.g., without assistance and/or direction from a trained professional) to scan teeth. Such a device provides the patient the ability to scan the patient's teeth as the patient desires. For instance, after conducting an initial scan, the patient may desire to conduct a subsequent scan. With a conventional scanner, the patient would have to schedule another scan and then wait until the scheduled date and time to conduct the scan. With a portable device, the patient can conduct subsequent scans as often as the patient desires.

As used herein, the term "extraoral scan" refers to a scan of the teeth of a patient where the lens of the scanner does not enter the mouth of the patient. As used herein, the term "intraoral scan" refers to scanning the teeth by inserting a lens of a scanning device (e.g., a camera, a 3-D scanner, or any other scanning device that is capable of capturing images of the teeth) into the mouth to capture images of the teeth. As used herein, the terms "user" and "patient" may be used interchangeably such that the user may be the patient and the patient may be the user. As used herein, the term "dental aligner" is intended to cover any type of dental appliance and can refer to any orthodontic device or device intended for use in a patient's mouth, including but not limited to dental aligners for repositioning one or more teeth of the patient, a denture, a mouth guard, or a retainer.

Referring to FIG. 1A, a block diagram of a system 100 for scanning teeth (e.g., intraorally or extraorally) is shown, according to some embodiments. The system 100 includes a scanning device 102, a mobile device 122, a cloud server 142, and an aligner fabrication center 162.

The scanning device 102 can be any device configured to scan a 3D surface. Examples of the scanning device 102 include, but are not limited to, non-contact active 3D scanners (e.g., time-of-flight, triangulation, conoscopic holography, or any other kind of non-contact active 3D scanner), hand held laser 3D scanners, structured light 3D scanners, modulated light 3D scanners, and non-contact passive 3D scanners (e.g., stereoscopic, photometric, silhouette, or any other kind of non-contact passive 3D scanner).

The scanning device 102 includes a processing circuit 104, a scanning circuit 110, a communications circuit 112, a machine learning circuit 114, and an analysis circuit 116. The processing circuit 104 is further shown to include a processor 106 and a memory 108. The processor 106 can be any type of processor capable of performing the functions described herein. The processor 106 may be a single or multi-core processor(s), digital signal processor, microcontroller, or other processor or processing/controlling circuit. Similarly, the memory 108 can be any type of volatile or non-volatile memory or data storage capable of performing the functions described herein. In operation, the memory 108 may store various data and software used during operation of the scanning device 102, such as operating systems, applications, programs, libraries, and drivers. The memory 108 is communicatively coupled to the processor 106 such that the processor 106 can execute files located in the memory 108.

The scanning circuit 110 is communicably coupled to the processor 106 and is configured to conduct a scan of one or more objects. In this regard, the scanning circuit 110 gathers images of the object(s) being scanned (e.g., the size, shape, color, depth, tracking distance, and other physical characteristics) such that the data can be provided to other circuits in the scanning device 102 (e.g., the analysis circuit 116 and the machine learning circuit 114). To appropriately scan the target objects, the scanning circuit 110 can include a wide variety of sensors including, but not limited to, gyroscopes, accelerometers, magnetometers, inertial measurement units ("IMU"), depth sensors, and color sensors.

The communications circuit 112 is communicably coupled to the scanning circuit 110, the machine learning circuit 114, and the analysis circuit 116 and is configured to send communications to, and receive communications from, the mobile device 122. For example, the communications circuit 112 can communicate information regarding the sufficiency of a scan to the mobile device 122 such that the mobile device 122 can display the information to the patient conducting the scan. As another example, the communications circuit 112 can provide images of the scan to the mobile device 122 in real time for the mobile device 122 to display to the patient during the scan. The communications circuit 112 can communicate with the mobile device 122 in a variety of ways including, but not limited to, Bluetooth, a WiFi network, a wired local area network (LAN), Zigbee, or any other suitable way for devices to exchange information.

The machine learning circuit 114 is configured to receive the images gathered by the scanning circuit 110 during a scan and determine characteristics of the scan. For example, the machine learning circuit 114 can determine, based on the images received, whether the patient initiated a scan from the correct location or whether the patient held the scanning device 102 in the correct orientation during the scan. The machine learning circuit 114 is also communicably coupled to the communications circuit 112 and is further configured to receive updates to improve the capabilities of the machine learning circuit 114.

The analysis circuit 116 is configured to receive information from the scanning circuit 110 and the machine learning circuit 114 and analyze the information. For example, the analysis circuit 116 can receive image data from the scanning circuit 110 and determine a level of confidence that the scan being conducted by the patient will be acceptable. As another example, the analysis circuit 116 can merge multiple scans together such that the acceptable portions of the scans are combined to generate an acceptable scan. The analysis circuit 116 can provide the results of the analysis to the machine learning circuit 114 and the communications circuit 112.

The mobile device 122 can be any type of portable device configured to run a mobile application ("application"). As used herein, the term "application" refers to software that can be loaded on to a piece of hardware (e.g., the mobile device 122), where the software communicates with both the hardware and a server to perform the desired functions. Examples of the mobile device 122 include, but are not limited to, a mobile phone, a tablet computer, a laptop computer, a smart watch, a fitness tracker, and any other Internet-connected device that is capable of running an application. The mobile device 122 can be a personal mobile device 122 of the patient. For example, the mobile device 122 can be the patient's own mobile phone.

The mobile device 122 is shown to include a processing circuit 124, an analysis circuit 130, a communication circuit 132, and a display circuit 134. The processing circuit 124 is further shown to include a processor 126 and a memory 128. The processor 126 can be any type of processor capable of performing the functions described herein. The processor 126 may be a single or multi-core processor(s), digital signal processor, microcontroller, or other processor or processing/controlling circuit. Similarly, the memory 128 can be any type of volatile or non-volatile memory or data storage capable of performing the functions described herein. In operation, the memory 128 may store various data and software used during operation of the mobile device 122, such as operating systems, applications, programs, libraries, and drivers. The memory 128 is communicatively coupled to the processor 126 such that the processor 126 can execute files located in the memory 128.

The communication circuit 132 is communicably coupled to the analysis circuit 130 and the display circuit 134 and is configured to send communications to, and receive communications from, the mobile device 122, and to send communications to, and receive communications from, the cloud server 142. For example, the communication circuit 132 can communicate information regarding images received from the scanning device 102 to the cloud server 142 such that the cloud server 142 can perform further operations. The communication circuit 132 can communicate with the mobile device 122 and the cloud server 142 in a variety of ways including, but not limited to, Bluetooth, a WiFi network, a wired local area network (LAN), Zigbee, or any other suitable way for devices to exchange information. In some embodiments, the communication circuit 132 includes a radiofrequency transceiver to communicate with one or more radio towers to transmit and/or receive information using radio waves. In some embodiments, the radiofrequency transceiver includes a single band transceiver. In some embodiments, the radiofrequency transceiver includes a dual band transceiver.

The analysis circuit 130 is configured to receive information from the communication circuit 132 and analyze the information. For example, the communication circuit 132 can receive confidence level data from the scanning device 102 and provide the data to the analysis circuit 130. The confidence level data can be based on a comparison of the accuracy of the current scan to the accuracy of the scan of an average user. The analysis circuit 130 can determine whether the patient is scanning more or less accurately throughout the scan and can provide the results of the analysis to the display circuit 134 and the cloud server 142. Additionally, the analysis circuit 130 is operable to perform additional operations using the images recorded by the scanning device 102. For example, the analysis circuit 130 can determine the depth of the scan based on the information provided to it by the scanning device 102.

The display circuit 134 is configured to receive information from the scanning device 102 and the analysis circuit 116 and display the information to the patient. For example, the display circuit 134 can receive information regarding the accuracy of the scan being performed. The display circuit 134 can provide the scan accuracy information to the patient by showing the scan accuracy information on the display of the mobile device 122. The accuracy information can be provided as color coded information, where teeth that have been scanned successfully will show as green and teeth that have either been missed or scanned unsuccessfully will show as red. As another example, the display circuit 134 can receive images of the teeth of the patient from the scanning device 102, and the display circuit 134 can display the images of the teeth of the patient on the display of the mobile device 122 in real time as the patient scans the teeth.

The cloud server 142 is communicably coupled to the mobile device 122 and the aligner fabrication center 162. In addition to being communicably coupled to the mobile device 122, the cloud server 142 can be communicably coupled to a plurality of mobile devices, with each of the plurality of mobile devices being communicably coupled to a separate scanning device. The cloud server 142 is configured to receive scan data from the mobile device 122 and perform additional operations on the data in order to prepare the scan data to send to the aligner fabrication center 162. The additional operations the cloud server 142 can perform include, but are not limited to, high-resolution reconstruction of scanned images and converting the scanned images to one or more 3D images. The cloud server 142 can communicate the results of the additional operations to the aligner fabrication center 162.

In addition, the cloud server 142 is configured to analyze the data received from the plurality of mobile devices to which the cloud server 142 is communicably coupled, and provide the output of the analysis to the machine learning circuit 114 via the mobile device 122. For example, the cloud server 142 may determine, based on the analysis of a plurality of scan data from various scans, that patients must hold the scanning device 102 within a certain angular tolerance. The cloud server 142 can provide that information to the machine learning circuit 114 (and the other machine learning circuits associated with the plurality of mobile devices connected to the cloud server 142) such that the scanning device 102 can ensure the patient begins the scan with the scanning device 102 in the proper orientation.

The aligner fabrication center 162 is communicably coupled to the cloud server 142 and is configured to receive the 3D images from the cloud server 142 and generate one or more orthodontic aligners based on the 3D images. The aligner fabrication center 162 is shown to include an aligner fabrication computer system 164 and an aligner fabrication system 174. The aligner fabrication computing system 164 is configured to determine, based on the 3D images, the optimal way to reposition the teeth of the patient from a first configuration to a second configuration. The aligner fabrication computing system 164 includes a communications circuit 166, an image recognition circuit 168, an image stitching circuit 170, and a 3D model creation circuit 172. The aligner fabrication system 174 is configured to create, based on one or more physical 3D models, one or more aligners operable to reposition the teeth of a patient.

The communications circuit 166 is communicably coupled to the cloud server 142 such that the cloud server 142 provides image data to the aligner fabrication computer system 164 via the communications circuit 166. The communications circuit 166 can also communicate information to the cloud server 142 for the cloud server 142 to provide to the machine learning circuit 114 via the mobile device 122. For example, if the images provided to the aligner fabrication computer system 164 were not sufficient to generate viable aligners, the communications circuit 166 notifies the cloud server 142 of the deficiency, the cloud server 142 updates the machine learning circuit 114, and the machine learning circuit 114 prevents similar deficiencies from being accepted in future scans.

The image recognition circuit 168 is operable to receive the image data from the communications circuit 166 and determine the location of the images for further processing. For example, the image recognition circuit can receive four images of the mouth of a patient, and the four images represent the scan of the entire mouth. The image recognition circuit 168 can determine which image represents the lower right quadrant of the mouth, the lower left quadrant of the mouth, the upper right quadrant of the mouth, and the upper left quadrant of the mouth such that the image recognition circuit 168 organizes the images such that the images can be stitched together.

The image stitching circuit 170 receives the recognized images from the image recognition circuit 168 and stitches the images together to create images of the top and bottom teeth. In some embodiments, the image stitching circuit 170 creates one image for the top teeth and one image for the bottom teeth. In some embodiments, the image stitching circuit creates a single image that includes both the top teeth and the bottom teeth. The image stitching circuit 170 can implement any known method of stitching to stitch the images together. For example, the image stitching circuit 170 can stitch the images together using keypoint detection (e.g., finding distinct regions in images used to match images together), registration (e.g., matching features in images that minimize the sum of absolute differences between overlapping pixels), or any other known stitching method. The stitched image is provided to the 3D model creation circuit 172 for further processing.

The 3D model creation circuit 172 receives the stitched image and creates a 3D model from the stitched image. The 3D model creation circuit 172 can use any known method of generating a 3D model including, but not limited to, depth-based conversion, depth from motion, depth from focus, depth from perspective, or any other known method. The 3D model creation circuit 172 generates a treatment plan based on the 3D model of the teeth of the patient. The treatment plan includes a first tooth configuration based on the 3D model of the teeth, and a second tooth configuration based on an optimal tooth configuration (e.g., the treatment plan can include moving the teeth from a crooked configuration to a straight configuration). The 3D model creation circuit 172 determines a number of steps in the treatment plan required to move the teeth from the first configuration to the second configuration, and generates 3D models of the teeth for each step in the treatment plan. The 3D model creation circuit 172 can also create physical representations of the 3D models via any known method including, but not limited to, 3D printing, machining, molding, or any other method capable of creating a physical 3D model. The 3D model creation circuit 172 sends the physical 3D models to the aligner fabrication system 174.

The aligner fabrication system 174 receives the physical 3D models from the 3D model creation circuit 172 and generates aligners for repositioning the teeth of a patient. The aligner fabrication system 174 includes a thermoforming machine 176, a cutting machine 178, and a laser etching machine 180. The thermoforming machine is operable to create an aligner by placing a sheet of polymeric material on top of one or more 3D models. The polymeric material is heated and drawn tightly over the 3D models (e.g., via a vacuum system, a press, or any other known methods). The polymeric material is allowed to cool, and the thermoformed polymeric material is removed from the 3D model.

The cutting machine 178 receives the thermoformed polymeric material from the thermoforming machine 176 and is operable to trim excess polymeric material from the thermoformed polymeric material. The excess material is trimmed with a cutting system (e.g., using lasers, mechanical methods, or other known cutting methods) to generate the aligners.

The laser etching machine 180 is operable to include identification marks on the aligners via a laser etching process. The identification marks can include a patient specific number, a sequence number indicating how the aligner should be worn in sequence with other aligners, or any other type of marks that can provide an identifying feature.

As described, the images recorded by the scanning device 102 can be processed and modified by the scanning device 102, the mobile device 122, the cloud server 142, and/or the aligner fabrication center 162. In some embodiments, the images recorded by the scanning device 102 can be at least partially processed by a combination of at least two or more of the scanning device 102, the mobile device 122, the cloud server 142, or the aligner fabrication center 162 such that the combination of partial processing results in fully processed and modified images.

Figure 1B:
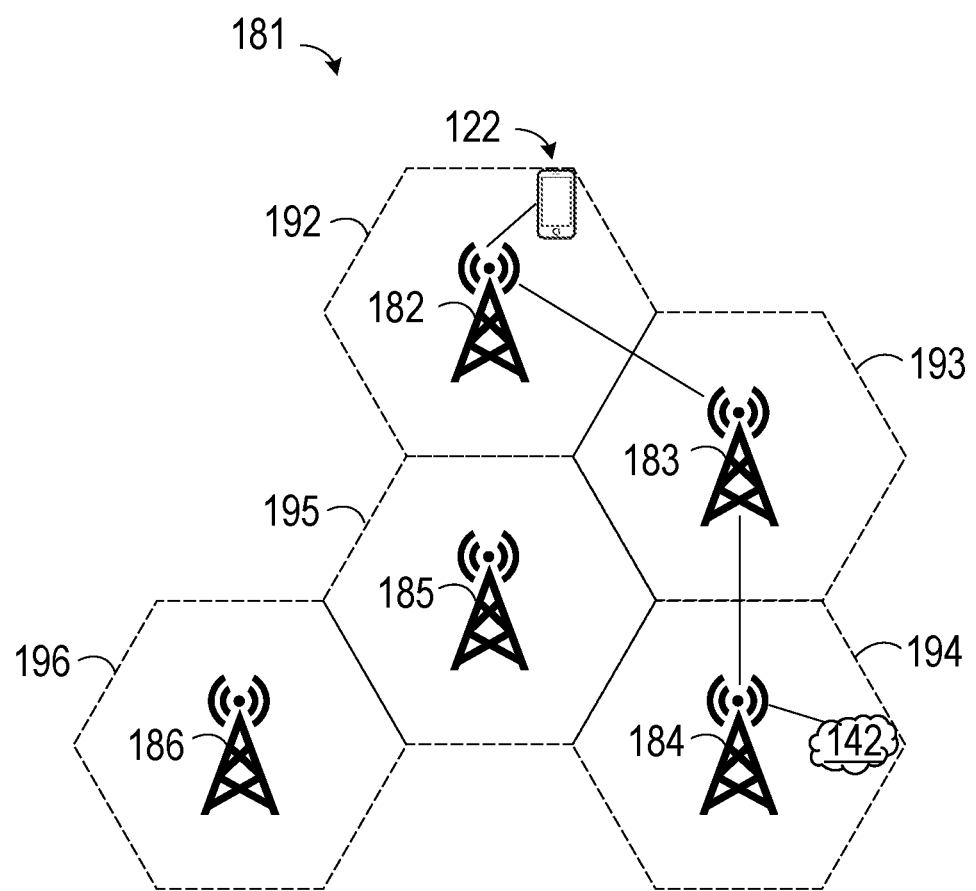
FIG. 1B is an illustration of the mobile device of FIG. 1A in communication with the cloud server of FIG. 1A, according to some embodiments.

Referring to FIG. 1B, an illustration of the mobile device 122 of FIG. 1A in communication with the cloud server 142 of FIG. 1A is shown, according to some embodiments. A tower network 181 includes a plurality of towers (e.g., towers 182-186). The towers 182-186 can be referred to as cellular towers, radio towers, base stations, base transceiver stations, etc., and include equipment for cellular communication. For example, the towers 182-186 can include various antennae, transmitters, receivers, transceivers, digital signal processors, control electronics, global positioning receivers, and electrical power sources. The towers 182-186 are configured such that each of the towers 182-186 can send and receive signals within a specified area (e.g., a cell). Typically, the area in which each of the towers 182-186 can send and receive signals is shaped approximately like a hexagon. For example, the tower 182 can send and receive signals (e.g., data) within the area 192, the tower 183 can send and receive signals within the area 193, the tower 184 can send and receive signals within the area 194, the tower 185 can send and receive signals within the area 195, and the tower 186 can send and receive signals within the area 196.

To send a signal from an originating location to a destination location, each tower can send a signal to a tower within an adjacent area. For example, the tower 182 can send a signal to the tower 183 because the area 193 is adjacent to the area 192. Additionally, the tower 182 can send a signal to the tower 185 because the area 195 is adjacent to the area 192.

As described with reference to FIG. 1A, the communication circuit 132 of the mobile device 122 sends signals (e.g., radio signals containing data related to a scan) from the mobile device 122 to communicate with the cloud server 142. In an example embodiment, the signal originates from the communication circuit 132 of the mobile device 122. Because the mobile device 122 is within the area 192, the signal reaches the tower 182. From the tower 182, the signal is sent to the tower 183 because the area 193 is adjacent to the area 192, and from the tower 183 the signal is sent to the tower 184 because the area 194 is adjacent to the area 193. The signal is then sent from the tower 184 to the cloud server 142 because the cloud server 142 is located within the area 194.

In some embodiments, the signals sent by the mobile device 122 include multiple digital signals, multiple analog signals, or a combination of multiple digital and analog signals. In such embodiments, the multiple signals are combined into one signal using multiplexing protocols to reduce the resources required to send the signal. In an example embodiment, frequency division multiplexing (FDM) can be used to combine the signals. In FDM, each user is assigned a different frequency from the complete frequency spectrum such that all frequencies can travel simultaneously. In another example embodiment, time division multiplexing (TDM) can be used to combine the signals. In TDM, a single radio frequency is divided into multiple slots and each slot is assigned to a different user such that multiple users can be supported simultaneously. In yet another example embodiment, code division multiplexing (CDMA) can be used to combine the signals. In CDMA, several users share the same frequency spectrum simultaneously and are differentiated via unique codes assigned to each user. The receiver is supplied with the unique keys such that the user can be identified by the receiver.

In some embodiments, the signal is sent via a packet switching process. In a packet switching process, the signal (e.g., the data being sent) is divided into smaller parts called packets. The packets are then sent individually from the source (e.g., the mobile device 122) to the destination (e.g., the cloud server 142). In some embodiments, each packet can follow a different path to the destination, and the packets can arrive out of order at the destination, where the packets are assembled in order (e.g., the datagram approach). In some embodiments, each packet follows the same path to the destination, and the packets arrive in the correct order (e.g., the virtual circuit approach).

Accordingly, any data acquired by the scanning device 102 can be communicated to the cloud server 142 or the aligner fabrication center 162 by way of or not by way of cloud server 142 using the tower network 181. In some embodiments, any data acquired by the scanning device 102 can be communicated using one or more towers 182-186 of the tower network 181. For example, 3D images of the user's teeth captured by the scanning device 102 can be communicated to the cloud server 142 or the aligner fabrication center 162 by way of one or more towers the 182-186 of the tower network 181. Additionally, 3D images of the user's teeth captured by the scanning device 102 can be communicated directly to other locations (e.g., the office of a dental professional, etc.) by way of one or more of the towers 182-186 for diagnostic purposes, treatment purposes, or any other purpose. In some cases, communicating 3D image data over the tower network 181 is advantageous over other methods of communication. For example, the 3D image data can be more efficiently communicated when broken up into smaller sized packets or smaller file sizes and separately communicated over the tower network 181 rather than being communicated in a large file size or larger packets when using other methods of communication.

Figure 2:
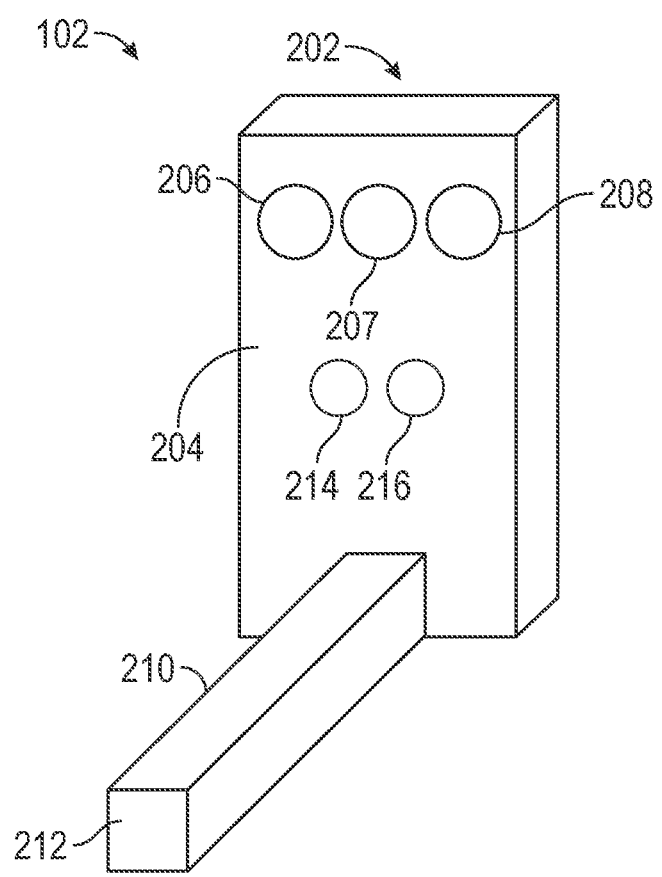
FIG. 2 is an illustration of a scanning device for scanning teeth, according to some embodiments.

Referring now to FIG. 2, an illustration of the scanning device 102 for scanning teeth is shown, according to some embodiments. The scanning device 102 can be any known device capable of capturing images of a 3D object for the purpose of creating a 3D model. In an example embodiment, the scanning device 102 is configured to capture images of a 3D object based on a "depth from stereo" concept (e.g., the depth of the 3D object is determined by comparing images obtained from at least two cameras positioned at angles to the 3D object). The scanning device 102 includes a body 202, a front portion 204, a first camera 206, a second camera 208, a projector 207, a guide bar 210, and a guide tip 212. The body 202 is sized and configured to be held in the hand of a patient during a scan of the teeth of the patient. In another embodiment, a person other than the patient having their teeth being scanned can hold and operate the scanning device 102 to scan the teeth of the patient. The body 202 can be manufactured from a plastic material (e.g., polycarbonate, polyethylene, or any other suitable plastic), a metal material (e.g., aluminum, stainless steel, or any other suitable metal), or any other material suitable for the application.

The first camera 206 and the second camera 208 are spaced apart and secured to the body 202 such that the lenses of the first camera 206 and the second camera 208 extend beyond the front portion 204. In some embodiments, the first camera 206 and the second camera 208 can be equivalent cameras. For example, the first camera 206 and the second camera 208 can be two-dimensional cameras that capture two-dimensional images along with some depth information. In some embodiments, the first camera 206 and the second camera 208 can be different cameras. For example, the first camera 206 can be a two-dimensional camera that captures depth information, and the second camera 208 can be a 3D camera.

The projector 207 is shown to be located in between the first camera 206 and the second camera 208; however, the projector 207 can be located anywhere on the body 202. The projector 207 receives the images from the first camera 206 and the second camera 208 and overlays the images from the first camera 206 and the second camera 208. The overlaid images are provided to the analysis circuit 116 and the analysis circuit 116 can stereoscopically calculate the depth of the images from the first camera 206 and the second camera 208. In some embodiments, the projector 207 includes a light source and the projector 207 projects light from the light source toward the object being scanned. The light source can be, for example, a near infrared light, a light in the visible spectrum (e.g., light with a wavelength between approximately four hundred and approximately seven hundred nanometers). In some embodiments, the light source is a light with a wavelength of between approximately three hundred eighty nanometers and five hundred nanometers.

The scanning device 102 may also include a light source 214 to project light on the surface for scanning. In some embodiments, the light source 214 can project visible light onto the surface for scanning (e.g., blue light or any other type of visible light). In some embodiments, the light source 214 can project infrared light (or other non-visible light, e.g. near-infrared light) onto the surface for scanning. The light source 214 can be turned on prior to the scanning procedure, either by the user (e.g., via a button, switch, or other type of actuator that can open or close a circuit coupled to the light source 214) or automatically.

In some embodiments, the scanning device 102 includes sensors 216 to receive light reflected from the surfaces being scanned. In some embodiments, the sensors 216 are configured to receive infrared light (or other non-visible light) reflected from the surfaces being scanned. In some embodiments, the sensors 216 are configured to receive visible light (e.g., blue light or any other type of visible light) reflected from the surfaces being scanned. In embodiments where the light source 214 is turned on automatically, the sensors 216 can be configured to detect the motion and/or orientation of the scanning device 102. When the sensors 216 detect motion indicative of a scanning procedure (e.g., the scanning device 102 is oriented at a certain angle or angles, the scanning device 102 is moved according to a certain pattern, etc.) the sensors 216 send a signal to the light source 214 such that the light source 214 turns on.

In some embodiments, the scanning device 102 may include bone scanning technology. Bone scanning technology may include various systems and methods to scan the exterior and interior of a bone. For example, in a dental environment, a bone scan may provide information regarding the internal health of teeth. A bone scan may also provide information regarding the health of the roots of the teeth, or other portions of the teeth that may not be visible such that they cannot be scanned by a conventional scanning device. In some embodiments, the bone scanning technology enables acquisition of the shape of teeth roots and the position of teeth roots with respect to one another, teeth of the user, or a jawbone of the user.

The guide 210 extends from the front portion 204 and defines a guide tip 212, where the guide tip 212 is located at the end of the guide 210 opposite the front portion 204. The guide 210 can be constructed from the same material as the body 202; however, the guide 210 can also be constructed from different materials. The guide 210 is operable to extend between the teeth of a patient and the body 202 during a scan of the teeth of the patient, therefore the guide 210 is substantially rigid such that the body 202 can be maintained at a substantially constant distance (e.g., between 2-6 centimeters (cm), around 3 cm, around 4 cm, etc.) from the teeth of the patient during the scan.

The guide tip 212 is operable to contact the teeth of the patient throughout the scan such that the body 202 can be maintained at a substantially constant distance from the teeth of the patient during the scan. As shown, the guide tip 212 is a flat surface; however, the guide tip 212 can be any shape that directs the patient to maintain contact between the guide tip 212 and the teeth during a scan. For example, the guide tip 212 can be shaped like a "V" such that the teeth can be inserted into the "V" to maintain contact throughout the scan. As another example, the guide tip 212 can be shaped like a "U" such that the teeth can be inserted into the "U" to maintain contact throughout the scan. The guide tip 212 can be oriented in any configuration to promote accurate scanning. For example, in the embodiment where the guide tip 212 is "V" shaped, the "V" can be oriented such that the opening of the "V" is facing down (e.g., away from the first camera 206 and the second camera 208). As another example, in the embodiment where the guide tip 212 is "U" shaped, the "U" can be oriented such that the opening of the "U" is facing up (e.g., toward the first camera 206 and the second camera 208).

In embodiments where the scanning device 102 scans structures inside of a mouth (e.g., teeth, gums, etc.), the scanning device 102 is preferably capable of scanning at a resolution of approximately 100 microns when scanning an individual tooth. Furthermore, the scanning device 102 is preferably capable of a resolution of approximately 300 microns when conducting a cross-arch scan (e.g., scanning all the upper teeth or all the lower teeth). In some embodiments, the scanning resolution is preferably greater (e.g., between approximately 50-100 microns when scanning an individual tooth and between approximately 100-300 microns when conducing a cross-arch scan).

Figure 3:
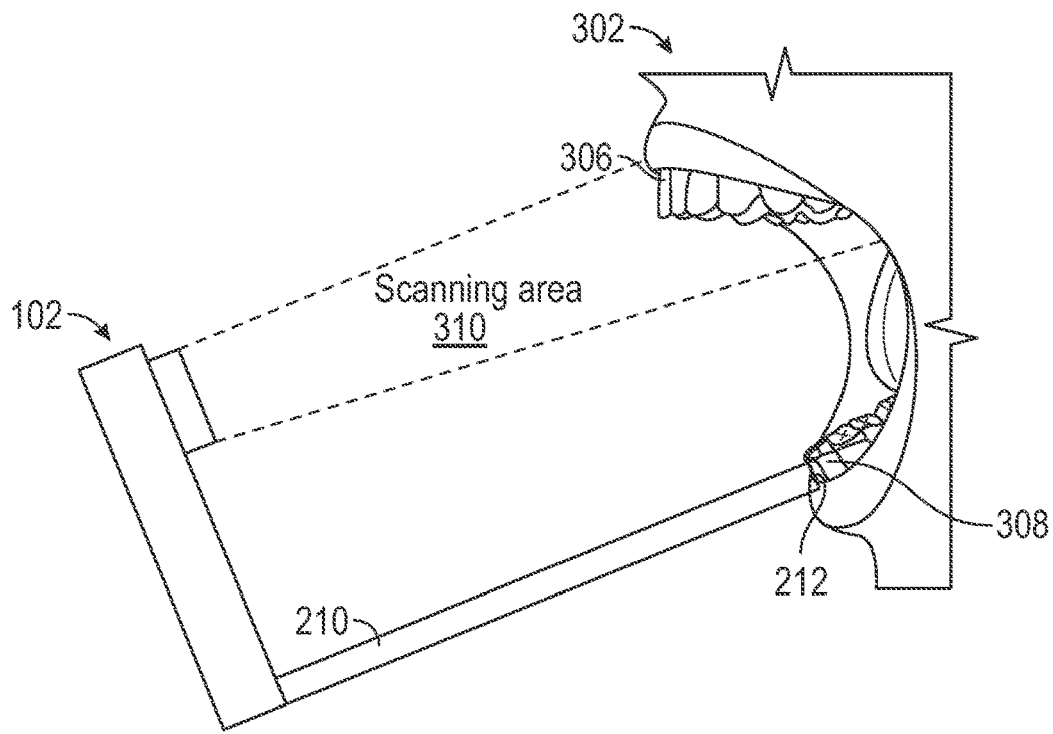
FIGS. 3-4 are illustrations of a process for scanning teeth using the scanning device of FIG. 2, according to some embodiments.
Figure 4:
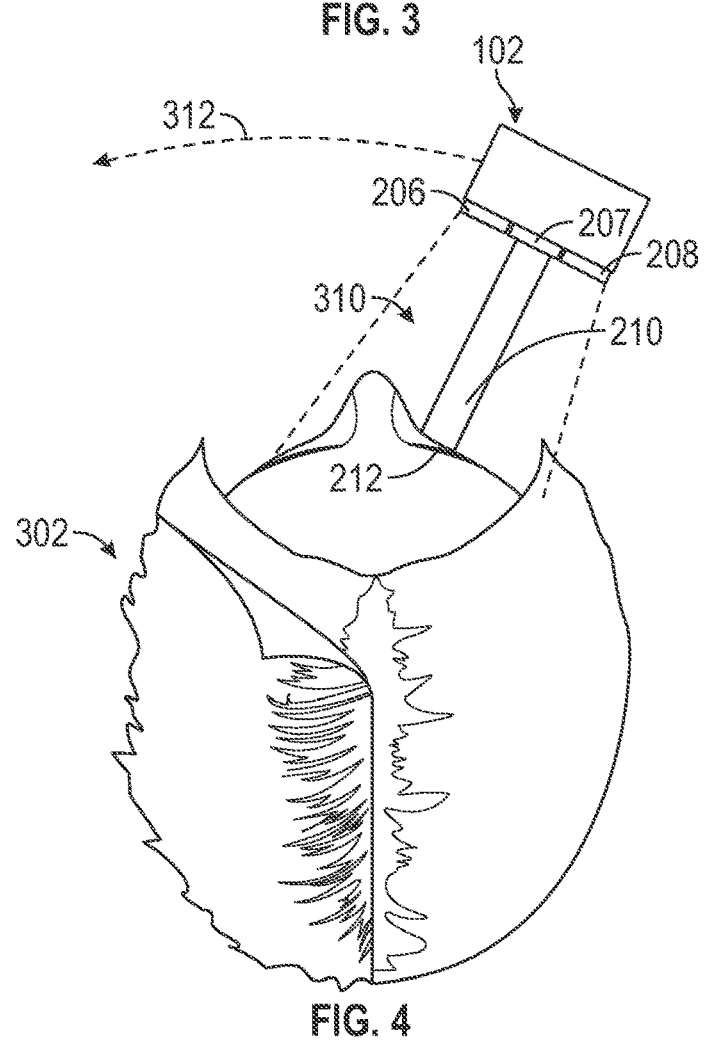

Referring to FIGS. 3-4, illustrations of a process for scanning teeth using the scanning device 102 of FIG. 2 are shown, according to some embodiments. As shown in the figures, a patient 302 has upper teeth 306 and lower teeth 308, and the patient 302 desires to receive and use aligners to move the upper teeth 306 and the lower teeth 308 such that they look straighter. To begin the aligner creation process, the patient 302 is sent the scanning device 102 to scan the upper teeth 306 and the lower teeth 308. The patient 302 is also instructed to download an application to the mobile device 122 (not shown). The mobile device 122 provides instructions to the patient 302 regarding how to properly conduct a scan of the teeth. The instructions to the patient 302 will be described in more detail with reference to FIGS. 9-20.

To generate a scan of the teeth, the patient 302 places the guide tip 212 in a specific section of the mouth, as instructed. For example, the guide tip 212 may be positioned on the back molar on the right side of lower teeth 308 to begin the scan. By placing the guide tip 212 on the lower teeth 308, the scan of the teeth will begin by scanning in the scanning area 310 (e.g., the upper teeth 306) to prevent the scanning device 102 from confusing the guide tip 212 with the teeth to be scanned. After the scan begins, the patient 302 moves the scanning device 102 around the mouth in the direction of the arrow 312 while keeping the guide tip 212 in contact with the lower teeth 308. As the patient 302 moves the scanning device 102 around the mouth, the first camera 206 and the second camera 208 record images of the upper teeth 306. The patient 302 moves the scanning device 102 until the guide tip 212 contacts the back molar on the left side of the lower teeth 308. The scan of the upper teeth 306 is complete.

The patient rotates the scanning device 180 degrees and places the guide tip 212 in a specific section of the mouth, as instructed. For example, the guide tip 212 may be positioned on the back molar on the right side of upper teeth 306 to begin the scan of the lower teeth 308. With the scanning device 102 oriented in this manner, the scanning area 310 is focused on the lower teeth 308. The patient 302 moves the scanning device 102 around the mouth in the direction of the arrow 312 while keeping the guide tip 212 in contact with the upper teeth 306. As the patient 302 moves the scanning device 102 around the mouth, the first camera 206 and the second camera 208 record images of the lower teeth 308. The patient 302 moves the scanning device 102 until the guide tip 212 contacts the back molar on the left side of the upper teeth 306. The scan of the lower teeth 308 is complete.

In some embodiments, the guide 210 is not included on the scanning device 102. In such embodiments, the scanning device 102 may be inserted into the mouth to bring the camera 206 and the camera 208 closer to the teeth for scanning. In some embodiments, the guide 210 is included on the scanning device 102, but the user can determine whether to use the guide 210 or insert the scanning device 102 into the mouth to scan the teeth.

In some embodiments, after the scan of the lower teeth 308 and the upper teeth 306 is complete, the images are sent to the cloud server 142 for further processing. In some embodiments, the images are sent to the cloud server 142 in batches. For example, after scanning the right quadrant of the upper teeth 306, the images of the right quadrant of the upper teeth 306 are sent to the cloud server 142. Furthermore, after scanning the left quadrant of the upper teeth 306, the images of the left quadrant of the upper teeth 306 are sent to the cloud server 142. In embodiments where the images are sent to the cloud server 142 in batches, the patient 302 may be instructed to stop scanning at certain points to allow the images to be sent to the cloud server 142. For example, after scanning the right quadrant of the upper teeth 306, the patient 302 may be instructed to stop the scan to allow the images to be sent to the cloud server 142, and then instructed to begin the scan again after the images are sent.

Figure 5:
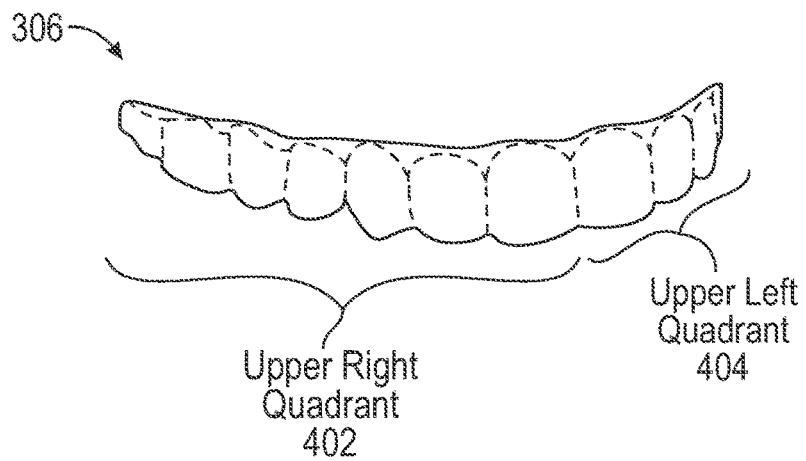
FIG. 5 is an illustration of the teeth of a patient, according to some embodiments.

Referring to FIG. 5, an illustration of the upper teeth 306 of the patient 302 are shown, according to some embodiments. The upper teeth 306 includes an upper right quadrant 402 and an upper left quadrant 404. In embodiments where the patient scans teeth in batches, the first camera 206 and the second camera 208 can record two-dimensional images of the upper right quadrant 402 during a first portion of the scan and the upper left quadrant 404 during a second portion of the scan. As described, the projector 207 can combine the images from the first camera 206 and the second camera 208 to create 3D images of the upper right quadrant 402 and the upper left quadrant 404, and the 3D images of the upper right quadrant 402 and the upper left quadrant 404 are provided to the cloud server 142 for high-resolution reconstruction.

Figure 6:
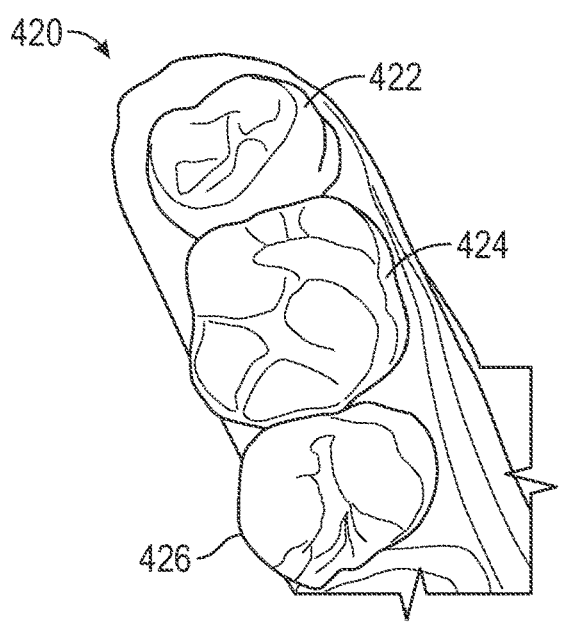
FIG. 6 is an illustration of a high-resolution reconstruction of the teeth of a patient, according to some embodiments.

Referring to FIG. 6, an illustration of a high-resolution reconstruction 420 of the teeth of a patient 302 is shown, according to some embodiments. For example, the high-resolution reconstruction 420 may be a portion of the upper right quadrant 402 of FIG. 5. The high-resolution reconstruction 420 includes a first tooth 422, a second tooth 424, and a third tooth 426. After the cloud server 142 receives the 3D images of the upper right quadrant 402, the cloud server 142 generates the high-resolution reconstruction 420 of the first tooth 422, the second tooth 424, and the third tooth 426 such that attributes like the shape, depth, and angles of each tooth can be converted to a 3D model for creation of an aligner.

Figure 7:
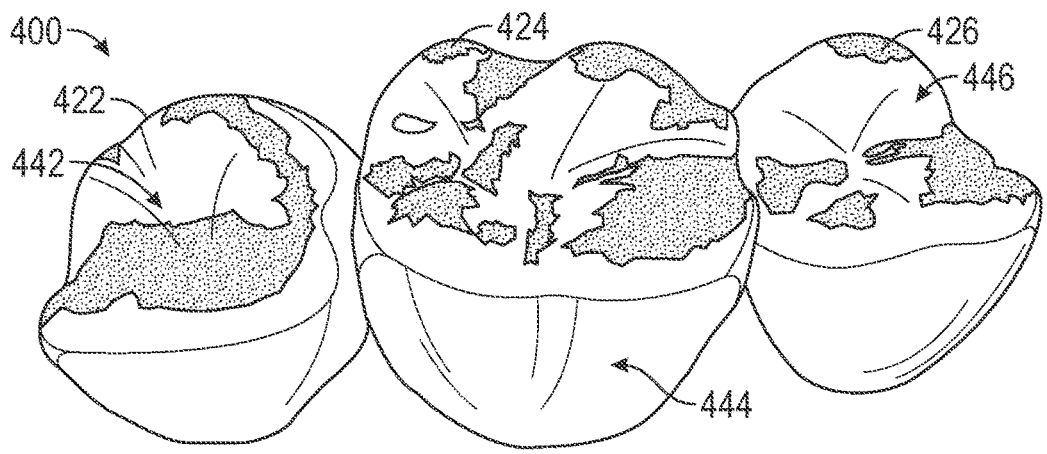
FIG. 7 is an illustration of a computer-generated mesh based on the high-resolution reconstruction of FIG. 6 is shown, according to some embodiments.

Referring to FIG. 7, an illustration of a computer-generated mesh 440 based on the high-resolution reconstruction 420 of FIG. 6 is shown, according to some embodiments. The cloud server 142 provides the high-resolution reconstruction 420 to the aligner fabrication center 162 to create one or more aligners. The aligner fabrication center 162 can receive more than one high-resolution reconstruction (including the high-resolution reconstruction 420) such that the image recognition circuit 168 and the image stitching circuit 170 can create a 3D image of the full set of teeth (e.g., the top teeth 306). The 3D image is provided to the 3D model creation circuit 172 to create the 3D model of the teeth. The 3D model creation circuit 172 analyzes the 3D image and generates the computer generated mesh 440 that includes a first tooth mesh 442, a second tooth mesh 444, and a third tooth mesh 446. The first tooth mesh 442, second tooth mesh 444, and third tooth mesh 446 include a plurality of nodes that correspond to features on the surfaces of the teeth (e.g., bumps, angles, ridges, etc.). The computer generated mesh 440 is used to generate the 3D model of the teeth, which is then 3D printed to generate a physical 3D model. The computer generated mesh 440, as shown, includes only three teeth for purposes of example. A full 3D image of the teeth can be used to generate a full computer generated mesh of the teeth, which can be used to generate a full 3D model of the teeth.

Figure 8:
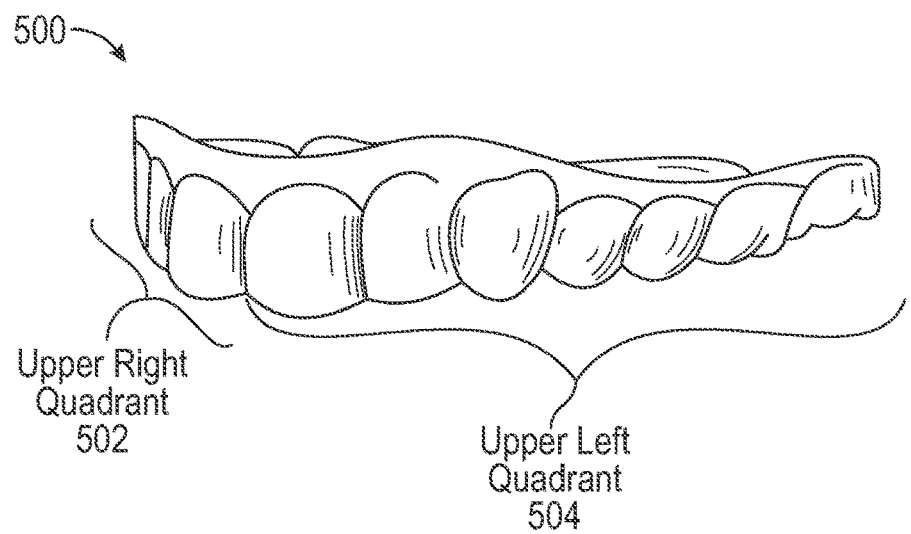
FIG. 8 is an illustration of an aligner, according to some embodiments.
Figure 9:
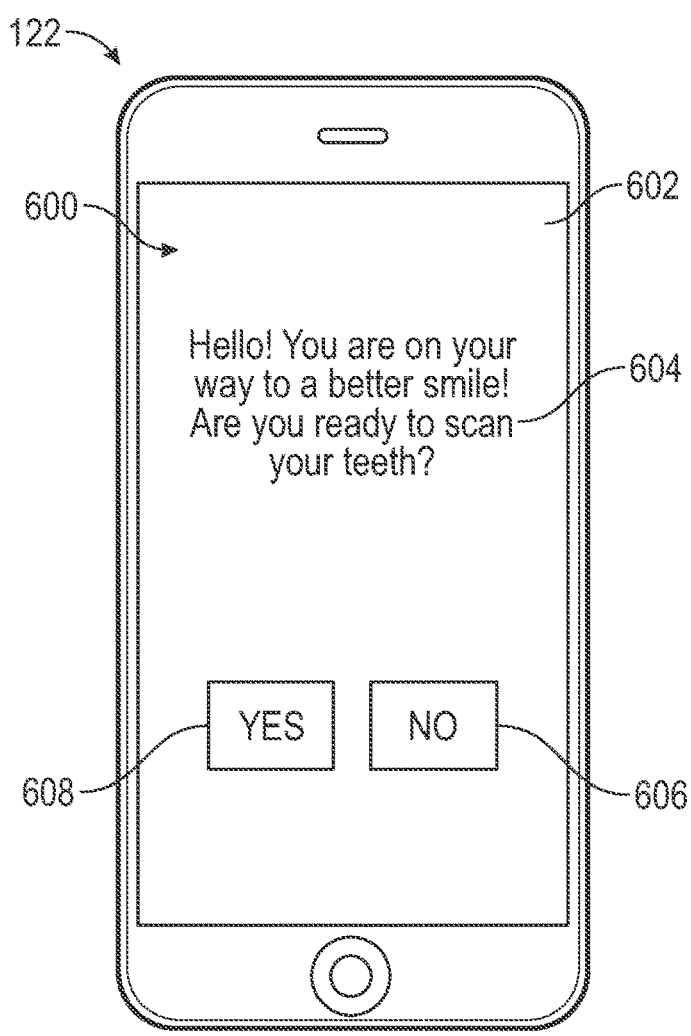
FIGS. 9-20 are illustrations of a mobile device application instructing a patient how to scan teeth using the scanning device of FIG. 2, according to some embodiments.
Figure 11:
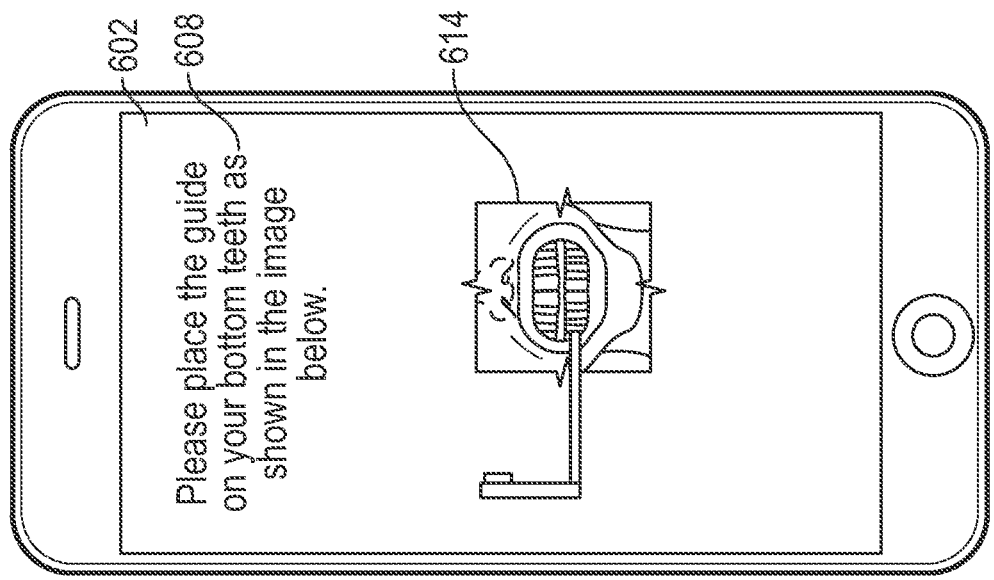
Figure 10:
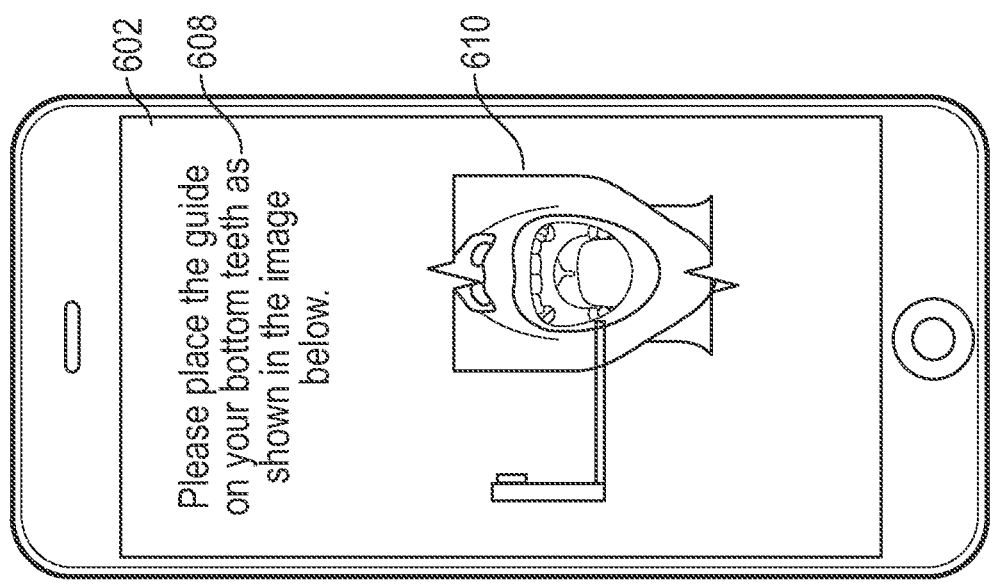
Figure 13:
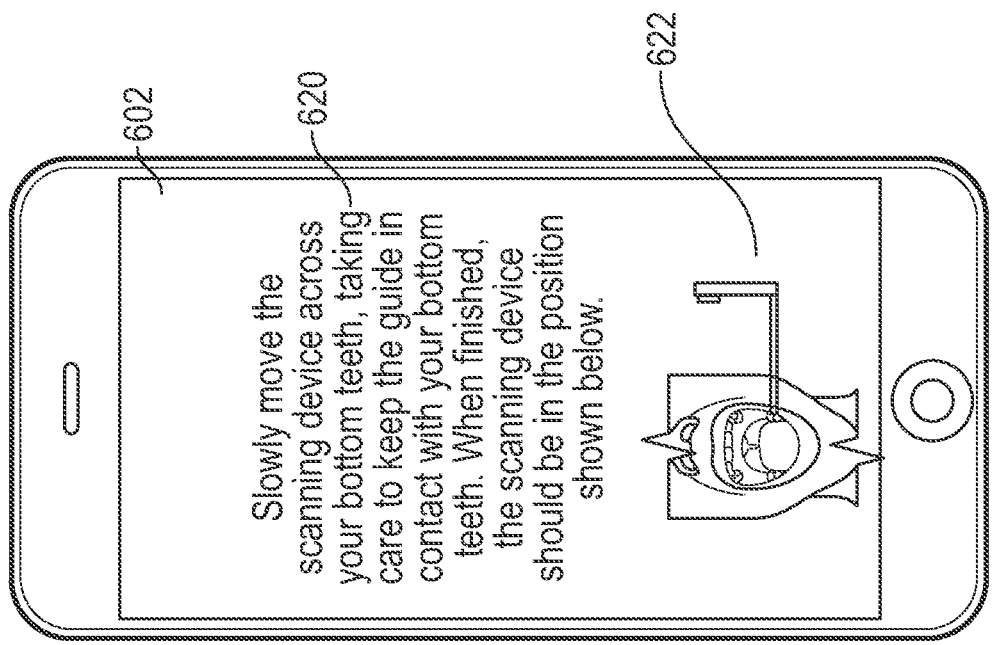

Referring to FIG. 8, an illustration of an aligner 500 is shown, according to some embodiments. The aligner 500 includes an upper right quadrant 502 that corresponds to the upper right quadrant 402 of FIG. 5, and an upper left quadrant 504 that corresponds to the upper left quadrant 404 of FIG. 5. After the physical 3D model of the teeth is printed by the 3D model creation circuit 172, the physical 3D model is received by the aligner fabrication system 174. A sheet of a polymeric material is used to create the aligner 500 using the thermoforming machine 176, the cutting machine 178, and the laser etching machine 180, as described.

In some embodiments, a plurality of aligners is created, with each aligner including a slightly different geometry such that the aligner forces the teeth to be gradually repositioned. In embodiments where a plurality of aligners is created, the upper right quadrant 502 and the upper left quadrant 504 may have geometries slightly different from the upper right quadrant 402 and upper left quadrant 404. When the patient 302 inserts, for example, the upper teeth 306 into the aligner 500, the aligner 500 may exert forces on the upper teeth 306 that cause the upper teeth 306 to move.

Referring to FIGS. 9-20, illustrations of a mobile device application 600 instructing the patient 302 how to scan teeth using the scanning device 102 of FIG. 2 is shown, according to some embodiments. As described, the patient 302 is instructed to download the application 600 to the mobile device 122. The mobile device 122 includes a display 602 that can display messages to the patient 302 before, during, and after the scan.

After the patient 302 installs the application 600 on the mobile device 122, the patient 302 initiates the application 600 to begin the scanning process. Upon initiating the application 600, the application 600 displays a message 604 on the display 602 asking the patient 302 if the patient 302 is ready to being the scanning process. If the patient 302 selects the no button 606, the application 600 may close or direct the patient 302 to begin the application 600 again when the patient 302 is ready to begin scanning. If the patient 302 selects the yes button 608, the mobile application 600 will move to the next screen.

The mobile application 600 displays a message 608 regarding the initial position of the scanning device 102 relative to the teeth of the patient 302. As shown in image 610 of FIG. 10, in some embodiments the patient 302 does not need to use a device to spread the lips apart to begin the scan. As shown in image 614 of FIG. 11, in some embodiments the user needs to insert a device into the mouth to spread the lips apart to begin the scan. When the patient 302 is ready to begin the scan, the patient 302 is holding the scanning device 102 in one hand and the mobile device 122 in the other hand such that the patient 302 can view the display 602 while conducting the scan with the scanning device 102.

As shown, the patient 302 can conduct the scan of teeth using the guide 210 so the camera 206 and the camera 208 do not enter the mouth. However, the patient can also conduct the scan of the teeth by inserting the scanning device 102 into the mouth to scan the teeth, as described.

The mobile application 600 displays a message 616 prompting the patient 302 to begin the scan by pressing the start button 618. Upon pressing the start button 618, the message 620 is displayed to provide the patient 302 with instructions as to how to conduct the scan. An image 622 is also shown on the display to guide the patient 302 during the scan. In some embodiments, the image 622 is a short video showing the patient 302 how to conduct the scan. In some embodiments, the scanning device 102 communicates its position to the mobile application 600 in real time such that the display 602 can superimpose an image of the scanning device 102 with the image 622 and the patient 302 can attempt to match the position on the image to provide for a more accurate scan. In some arrangements, a confidence level is shown on the display 602. The confidence level provides the user with real time feedback regarding the accuracy of the scan. For example, the display 602 may indicate that the confidence level during the scan is 40%. Furthermore, the message may be highlighted in red to indicate that the confidence level is low for an accurate scan. As another example, the display 602 may indicate that the confidence level during the scan is 95%, and the message may be highlighted in green to indicate that the confidence level is high for an accurate scan. The scanning device 102 or application may alert the scanner when the confidence level does not meet a threshold (e.g., an audio, visual, or tactile alert when the confidence level is less than 95%).

After the scan of the first set of teeth is complete, the application provides a message 624 to the patient 302 instructing the patient 302 to orient the scanning device 102 to scan the other set of teeth. The message 628 is displayed to provide the patient 302 with instructions as to how to conduct the scan. An image 630 is also shown on the display to guide the patient 302 during the scan. In some embodiments, the image 630 is a short video showing the patient 302 how to conduct the scan. In some embodiments, the scanning device 102 communicates its position to the mobile application 600 in real time such that the display 602 can superimpose an image of the scanning device 102 with the image 630 such that the patient 302 can attempt to match the position on the image to provide for a more accurate scan. As described, confidence information can also be displayed in real time during the scan.

In some embodiments, the scan may not be successful. In such embodiments, the scanning device 102 provides the application 600 with data regarding the portion(s) of the scan that were unsuccessful, and the application 600 provides the patient 302 with the message 632 indicating that the scan was unsuccessful. An image 634 provides a highlighted section 636 to indicate to the user the specific portion of the scan that was unsuccessful. The patient 302 can then initiate a new scan in attempts to correct the deficiency.

Figure 17:
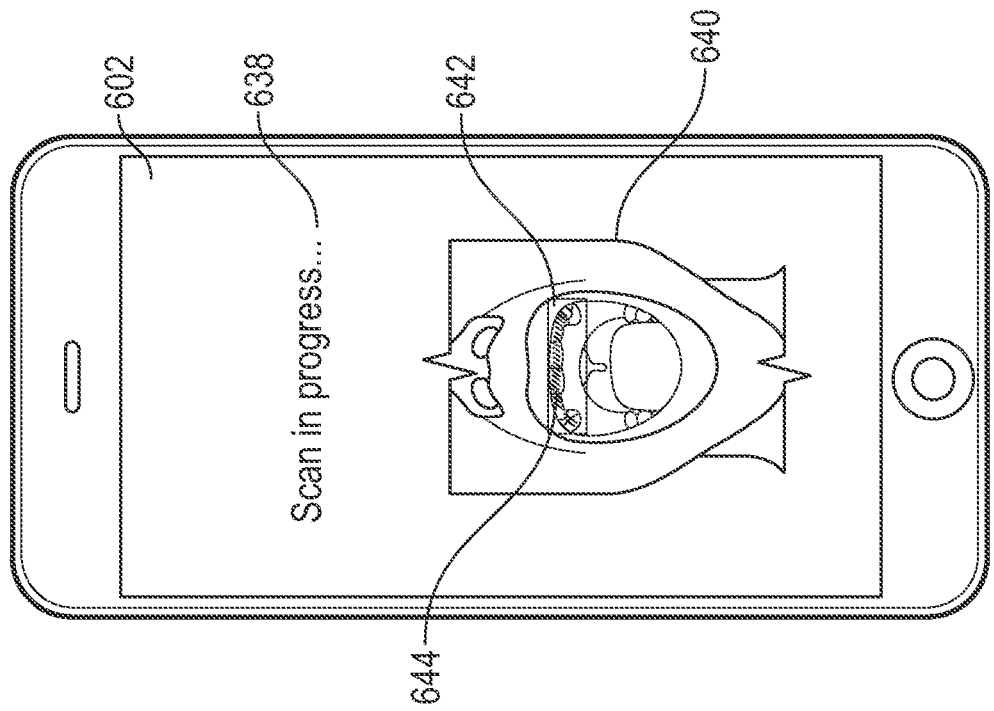

In some arrangements, as shown in FIG. 17, the scanning device 102 may provide the mobile application 600 with data in real time related to the appearance of the teeth being scanned by the patient 302. In such arrangements, the mobile application 600 can display an image 640 that includes the teeth 642 of the patient 302 instead of the generic teeth as shown in, for example, image 630 of FIG. 5. Additionally, the image 640 can include a highlighted section 642 that can indicate, in real time, whether the scan of a particular section of the teeth was successful. For example, in some embodiments the highlighted section 642 can be green, indicating a successful scan. In some embodiments, the highlighted section 642 can be red, indicating an unsuccessful scan. In some embodiments, the highlighted section 642 can include a combination of red and green, indicating that some portions of the scan are acceptable, and some portions of the scan are unacceptable.

When the scan is complete, a message 646 is provided to the patient 302 to advise the patient that the scan is being evaluated to determine whether it is acceptable or unacceptable. During this time, the scan data may be sent to the cloud server 142 to verify whether the scan is acceptable.

The patient 302 receives a message 648 indicating that the scan was successful, or the patient 302 receives a message 650 indicating that the scan was unsuccessful and that a new scan should be started by pressing the start scan button 652.

Figure 21:
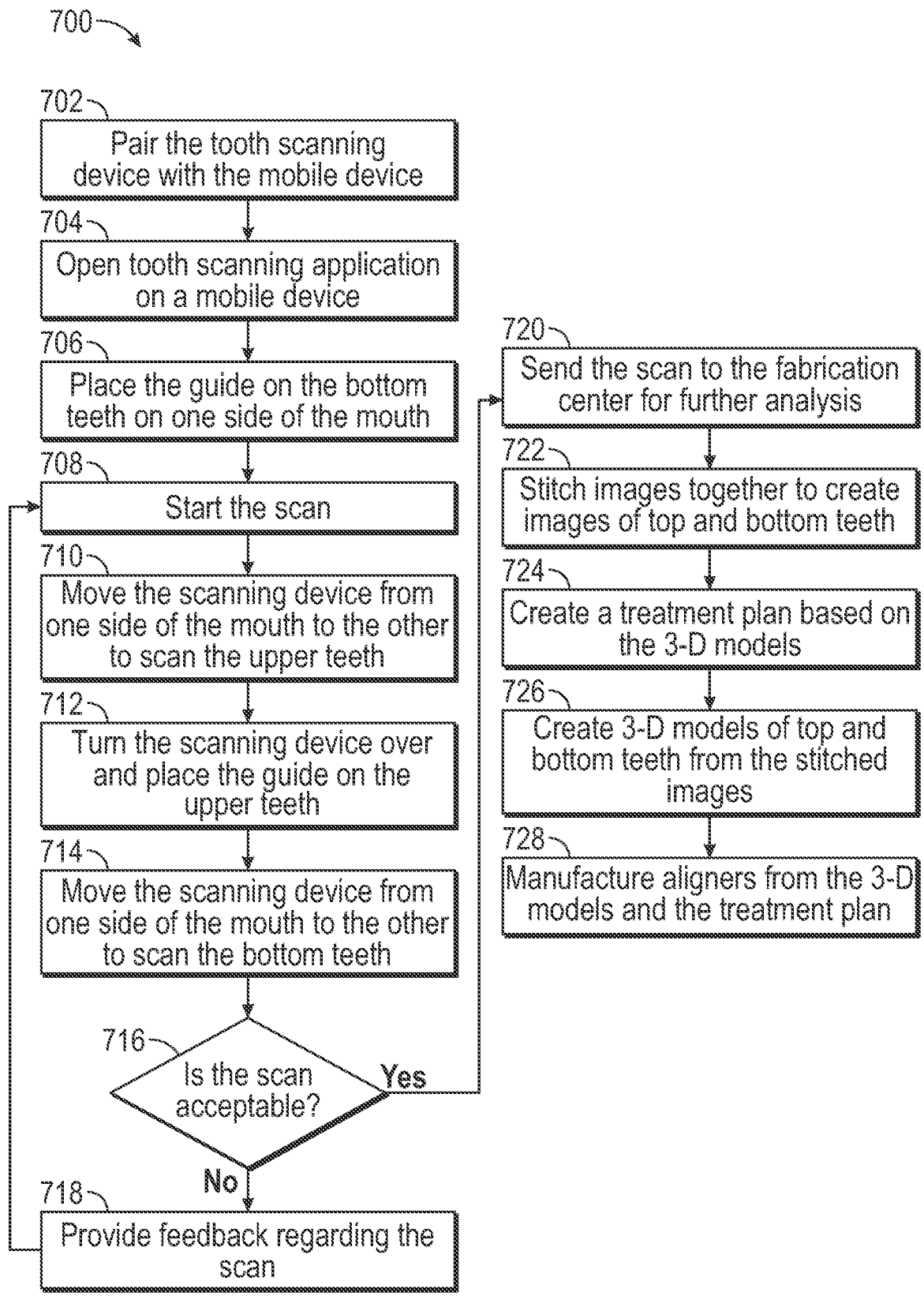
FIG. 21 is a flow diagram of a method for creating a dental aligner using the scanning device of FIG. 2, according to some embodiments.

Referring to FIG. 21, a flow diagram of a method 700 for creating a dental aligner using the scanning device 102 of FIG. 2 is shown, according to some embodiments. At 702, a tooth scanning device is paired with a mobile device. For example, the scanning device 102 is paired with the mobile device 122. In some embodiments, the scanning device 102 and mobile device 122 are paired using Bluetooth technology. In some embodiments, other known pairing methods can be used that would provide for communication between the scanning device 102 and the mobile device 122.

At 704, a tooth scanning application on the mobile device 122 is opened. For example, after downloading the application 600 to the mobile device 122, the patient 302 opens the application 600 on the mobile device 122.

At 706, the guide 210 is placed on the bottom teeth on one side of the mouth. For example, as shown in FIG. 3, the patient 302 places the guide tip 212 of the guide 210 on the lower teeth 308 in preparation for the scan.

Figure 12:
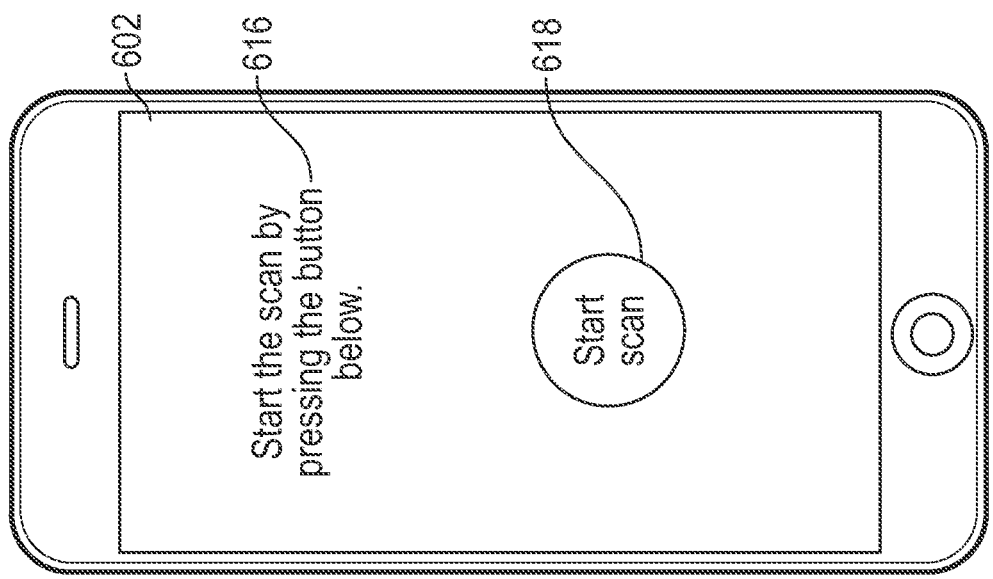
Figure 15:
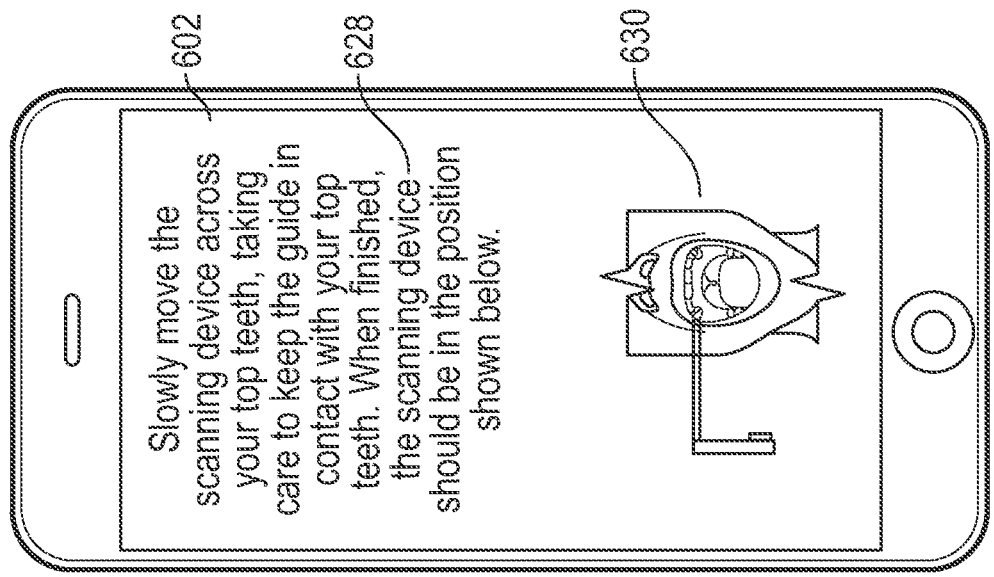
Figure 14:
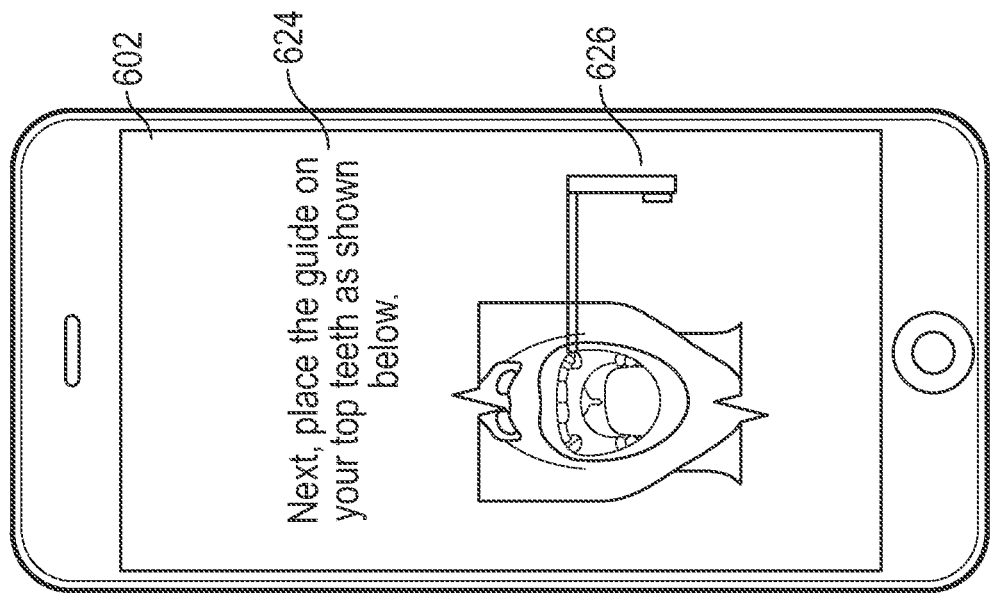

At 708, the scan is started. For example, as shown in FIG. 12, after properly positioning the scanning device 102 by placing the guide 210 on the lower teeth 308, the patient 302 can start the scan by pressing the start scan button 618 on the mobile device 122.

At 710, the scanning device 102 is moved from one side of the mouth to the other. For example, as shown in FIG. 4, the scanning device 102 is moved in the direction of the arrow 312 such that the scanning device 102 scans the upper teeth 306.

At 712, the scanning device 102 is turned over and the guide 210 is placed on the upper teeth 306. For example, the patient 302 places the guide tip 212 of the guide 210 on the upper teeth 306 on one side of the mouth.

At 714, the scanning device 102 is moved from one side of the mouth to the other. For example, as shown in FIG. 4, the scanning device 102 is moved in the direction of the arrow 312 such that the scanning device 102 scans the lower teeth 308.

Figure 16:
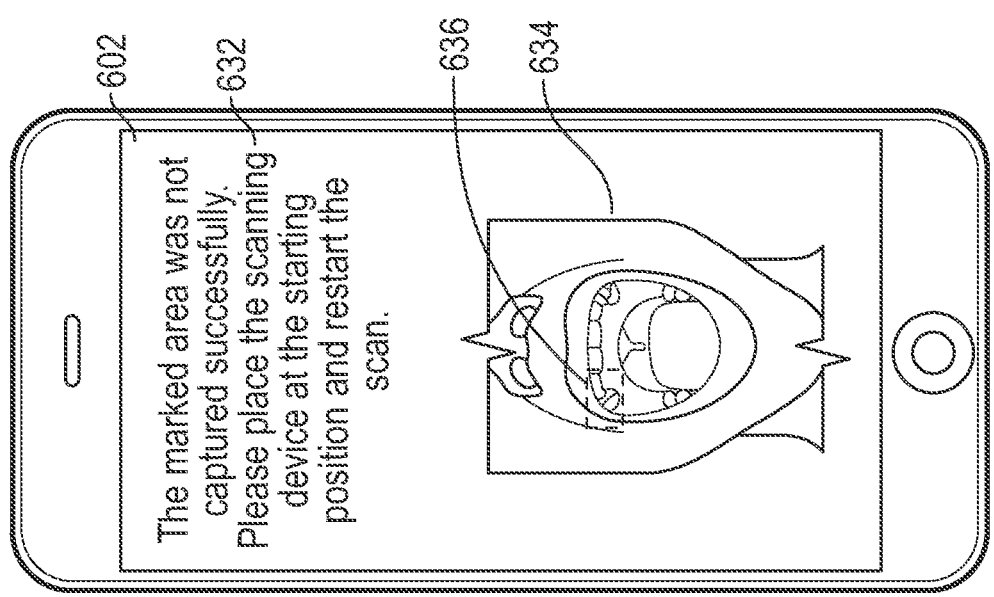
Figure 19:
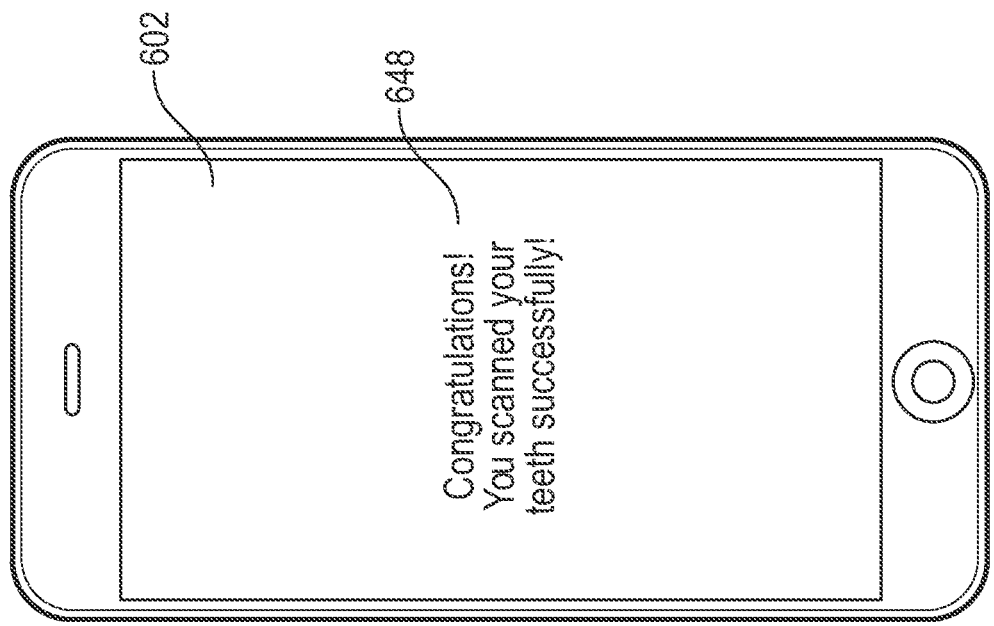
Figure 18:
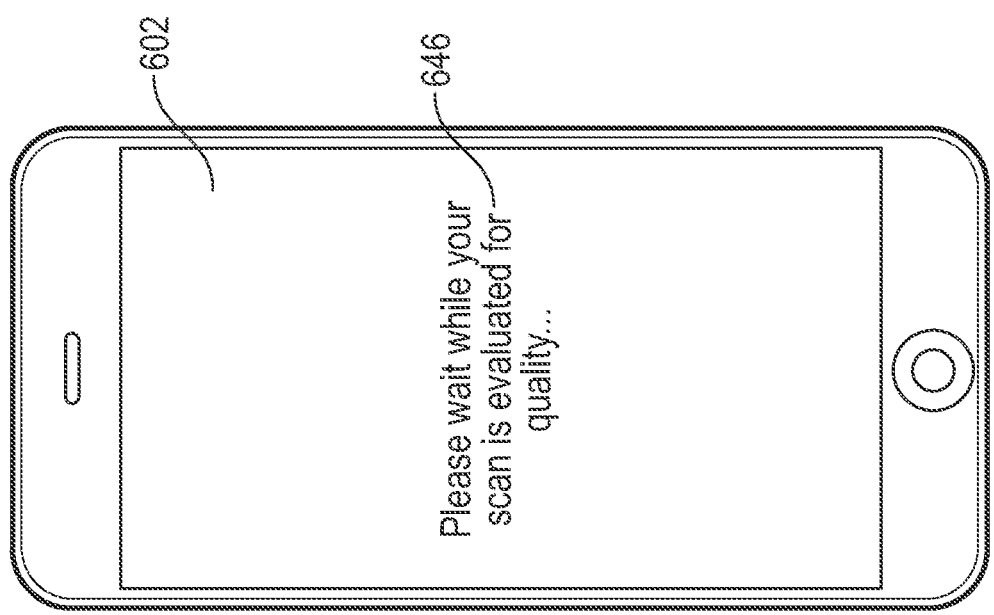
Figure 20:
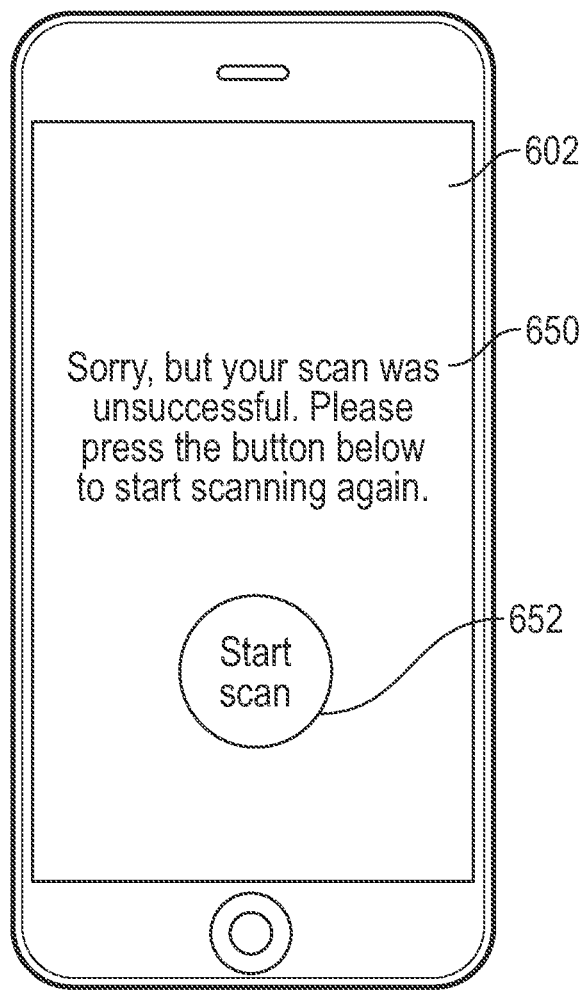

At 716, a determination is made as to whether the scan is acceptable. The determination can be made by either the scanning device 102 or the cloud server 142. In either case, if the scan is not acceptable, at 718 feedback is provided regarding the scan. For example, as shown in FIG. 16, a specific area or areas of the teeth of the patient 302 may be highlighted as one or more areas that were not scanned successfully. If the scan is acceptable, at 720 the scan is sent to the aligner fabrication center 162 for further analysis. For example, the image recognition circuit 168 determines and/or verifies the images from the scan correspond to the correct portions of the mouth (e.g., the image of the upper right quadrant of the mouth is actually the upper right quadrant of the mouth).

At 722, the images are stitched together to create a single image. For example, the image stitching circuit 170 stitches multiple images of the teeth together to create one 3D image of the top teeth and one 3D image of the bottom teeth from the scan. In some embodiments, a single 3D image including both the top teeth and the bottom teeth is created. In some embodiments, a single 3D image of the top teeth in contact with the bottom teeth (e.g., bite articulation) is created based on one or more scans conducted with the top teeth and bottom teeth in a bite articulation position.

At 724, a treatment plan is created based on the 3D image of the teeth. For example, the 3D image of the teeth of the patient 302 is compared to the 3D image of straightened teeth, and the aligner fabrication computer system 164 determines the number of aligners needed to move the teeth from the initial configuration to the straightened configuration.

At 726, one or more 3D models of the teeth are created. For example, the 3D model creation circuit 172 generates a mesh similar to the mesh 440 of FIG. 7 such that a physical 3D model of the teeth can be created by any known method (e.g., 3D printing, molding, etc.). Physical 3D models are created for each step in the treatment plan.

At 728, aligners are manufactured from the 3D models. For example, aligners are manufactured using the thermoforming machine 176, the cutting machine 178, and the laser etching machine 180, as described. Aligners can be manufactured singly, or in batches. When manufactured in batches, a plurality of physical 3D models are arranged such that a large sheet of polymeric material fits over all the physical 3D models. The polymeric material is heated and formed to the physical 3D models to create the aligners, as described.

Figure 22:
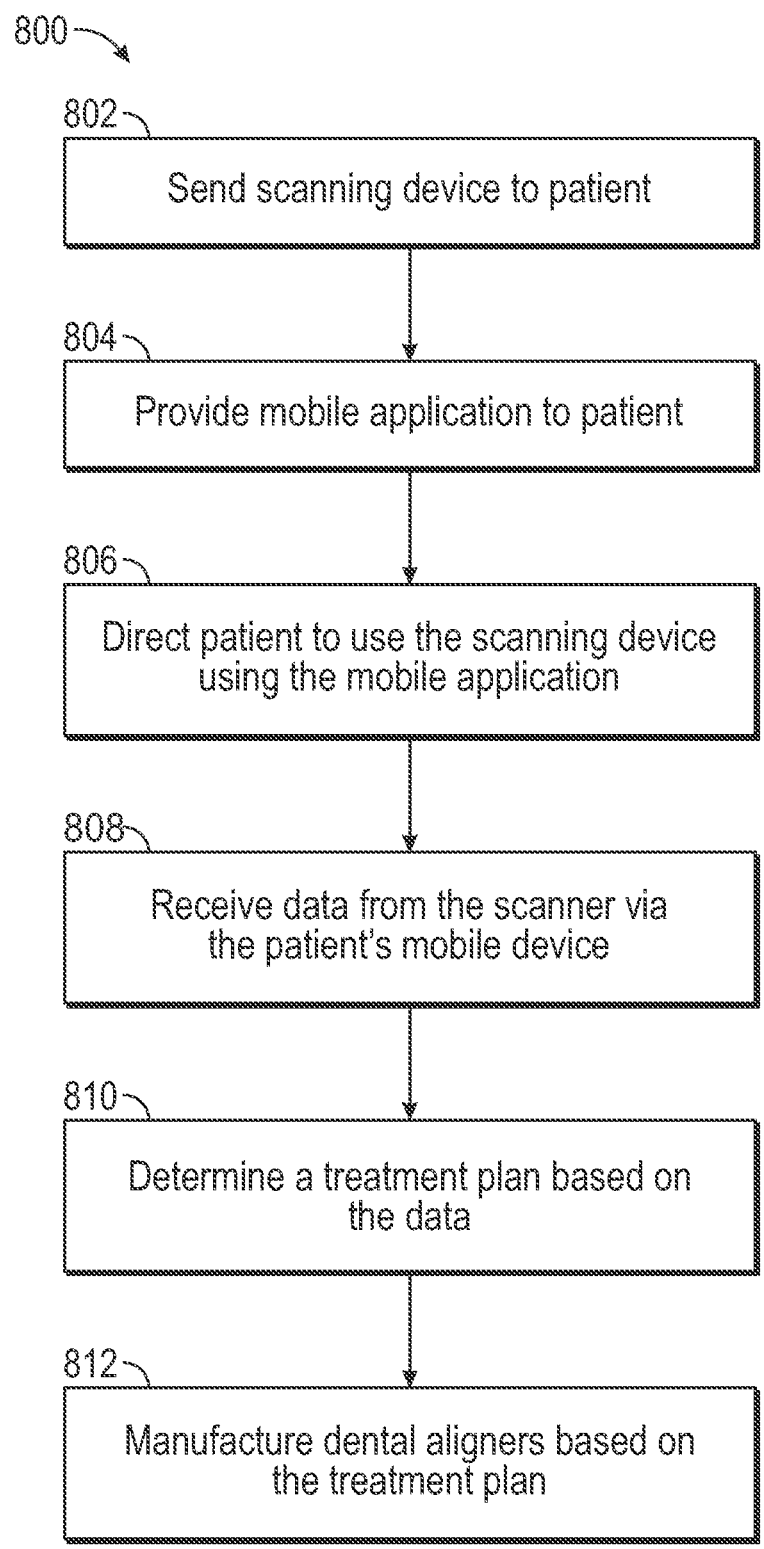
FIG. 22 is a flow diagram of a method for creating a dental aligner using the scanning device of FIG. 2, according to some embodiments.

Referring to FIG. 22, a flow diagram of a method 800 for creating a dental aligner using the scanning device 102 of FIG. 2 is shown, according to some embodiments. At 802, a scanning device is sent to a patient. For example, the scanning device 102 is sent to the patient 302.

At 804, a mobile application is provided to the patient 302. For example, when the patient 302 receives the scanning device 102, the patient is instructed to download the mobile application 600 in order to properly use the scanning device 102.

At 806, the patient is directed to use the scanning device 102 with the mobile application 600. For example, as shown in FIGS. 9-20, the mobile application 600 provides step-by-step instructions to the patient 302 on how to properly scan teeth. The mobile application 600 also provides feedback from the scanning device 102 regarding the acceptability of the scan.

At 808, data from the scanning device 102 is received via the mobile device 122. For example, when the scan is complete, the scanning device 102 provides the image data to the mobile device 122, and the mobile device 122 provides the image data to the cloud server 142. In some embodiments, the image data is provided to the cloud server 142 in batches (e.g., after one quadrant of teeth is scanned) instead of after all teeth have been scanned.

At 810, a treatment plan is determined based on the image data. For example, the aligner fabrication computer system 164 compares the scanned images to images of an ideal smile and determines the number of aligners required to move the teeth of the patient 302 to match the ideal smile. The aligner fabrication computer system 164 further determines the geometry of each aligner such that the aligners can be manufactured.

At 812, the aligners are manufactured. For example, the 3D model creation circuit 172 generates a physical 3D model for each aligner determined by the aligner fabrication computer system 164, and the aligners are created via the thermoforming machine 176, the cutting machine 178, and the laser etching machine 180, as described.

Figure 23:
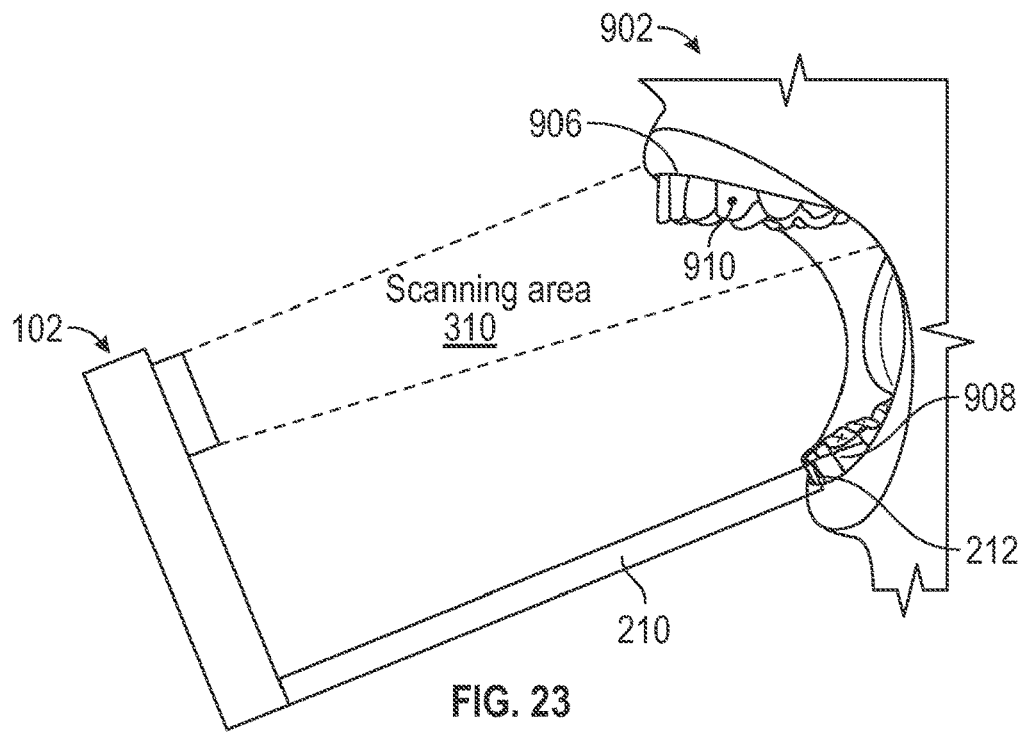
FIG. 23 is an illustration of a user scanning teeth for teledentistry purposes using the scanning device of FIG. 2, according to some embodiments.

Referring to FIG. 23, an illustration of a user scanning teeth for teledentistry purposes using the scanning device 102 of FIG. 2 is shown, according to some embodiments. As used herein, the term "teledentistry" refers to the use of information technology and telecommunications for dental consultation, diagnosis, and treatment planning. As shown, a user 902 has upper teeth 906 and lower teeth 908. Upper teeth 908 includes a cavity 910. The user 902 may be located in an area where access to dental care is difficult, or the user 902 may not be able to travel to a dental practitioner for a checkup, or the user 902 may otherwise find it difficult or impossible to visit in person with a dental practitioner. In such instances, the user 902 can use the scanning device 102 as described to scan the upper teeth 906 and the lower teeth 908 and provide the data to a dental practitioner using the mobile device 122 wirelessly coupled to the scanning device 102.

During the scan, the scanning device 102 may determine that the upper teeth 906 or the lower teeth 908 include dental conditions that require intervention or additional care. For example, the scanning device 102 may find that the user 902 has a cavity 910 on the upper teeth 906. In addition to finding the cavity 910, the scanning device 102 is capable of finding and diagnosing other dental conditions including, but not limited to, cracked teeth, broken crowns, gingivitis, and other dental issues that may require intervention or additional care.

In some embodiments, the scanning device 102 makes determinations about dental conditions that require intervention or care, as described. In some embodiments, the scanning device 102 provides the scan data to the mobile device 122 and the mobile device makes determinations about dental conditions that require intervention or care. In some embodiments, the mobile device 122 communicates with the cloud server 142, which communicates with a teledentistry center, and the cloud server 142 or the teledentistry center makes determinations about dental conditions that require intervention or care. In some embodiments, a combination of two or more of the scanning device 102, the mobile device 122, the cloud server 142, and the teledentistry center make determinations about dental conditions that require intervention or care.

Figure 24:
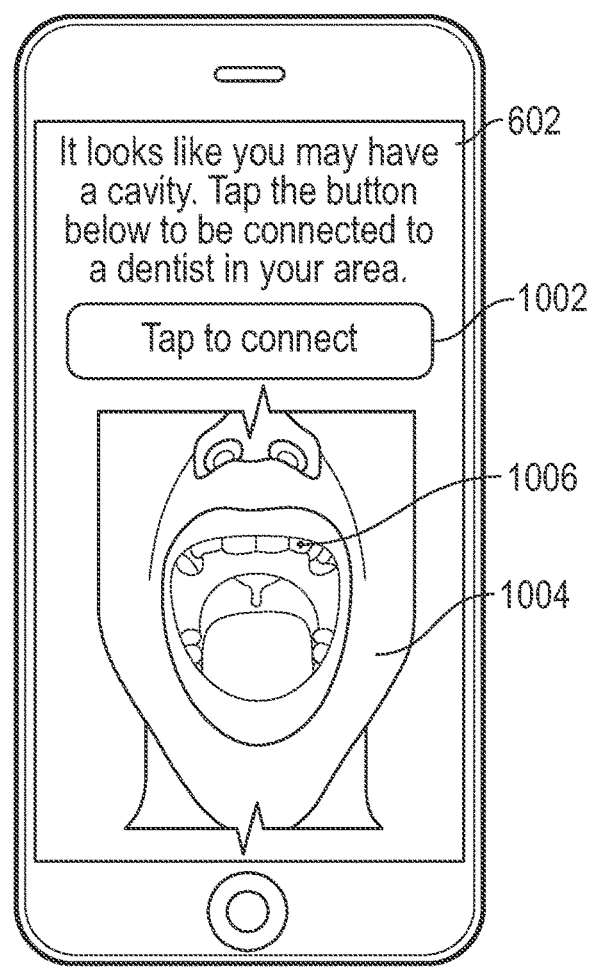
FIG. 24 is an illustration of a mobile device application notifying a patient of a dental condition, according to some embodiments.

Referring to FIG. 24, an illustration of the mobile device application 600 notifying a patient of a dental condition is shown, according to some embodiments. After a determination of a dental condition is determined, the user 902 is notified of the condition on the display 602 of the mobile device 122. In the case where the user 902 has a cavity, the display 602 will display the message 1002 indicating that the user 902 has a cavity. The location of the cavity is indicated in an image 1004 that indicates a highlighted portion 1006 showing where the cavity is located. In some embodiments, the user 902 can be connected directly to a dental practitioner that can provide additional assistance to the user 902. For example, the dental practitioner may provide the user 902 with information as to how to manage the cavity until the user 902 can go to a practitioner to fix the cavity. In cases where intervention is not immediately necessary, the display 602 may provide other messages to help the user manage the dental condition. For example, if a determination is made that the user 902 has receding gums, the display 602 may display a message to the user 902 as to how to care for the receding gums to prevent the condition from worsening. The user may also be able to connect to a dental practitioner to provide additional assistance with managing the condition.

Figure 25:
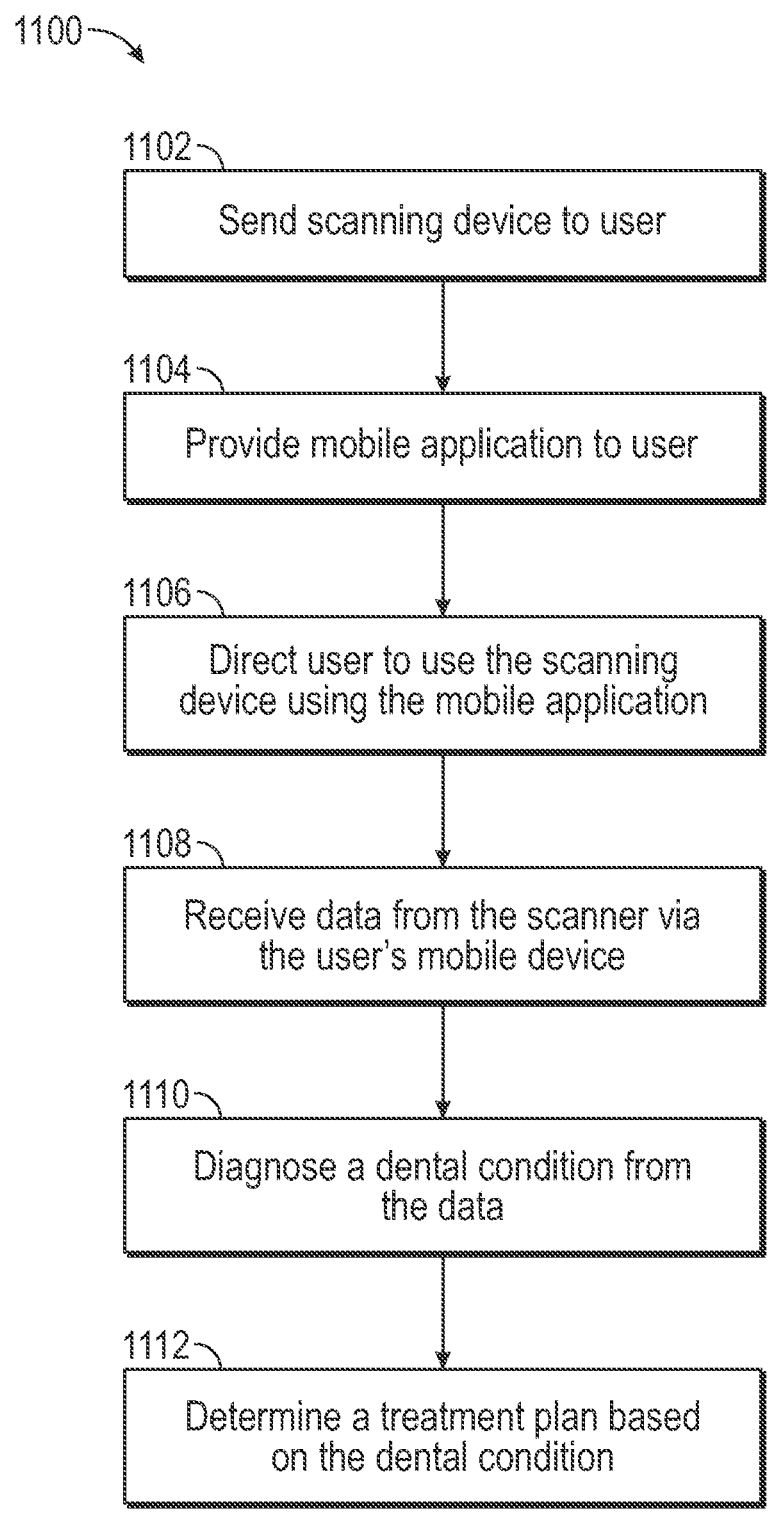
FIG. 25 is a flow diagram of a method for diagnosing a dental condition using the scanning device of FIG. 2, according to some embodiments.

Referring to FIG. 25, a flow diagram of a method 1100 for diagnosing a dental condition using the scanning device 102 of FIG. 2 is shown, according to some embodiments. At 1102, a scanning device is sent to a user. For example, the scanning device 102 is sent to the user 902.

At 1104, a mobile application is provided to the user 902. For example, when the user 902 receives the scanning device 102, the patient is instructed to download the mobile application 600 to use the scanning device 102 properly.

At 1106, the patient is directed to use the scanning device 102 with the mobile application 600. For example, as shown in FIGS. 9-20, the mobile application 600 provides step-by-step instructions to the patient 302 on how to properly scan teeth. The mobile application 600 also provides feedback from the scanning device 102 regarding the acceptability of the scan. Though the description of FIGS. 9-20 focused on using the scanning device 102 to create aligners, the scanning process for teledentistry purposes is the same as for creating aligners.

At 1108, data from the scanning device 102 is received via the mobile device 122. For example, when the scan is complete, the scanning device 102 provides the image data to the mobile device 122, and the mobile device 122 provides the image data to the cloud server 142 for analysis. As described, in some embodiments the analysis of scanned images is completed by one or more of the scanning device 102, the mobile device 122, the cloud server 142, and a teledentistry center.

At 1110, a dental condition is diagnosed from the data. For example, after receiving the image data from the scan, a determination is made that the user 902 has a cavity or some other dental condition (e.g., receding gumline, gingivitis, broken tooth, etc.).

At 1112, a treatment plan is determined based on the dental condition. For example, the user 902 may have a receding gumline. The display 602 may provide the user with instructions as to how to prevent the receding gumline from worsening. The user 902 may also be connected to a dental practitioner through the mobile application 600 such that the dental practitioner can provide the user 902 with advice as to how to care for the dental condition. As another example, the user 902 may have a cracked tooth. The display 602 may provide the user 902 with instructions as to how to perform a temporary repair, and also connect the user 902 with a dental practitioner near the user 902 such that the dental practitioner can fix the problem in a more permanent fashion.

The embodiments described herein refer to scanning teeth to provide for 3D models from which aligners can be constructed for orthodontic treatment. In other embodiments, the scanning device 102 can be used for other dental or orthodontic purposes. For example, the scanning device 102 can be used to provide images to determine the oral health of a patient (e.g., to detect gum disease, cavities, cracked teeth or crowns, and other dental health concerns). Additionally, the scanning device 102 can be used during orthodontic treatment to determine, for example, whether an aligner fits properly, whether an orthodontic change has occurred since starting treatment, whether the patient has regressed, and other orthodontic concerns. Furthermore, the scanning device 102 can be used to determine whether an orthodontic correction is required while the user is adhering to a treatment plan (e.g., a mid-course correction and/or refinement). The scanning device 102 can also be used to provide information to a dental and/or orthodontic professional for regular check-ups. In some instances, the dental and/or orthodontic professional can use the information from the scanning device 102 to determine whether the user needs to travel to the office of the dental and/or orthodontic professional for additional care.

Figure 26A:
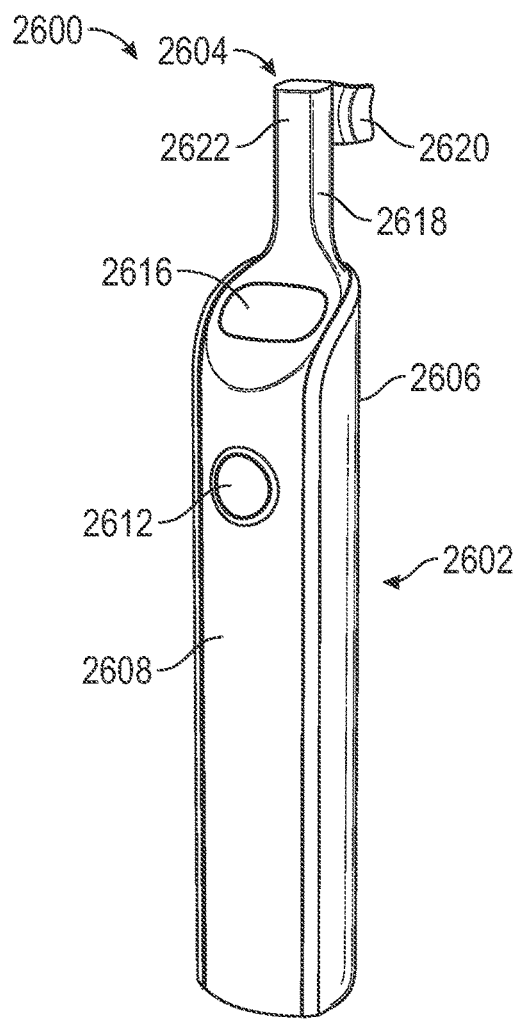
FIGS. 26A-B are illustrations of various views of a scanning device, according to some embodiments.
Figure 26B:
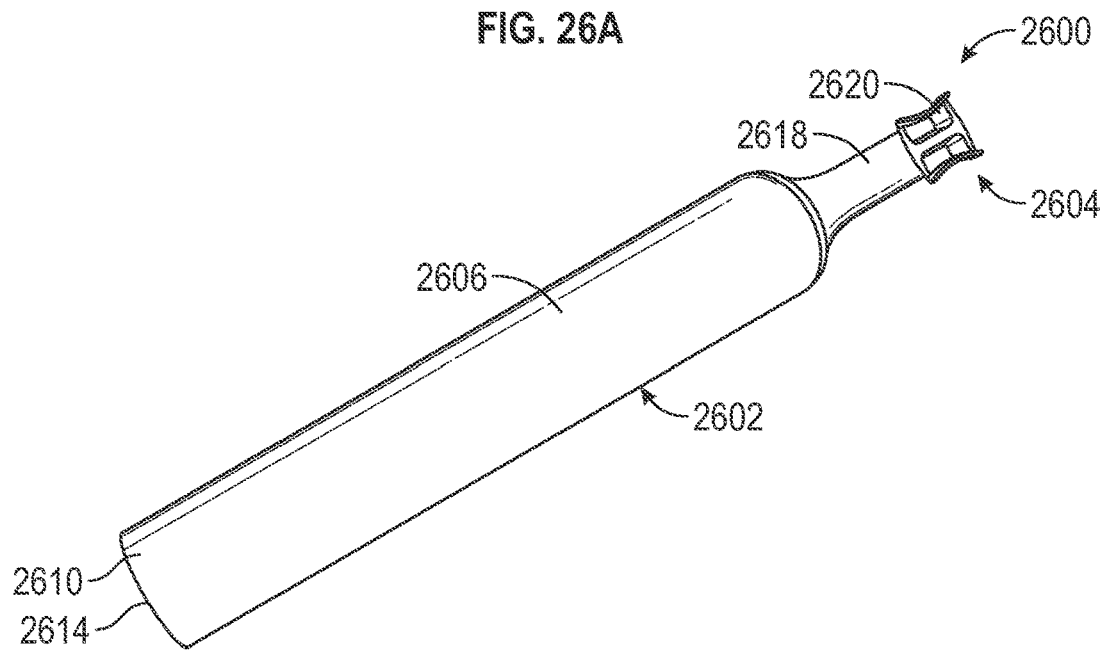

Referring to FIGS. 26A-B, illustrations of various views of a scanning device 2600 is shown, according to some embodiments. The scanning device 2600 can be similar to the scanning device 102. For example, the scanning device 2600 can include non-contact active 3D scanners (e.g., time-of-flight, triangulation, conoscopic holography, or any other kind of non-contact active 3D scanner), hand held laser 3D scanners, structured light 3D scanners, modulated light 3D scanners, and non-contact passive 3D scanners (e.g., stereoscopic, photometric, silhouette, or any other kind of non-contact passive 3D scanner).

Additionally, the scanning device 2600 can include a processing circuit substantially similar to the processing circuit 104, a scanning circuit substantially similar to the scanning circuit 110, a communications circuit substantially similar to the communications circuit 112, a machine learning circuit substantially similar to the machine learning circuit 114, and an analysis circuit substantially similar to the analysis circuit 116.

The scanning device 2600 includes a body 2602 and a guide portion 2604. The body 2602 includes a first body portion 2606, a second body portion 2608, a base body portion 2610, a button 2612, an electrical connection 2614, and a lens 2616. The guide portion 2604 includes a stem 2618, a guide 2620, and a coupler 2622.

The first body portion 2606, the second body portion 2608, and the base body portion 2610 can be manufactured from any material suitable for use in a scanning device. Examples of suitable materials include, but are not limited to, plastics (e.g., acrylonitrile butadiene styrene (ABS), polyurethane, polycarbonate, etc.), metals (e.g., aluminum, stainless steel, etc.), or any combination thereof. In some embodiments, the base body portion 2610 and the second body portion 2608 are of unitary construction. In some embodiments, the base body portion 2610 and the second body portion 2608 are separate components. The second body portion 2608, the first body portion 2606, and the base body portion 2610 can be coupled by any suitable method to form the body 2602. Suitable methods include, but are not limited to, physical connections (e.g., screws, rivets, bolts, etc.), chemical connections (e.g., adhesives, etc.), and designed connections (e.g., press fit, snap fit, etc.).

The body 2602 is configured to contain the components described above (e.g., the processing circuit, the scanning circuit, the communications circuit, the machine learning circuit, and the analysis circuit). In some embodiments, the components described above may be included on a printed circuit board (PCB). In some embodiments, the components described above may be included as separate components. The body 2602 may also be configured to contain additional components. For example, the body 2602 may be configured to contain a haptic motor, a battery, a sealing component, and optics, which will be further described with reference to FIG. 26C.

The base body portion 2610 may be constructed from the same materials as the second body portion 2608 and the first body portion 2606, and includes the electrical connection 2614. The electrical connection 2614 is recessed within the base body portion 2610 and includes electrical components electrically coupled to the battery such that the battery can be recharged when the electrical connection 2614 is coupled to a power source. The electrical connection 2614 can be any type of conventional electrical connection. For example, the electrical connection 2614 can be a USB connection (e.g., USB-A, USB-B, USB-C, mini-USB, micro-USB, Lightning). The electrical connection 2614 can also be any other type of connection configured to couple to a power source and receive power to charge a battery.

The button 2612 is disposed on, or within, the second body portion 2608. In some embodiments, the button 2612 is flush with an outer surface of the second body portion 2608. In some embodiments, the button 2612 protrudes above the outer surface of the second body portion 2608. In some embodiments, the button 2612 is recessed below the outer surface of the second body portion 2608. The button 2612 is configured to actuate the electrical connection between the battery and the other components located within the body 2602. For example, when the scanning device 2600 is off, the electrical connection between the battery and the other components is open. When the user desires to turn on the scanning device 2600, the user depresses the button 2612, which closes the connection between the battery and the other components such that the other components draw power from the battery, and the scanning device 2600 turns on.

The lens 2616 is disposed on, or within the second body portion 2608, and is situated between the optics and the scanning target. For example, the scanning target may be a set of teeth. When the scanning device 2600 is oriented such that the optics are pointed at the set of teeth, the lens is positioned between the optics and the set of teeth. In some embodiments, the lens may be formed to a desired shape by grinding, polishing, or molding processes. In some embodiments, the lens 2616 is configured to focus the optics on the scanning target such that the image of the scanning target is clear. In some embodiments, the lens 2616 is configured to prevent foreign bodies (e.g., dust, particles, etc.) from entering the scanning device 2600 and does not focus the optics. In such embodiments, the lens 2616 may not include a specific shape but may be a transparent or translucent barrier (e.g., plastic, glass, etc.). The lens can be manufactured from any suitable material, including glass and plastic.

The guide portion 2604 is releasably coupled to the body 2602 and includes a stem 2618, a guide 2620, and a coupler 2622. The guide portion 2604 may be coupled to the body 2602 by any type of releasable connection. Examples of releasable connections include, but are not limited to, magnetic connections, threaded connections, and bayonet connections.

Figure 26C:
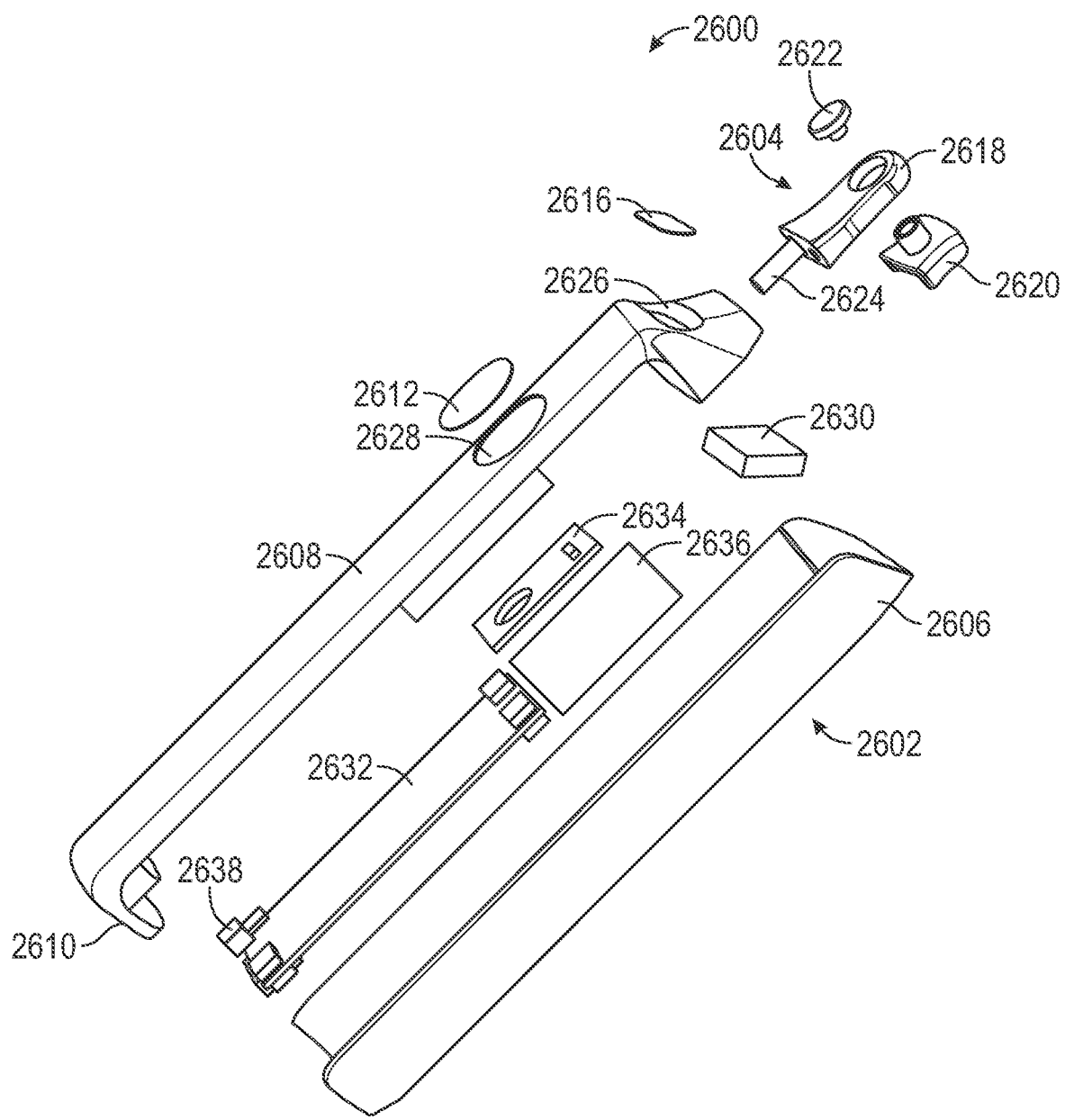
FIG. 26C is an illustration of an exploded view of the scanning device of FIGS. 26A-B.

Referring to FIG. 26C, an illustration of an exploded view of the scanning device 2600 of FIGS. 26A-B is shown. As shown, the stem 2618 extends from the body 2602 and includes a connector 2624 configured to releasably couple the stem 2618 to the second body portion 2608 of the body 2602. The stem 2618 can be manufactured from a material substantially similar to the material of the body 2602, in some embodiments. In some embodiments, the stem 2618 can be manufactured from a different material. The stem 2618 includes a recess to which the coupler 2622 is assembled. The coupler 2622 can be manufactured from a material substantially similar to the material of the stem 2618. The coupler 2622 can also be manufactured from a different material. In some embodiments, the coupler 2622 freely rotates with respect to the stem 2618. In some embodiments, the coupler 2622 is fixed relative to the stem 2618. The coupler 2622 is configured to secure the guide 2620 to the stem 2618. The guide 2620 is configured to receive the teeth of the user when the user is conducting a scan. In embodiments where the coupler 2622 freely rotates with respect to the stem 2618, the guide 2620 may be rigidly coupled to the coupler 2622 such that the guide 2620 rotates as the coupler 2622 rotates. In embodiments where the coupler 2622 is rigidly coupled to the stem 2618, the guide 2620 may freely rotate relative to the coupler 2622. The guide 2620 may include various features configured to aid in scanning a target. Various designs of guides will be further described with reference to FIGS. 33-40.

The second body portion 2608 also includes a lens cavity 2626 and a button cavity 2628. The lens cavity 2626 is sized and configured to receive the lens 2616. The lens 2616 is coupled to the lens cavity 2626 by any suitable coupling mechanism (e.g., adhesive, mechanical, etc.) such that the lens 2616 is rigidly coupled to the lens cavity 2626. The button cavity 2628 is sized and configured to receive the button 2612. In some embodiments, the button 2612 is coupled to the button cavity 2628 such that the button 2612 is movable relative to the button cavity 2628. In some embodiments, the button 2612 is coupled to the button cavity 2628 such that the button 2612 is rigidly connected to the button cavity 2628.

The body 2602 is configured to secure optics 2630, a motherboard 2632, a daughterboard 2634, a battery 2636, and a haptic motor 2638. The body 2602 may also include a sealing component (not shown) positioned between the second body portion 2608 and the first body portion 2606. The optics 2630 may include the first camera 206, the second camera 208, and the projector 207. In some embodiments, first camera 206 and the second camera 208 may include lenses that are fixed such that a focal length defined by the lenses is also fixed. In other embodiments, the first camera 206 and the second camera 208 may include lenses that are movable such that a focal length defined by the lenses is also movable.

In some embodiments, the scanning device 2600 may also include a light source (not shown) to project light on the surface for scanning. In some embodiments, the light source can project visible light on to the surface for scanning. In some embodiments, the light source can project infrared light (or other non-visible light) on to the surface for scanning.

In some embodiments, the scanning device 2600 includes sensors (not shown) to receive light reflected from the surfaces being scanned. In some embodiments, the sensors are configured to receive infrared light (or other non-visible light) reflected from the surfaces being scanned. In some embodiments, the sensors are configured to receive visible light reflected from the surfaces being scanned.

In some embodiments, the scanning device 2600 may include bone scanning technology. Bone scanning technology may include various methods to scan the exterior and interior of a bone. For example, in a dental environment, a bone scan may provide information regarding the internal health of teeth. A bone scan may also provide information regarding the health of the roots of the teeth, or other portions of the teeth that may not be visible such that they can be scanned by a conventional scanning device. In some embodiments, the bone scanning technology enables acquisition of the shape of teeth roots and the position of teeth roots with respect to one another, teeth of the user, or a jawbone of the user.

The motherboard 2632 is electrically coupled to the daughterboard 2634, the battery 2636, the optics 2630, and the haptic motor 2638. The motherboard 2632 may include a processor and a memory. In some embodiments, the processor can be any type of processor capable of performing the functions described herein. The processor may be a single or multi-core processor(s), digital signal processor, microcontroller, or other processor or processing/controlling circuit. Similarly, the memory can be any type of volatile or non-volatile memory or data storage capable of performing the functions described herein. In operation, the memory may store various data and software used during operation of the scanning device 2600, such as operating systems, applications, programs, libraries, and drivers. The memory is communicatively coupled to the processor such that the processor can execute files located in the memory.

The daughterboard 2634 is electrically coupled to the motherboard and is configured to expand the functionality of the motherboard 2632. In some embodiments, the daughterboard 2634 includes portions to connect to the optics 2630, the button 2612, and the haptic motor 2638. Arranged in this manner, the daughterboard 2634 serves to reduce the footprint of the components positioned within the body 2602 to reduce the overall size of the scanning device 2602.

The battery 2636 is electrically coupled to the motherboard 2632, the daughterboard 2634, the optics 2630, and the haptic motor 2638, and is operable to provide power to allow the scanning device 2600 to operate. In some embodiments, the battery 2636 is an alkaline battery (e.g., a AA battery, a AAA battery, etc.). In embodiments where the battery 2636 is an alkaline battery, the battery 2636 may be replaced as needed by separating the second body portion 2608 from the first body portion 2606. In some embodiments, the battery 2636 is a rechargeable battery (e.g., a lithium-ion battery, a nickel-cadmium battery, a nickel-metal-hydride battery, etc.). In such embodiments, the battery 2636 can be recharged by connecting the electrical connection 2614 to a power source. The electrical connection 2614 is electrically coupled to the battery 2636. In some embodiments, the battery 2636 is provided partially charged such that a user can complete a number of scans (e.g., 6 scans, 12 scans, 18 scans, etc.) before needing to charge the battery 2636. In some embodiments, the battery 2636 is provided fully charged such that a user can complete a larger number of scans (e.g., 20 scans, 25 scans, 30 scans, etc.) before needing to charge the battery 2636.

The haptic motor 2638 is electrically coupled to the battery 2636, the motherboard 2632, and the daughterboard 2634, and is configured to provide haptic feedback to the user regarding the use of the scanner. For example, the haptic motor may induce a vibration in the scanning device 2600 when the user is holding the scanning device 2600 to notify the user of an event.

The event may include the initiation of a scan, the completion of a scan, an error during scanning, or other events associated with the scanning device 2600.

The sealing component may be positioned between the second body portion 2608 and the first body portion 2606 such that the sealing component prevents fluids from entering the body 2602. In embodiments where the base body portion 2610 is a separate component from the second body portion 2608 and the first body portion 2606, the sealing component may include multiple sealing components between the second body portion 2608, the first body portion 2606, and the base body portion 2610 such that fluid is prevented from entering the body 2602.

Depending on the length of the stem 2618 and other features included in the scanning device 2600, the scanning device 2600 can scan teeth either intraorally or extraorally. For example, the distance between the teeth and the lens 2616 and the teeth is at least partially dependent on the length of the stem 2618. A relatively short stem 2618 may result in the lens being at least partially within the mouth during a scan (e.g., an intraoral scan). A relatively long stem 2618 may result in the lens being outside of the mouth during a scan (e.g., an extraoral scan).

Figure 27A:
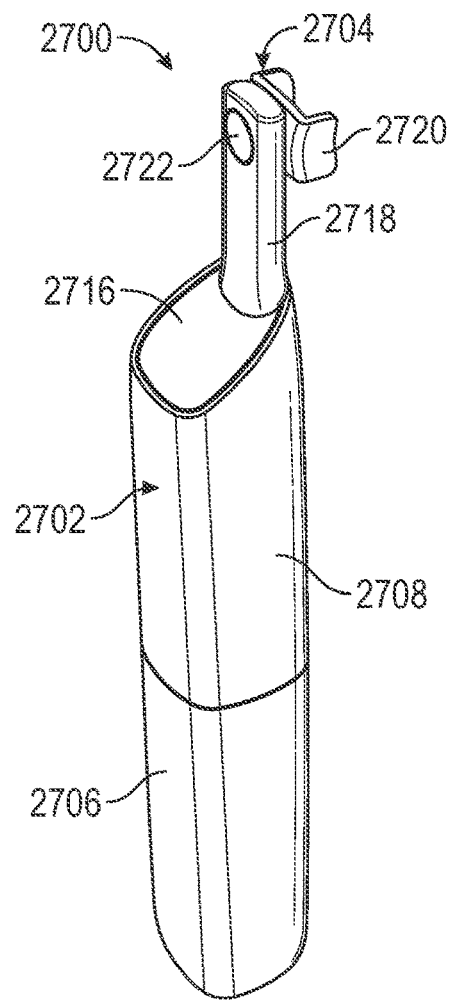
FIGS. 27A-B are illustrations of various views of another scanning device, according to some embodiments.
Figure 27B:
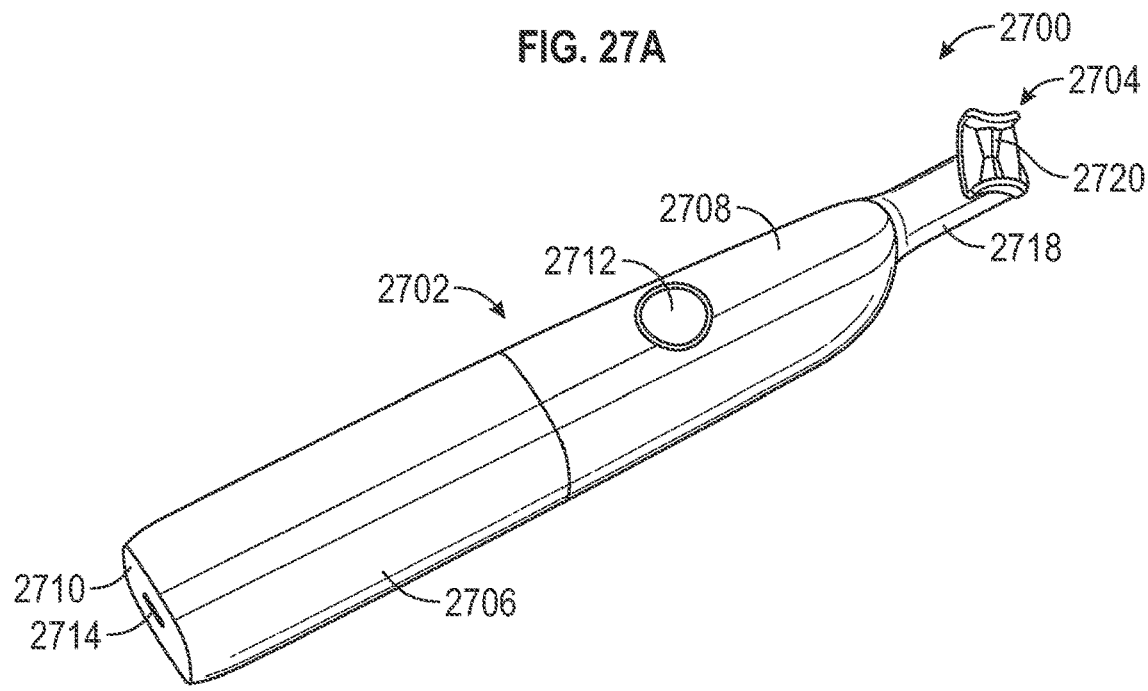

Referring to FIGS. 27A-B, illustrations of various views of another scanning device 2700 are shown, according to some embodiments. The scanning device 2700 can be similar to the scanning device 102. For example, the scanning device 2700 can include non-contact active 3D scanners (e.g., time-of-flight, triangulation, conoscopic holography, or any other kind of non-contact active 3D scanner), hand held laser 3D scanners, structured light 3D scanners, modulated light 3D scanners, and non-contact passive 3D scanners (e.g., stereoscopic, photometric, silhouette, or any other kind of non-contact passive 3D scanner).

Additionally, the scanning device 2700 can include a processing circuit substantially similar to the processing circuit 104, a scanning circuit substantially similar to the scanning circuit 110, a communications circuit substantially similar to the communications circuit 112, a machine learning circuit substantially similar to the machine learning circuit 114, and an analysis circuit substantially similar to the analysis circuit 116.

The scanning device 2700 includes a body 2702 and a guide portion 2704. The body 2702 includes first body portion 2706, a second body portion 2708, a base body portion 2710, a button 2712, an electrical connection 2714, and a lens 2716. The guide portion 2704 includes a stem 2718, a guide 2720, and a coupler 2722.

The first body portion 2706, the second body portion 2708, and the base body portion 2710 can be manufactured from any material suitable for use in a scanning device. Examples of suitable materials include, but are not limited to, plastics (e.g., acrylonitrile butadiene styrene (ABS), polyurethane, polycarbonate, etc.), metals (e.g., aluminum, stainless steel, etc.), or any combination thereof. In some embodiments, the base body portion 2710 and the second body portion 2708 are of unitary construction. In some embodiments, the base body portion 2710 and the second body portion 2708 are separate components. The second body portion 2708, the first body portion 2706, and the base body portion 2710 can be coupled by any suitable method to form the body 2702. Suitable methods include, but are not limited to, physical connections (e.g., screws, rivets, bolts, etc.), chemical connections (e.g., adhesives, etc.), and designed connections (e.g., press fit, snap fit, etc.).

The body 2702 is configured to contain the components described above (e.g., the processing circuit substantially, the scanning circuit, the communications circuit, the machine learning circuit, and the analysis circuit). In some embodiments, the components described above may be included on a printed circuit board (PCB). In some embodiments, the components described above may be included as separate components. The body 2702 may also be configured to contain additional components. For example, the body 2702 may be configured to contain a haptic motor, a battery, a sealing component, and optics, which will be further described with reference to FIG. 27C.

The base body portion 2710 may be constructed from the same materials as the second body portion 2708 and the first body portion 2706, and includes the electrical connection 2714. The electrical connection 2714 is recessed within the base body portion 2710 and includes electrical components electrically coupled to a battery such that the battery can be recharged when the electrical connection 2714 is coupled to a power source. The electrical connection 2714 can be any type of conventional electrical connection. For example, the electrical connection 2614 can be a USB connection (e.g., USB-A, USB-B, USB-C, mini-USB, micro-USB, Lightning). The electrical connection 2714 can also be any other type of connection configured to couple to a power source and receive power to charge a battery.

The button 2712 is disposed on, or within, the second body portion 2708. In some embodiments, the button 2712 is flush with an outer surface of the second body portion 2708. In some embodiments, the button 2712 protrudes above the outer surface of the second body portion 2708. In some embodiments, the button 2712 is recessed below the outer surface of the second body portion 2708. The button 2712 is configured to actuate the electrical connection between the battery and the other components located within the body 2702. For example, when the scanning device 2700 is off, the electrical connection between the battery and the other components is open. When the user desires to turn on the scanning device 2700, the user depresses the button 2712, which closes the connection between the battery and the other components such that the other components draw power from the battery, and the scanning device 2700 turns on.

The lens 2716 is disposed on, or within the second body portion 2708, and is situated between the optics and the scanning target. For example, the scanning target may be a set of teeth. When the scanning device 2700 is oriented such that the optics are pointed at the set of teeth, the lens is positioned between the optics and the set of teeth. In some embodiments, the lens may be formed to a desired shape by grinding, polishing, or molding processes. In some embodiments, the lens 2716 is configured to focus the optics on the scanning target such that the image of the scanning target is clear. In some embodiments, the lens 2716 is configured to prevent foreign bodies (e.g., dust, particles, etc.) from entering the scanning device 2700 and does not focus the optics. In such embodiments, the lens 2616 may not include a specific shape but may be a transparent or translucent barrier (e.g., plastic, glass, etc.) The lens can be manufactured from any suitable material, including glass and plastic.

The guide portion 2704 is releasably coupled to the body 2702 and includes a stem 2718, a guide 2720, and a coupler 2722. The guide portion 2704 may be coupled to the body 2702 by any type of releasable connection. Examples of releasable connections include, but are not limited to, magnetic connections, threaded connections, and bayonet connections.

Figure 27C:
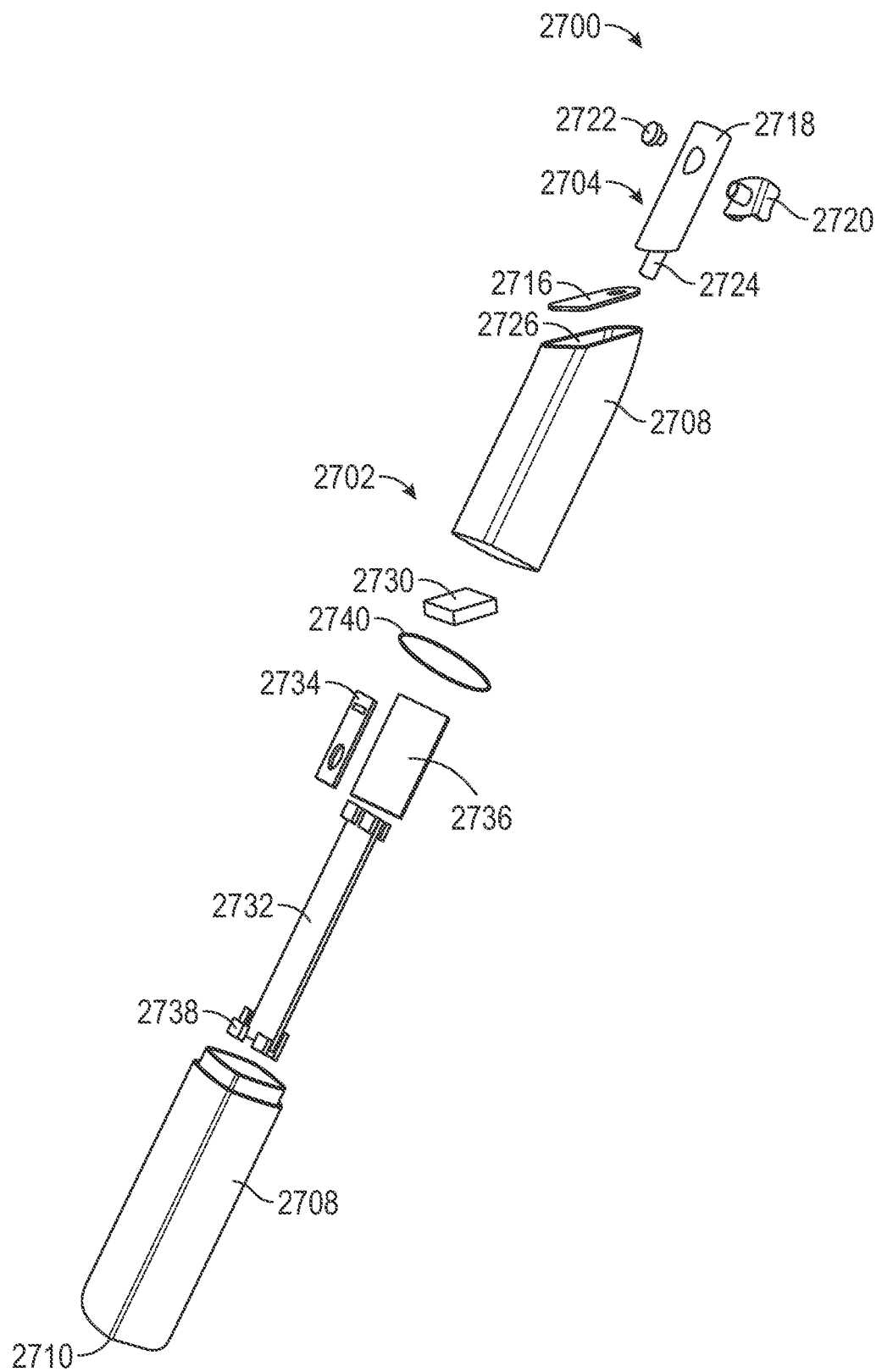
FIG. 27C is an illustration of an exploded view of the scanning device of FIGS. 27A-B.

Referring to FIG. 27C, an illustration of an exploded view of the scanning device 2700 of FIGS. 27 A-B is shown. As shown, the stem 2718 extends from the body 2702 and includes a rod 2724 configured to releasably couple the stem 2718 to the body 2702. The stem 2718 can be manufactured from a material substantially similar to the material of the body 2702, in some embodiments. In some embodiments, the stem 2718 can be manufactured from a different material. The stem 2718 includes a recess (not shown) to which the coupler 2722 is assembled. The coupler 2722 can be manufactured from a material substantially similar to the material of the stem 2718. The coupler 2722 can also be manufactured from a different material. In some embodiments, the coupler 2722 freely rotates with respect to the stem 2718. In some embodiments, the coupler 2722 is fixed relative to the stem 2718. The guide 2720 is configured to receive the teeth of the user when the user is conducting a scan. In embodiments where the coupler 2722 freely rotates with respect to the stem 2718, the guide 2720 may be rigidly coupled to the coupler 2722 such that the guide 2720 rotates as the coupler 2722 rotates. In embodiments where the coupler 2722 is rigidly coupled to the stem 2718, the guide 2720 may freely rotate relative to the coupler 2722. The guide 2720 may include various features configured to aid in scanning a target. Various designs of guides will be further described with reference to FIGS. 33-40.

The second body portion 2708 also includes a lens cavity 2726 and a button cavity 2728. The lens cavity 2726 is sized and configured to receive the lens 2716. The lens 2716 is coupled to the lens cavity 2726 by any suitable coupling mechanism (e.g., adhesive, mechanical, etc.) such that the lens 2716 is rigidly coupled to the lens cavity 2726. The button cavity 2728 is sized and configured to receive the button 2712. In some embodiments, the button 2712 is coupled to the button cavity 2728 such that the button 2712 is movable relative to the button cavity 2728. In some embodiments, the button 2712 is coupled to the button cavity 2728 such that the button 2712 is rigidly connected to the button cavity 2728.

The body 2702 is configured to secure optics 2730, a motherboard 2732, a daughterboard 2734, a battery 2736, and a haptic motor 2738. The body 2702 may also include a sealing component 2740 positioned between the second body portion 2708 and the first body portion 2706. The optics 2730 may include the first camera 206, the second camera 208, and the projector 207. In some embodiments, first camera 206 and the second camera 208 may include lenses that are fixed such that a focal length defined by the lenses is also fixed. In other embodiments, the first camera 206 and the second camera 208 may include lenses that are movable such that a focal length defined by the lenses is also movable.

In some embodiments, the scanning device 2700 may also include a light source (not shown) to project light on the surface to be scanned. In some embodiments, the light source can project visible light on to the surface to be scanned. In some embodiments, the light source can project infrared light (or other non-visible light) on to the surface to be scanned.

In some embodiments, the scanning device 2700 includes sensors (not shown) to receive light reflected from the surfaces being scanned. In some embodiments, the sensors are configured to receive infrared light (or other non-visible light) reflected from the surfaces being scanned. In some embodiments, the sensors are configured to receive visible light reflected from the surfaces being scanned.

In some embodiments, the scanning device 2700 may include bone scanning technology. Bone scanning technology may include various methods to scan the exterior and interior of a bone. For example, in a dental environment, a bone scan may provide information regarding the internal health of teeth. A bone scan may also provide information regarding the health of the roots of the teeth, or other portions of the teeth that may not be visible such that they can be scanned by a conventional scanning device. In some embodiments, the bone scanning technology enables acquisition of the shape of teeth roots and the position of teeth roots with respect to one another, teeth of the user, or a jawbone of the user.

The motherboard 2732 is electrically coupled to the daughterboard 2734, the battery 2736, the optics 2730, and the haptic motor 2738. The motherboard 2732 may include a processor and a memory. In some embodiments, the processor can be any type of processor capable of performing the functions described herein. The processor may be a single or multi-core processor(s), digital signal processor, microcontroller, or other processor or processing/controlling circuit. Similarly, the memory can be any type of volatile or non-volatile memory or data storage capable of performing the functions described herein. In operation, the memory may store various data and software used during operation of the scanning device 2700, such as operating systems, applications, programs, libraries, and drivers. The memory is communicatively coupled to the processor such that the processor can execute files located in the memory.

The daughterboard 2734 is electrically coupled to the motherboard and is configured to expand the functionality of the motherboard 2732. In some embodiments, the daughterboard 2734 includes portions to connect to the optics 2730, the button 2712, and the haptic motor 2738. Arranged in this manner, the daughterboard 2734 serves to reduce the footprint of the components positioned within the body 2702 to reduce the overall size of the scanning device 2702.

The battery 2736 is electrically coupled to the motherboard 2732, the daughterboard 2734, the optics 2730, and the haptic motor 2738, and is operable to provide power to allow the scanning device 2700 to operate. In some embodiments, the battery 2736 is an alkaline battery (e.g., a AA battery, a AAA battery, etc.). In embodiments where the battery 2736 is an alkaline battery, the battery 2736 may be replaced as needed by separating the second body portion 2708 from the first body portion 2706. In some embodiments, the battery 2736 is a rechargeable battery (e.g., a lithium-ion battery, a nickel-cadmium battery, a nickel-metal-hydride battery, etc.). In such embodiments, the battery 2736 can be recharged by connecting the electrical connection 2714 to a power source. The electrical connection 2714 is electrically coupled to the battery 2736. In some embodiments, the battery 2736 is provided partially charged such that a user can complete a number of scans (e.g., 6 scans, 12 scans, 18 scans, etc.) before needing to charge the battery 2736. In some embodiments, the battery 2736 is provided fully charged such that a user can complete a larger number of scans (e.g., 20 scans, 25 scans, 30 scans, etc.) before needing to charge the battery 2736.

The haptic motor 2738 is electrically coupled to the battery 2736, the motherboard 2732, and the daughterboard 2734, and is configured to provide haptic feedback to the user regarding the use of the scanner. For example, the haptic motor may induce a vibration in the scanning device 2700 when the user is holding the scanning device 2700 to notify the user of an event. The event may include the initiation of a scan, the completion of a scan, an error during scanning, or other events associated with the scanning device 2700.

The sealing component 2740 may be positioned between the second body portion 2708 and the first body portion 2706 such that the sealing component prevents fluids from entering the body 2702. In embodiments where the base body portion 2710 is a separate component from the second body portion 2708 and the first body portion 2706, the sealing component may include multiple sealing components 2740 between the second body portion 2708, the first body portion 2706, and the base body portion 2710 such that fluid is prevented from entering the body 2702.

Depending on the length of the stem 2718 and other features included in the scanning device 2700, the scanning device 2700 can scan teeth either intraorally or extraorally. For example, the distance between the teeth and the lens 2716 and the teeth is at least partially dependent on the length of the stem 2718. A relatively short stem 2718 may result in the lens being at least partially within the mouth during a scan (e.g., an intraoral scan). A relatively long stem 2718 may result in the lens being outside of the mouth during a scan (e.g., an extraoral scan).

Figure 28A:
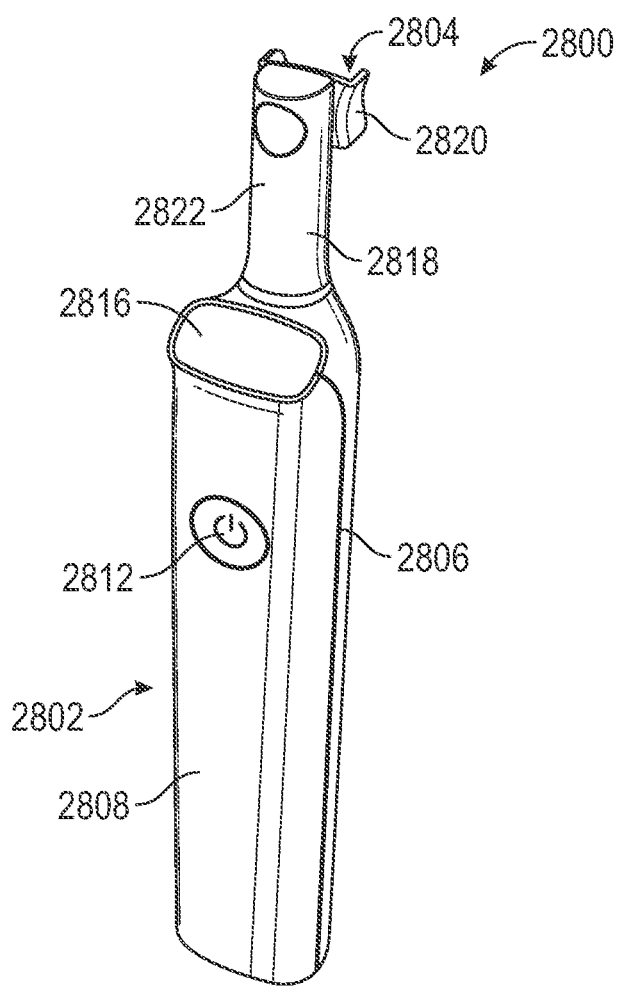
FIGS. 28A-B are illustrations of various views of another scanning device, according to some embodiments.
Figure 28B:
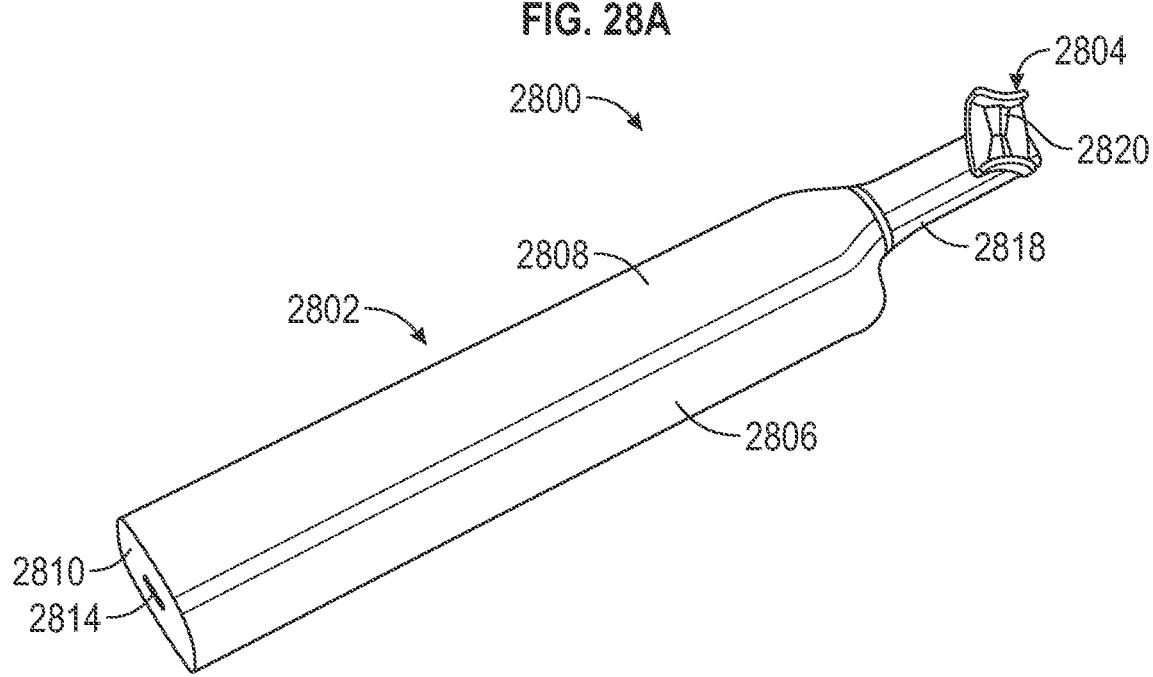

Referring to FIGS. 28A-B, illustrations of various views of another scanning device 2800 are shown, according to some embodiments. The scanning device 2800 can be similar to the scanning device 102. For example, the scanning device 2800 can include non-contact active 3D scanners (e.g., time-of-flight, triangulation, conoscopic holography, or any other kind of non-contact active 3D scanner), hand held laser 3D scanners, structured light 3D scanners, modulated light 3D scanners, and non-contact passive 3D scanners (e.g., stereoscopic, photometric, silhouette, or any other kind of non-contact passive 3D scanner).

Additionally, the scanning device 2800 can include a processing circuit substantially similar to the processing circuit 104, a scanning circuit substantially similar to the scanning circuit 110, a communications circuit substantially similar to the communications circuit 112, a machine learning circuit substantially similar to the machine learning circuit 114, and an analysis circuit substantially similar to the analysis circuit 116.

The scanning device 2800 includes a body 2802 and a guide portion 2804. The body 2802 includes first body portion 2806, a second body portion 2808, a base body portion 2810, a button 2812, an electrical connection 2814, and a lens 2816. The guide portion 2804 includes a stem 2818, a guide 2820, and a coupler 2822.

The first body portion 2806, the second body portion 2808, and the base body portion 2810 can be manufactured from any material suitable for use in a scanning device. Examples of suitable materials include, but are not limited to, plastics (e.g., acrylonitrile butadiene styrene (ABS), polyurethane, polycarbonate, etc.), metals (e.g., aluminum, stainless steel, etc.), or any combination thereof. In some embodiments, the base body portion 2810 and the second body portion 2808 are of unitary construction. In some embodiments, the base body portion 2810 and the second body portion 2808 are separate components. The second body portion 2808, the first body portion 2806, and the base body portion 2810 can be coupled by any suitable method to form the body 2802. Suitable methods include, but are not limited to, physical connections (e.g., screws, rivets, bolts, etc.), chemical connections (e.g., adhesives, etc.), and designed connections (e.g., press fit, snap fit, etc.).

The body 2802 is configured to contain the components described above (e.g., the processing circuit substantially, the scanning circuit, the communications circuit, the machine learning circuit, and the analysis circuit). In some embodiments, the components described above may be included on a printed circuit board (PCB). In some embodiments, the components described above may be included as separate components. The body 2802 may also be configured to contain additional components. For example, the body 2802 may be configured to contain a haptic motor, a battery, a sealing component, and optics, which will be further described with reference to FIG. 28C.

The haptic motor may be configured to provide haptic feedback to the user regarding the use of the scanner. For example, the haptic motor may induce a vibration in the scanning device 2800 when the user is holding the scanning device 2800 to notify the user of an event. The event may include the initiation of a scan, the completion of a scan, an error during scanning, or other events associated with the scanning device 2800.

The battery is configured to provide power to the scanning device 2800. In some embodiments, the battery is a rechargeable battery that is configured to recharge when the scanning device 2800 is coupled to a power source. In some embodiments, the battery is a disposable battery that can be replaced by separating the second body portion 2808 and the first body portion 2806 such that the battery is exposed and can be removed and replaced with a new battery.

The sealing component may be positioned between the second body portion 2808 and the first body portion 2806 such that the sealing component prevents fluids from entering the body 2802. In embodiments where the base body portion 2810 is a separate component from the second body portion 2808 and the first body portion 2806, the sealing component may include multiple sealing components between the second body portion 2808, the first body portion 2806, and the base body portion 2810 such that fluid is prevented from entering the body 2802.

In some embodiments, the optics component may include the first camera 206, the second camera 208, and the projector 207. In some embodiments, first camera 206 and the second camera 208 may include lenses that are fixed such that a focal length defined by the lenses is also fixed. In other embodiments, the first camera 206 and the second camera 208 may include lenses that are movable such that a focal length defined by the lenses is also movable.

The base body portion 2810 may be constructed from the same materials as the second body portion 2808 and the first body portion 2806, and includes the electrical connection 2814. The electrical connection 2814 is recessed within the base body portion 2810 and includes electrical components electrically coupled to the battery such that the battery can be recharged when the electrical connection 2814 is coupled to a power source. The electrical connection 2814 can be any type of conventional electrical connection. For example, the electrical connection 2814 can be a USB connection (e.g., USB-A, USB-B, USB-C, mini-USB, micro-USB, Lightning). The electrical connection 2814 can also be any other type of connection configured to couple to a power source and receive power to charge a battery.

The button 2812 is disposed on, or within, the second body portion 2808. In some embodiments, the button 2812 is flush with an outer surface of the second body portion 2808. In some embodiments, the button 2812 protrudes above the outer surface of the second body portion 2808. In some embodiments, the button 2812 is recessed below the outer surface of the second body portion 2808. The button 2812 is configured to actuate the electrical connection between the battery and the other components located within the body 2802. For example, when the scanning device 2800 is off, the electrical connection between the battery and the other components is open. When the user desires to turn on the scanning device 2800, the user depresses the button 2812, which closes the connection between the battery and the other components such that the other components draw power from the battery, and the scanning device 2800 turns on.

The lens 2816 is disposed on, or within the second body portion 2808, and is situated between the optics and the scanning target. For example, the scanning target may be a set of teeth. When the scanning device 2800 is oriented such that the optics are pointed at the set of teeth, the lens is positioned between the optics and the set of teeth. In some embodiments, the lens may be formed to a desired shape by grinding, polishing, or molding processes. In some embodiments, the lens 2816 is configured to focus the optics on the scanning target such that the image of the scanning target is clear. In some embodiments, the lens 2816 is configured to prevent foreign particles (e.g., dust, particles, etc.) from entering the scanning device 2800 and does not focus the optics. In such embodiments, the lens 2816 may not include a specific shape but may be a transparent or translucent barrier (e.g., plastic, glass, etc.) The lens can be manufactured from any suitable material, including glass and plastic.

The guide portion 2804 is releasably coupled to the body 2802 and includes a stem 2818, a guide 2820, and a coupler 2822. The guide portion 2804 may be coupled to the body 2802 by any type of releasable connection. Examples of releasable connections include, but are not limited to, magnetic connections, threaded connections, and bayonet connections.

Figure 28C:
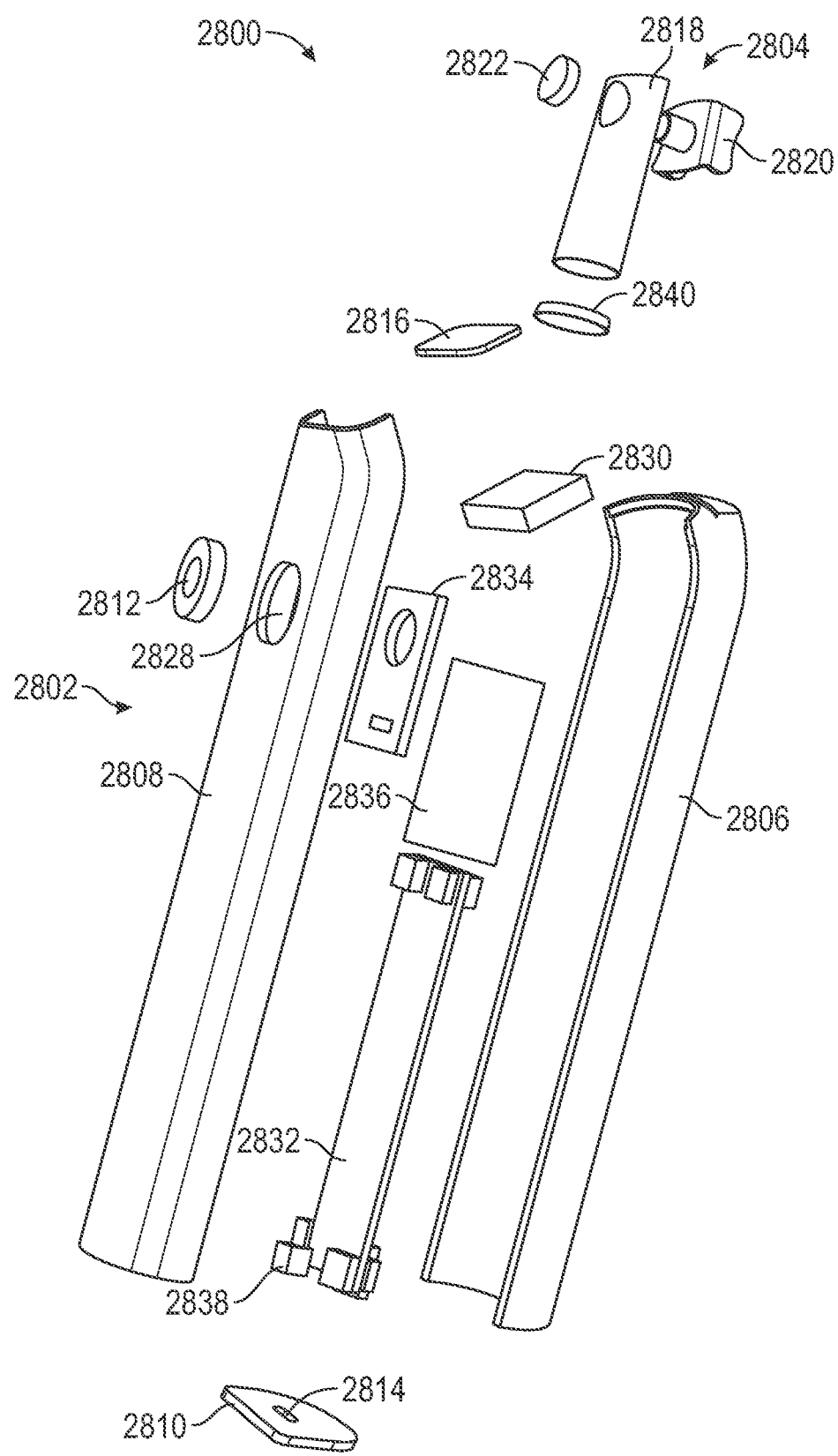
FIG. 28C is an illustration of an exploded view of the scanning device of FIGS. 28A-B.

Referring to FIG. 28C, an illustration of an exploded view of the scanning device 2800 of FIGS. 28A-B is shown. As shown, the stem 2818 extends from the body 2802 and includes a rod 2824 configured to releasably couple to the body 2802. The stem 2818 can be manufactured from a material substantially similar to the material of the body 2802, in some embodiments. In some embodiments, the stem 2818 can be manufactured from a different material. The stem 2818 includes a recess (not shown) to which the coupler 2822 is assembled. The coupler 2822 can be manufactured from a material substantially similar to the material of the stem 2818. The coupler 2822 can also be manufactured from a different material. In some embodiments, the coupler 2822 freely rotates with respect to the stem 2818. In some embodiments, the coupler 2822 is fixed relative to the stem 2818. The guide 2820 is configured to receive the teeth of the user when the user is conducting a scan. In embodiments where the coupler 2822 freely rotates with respect to the stem 2818, the guide 2820 may be rigidly coupled to the coupler 2822 such that the guide 2820 rotates as the coupler 2822 rotates. In embodiments where the coupler 2822 is rigidly coupled to the stem 2818, the guide 2820 may freely rotate relative to the coupler 2822. The guide 2820 may include various features configured to aid in scanning a target. Various designs of guides will be further described with reference to FIGS. 33-40.

The second body portion 2808 also includes a lens cavity 2826 and a button cavity 2828. The lens cavity 2826 is sized and configured to receive the lens 2816. The lens 2816 is coupled to the lens cavity 2826 by any suitable coupling mechanism (e.g., adhesive, mechanical, etc.) such that the lens 2816 is rigidly coupled to the lens cavity 2826. The button cavity 2828 is sized and configured to receive the button 2812. In some embodiments, the button 2812 is coupled to the button cavity 2828 such that the button 2812 is movable relative to the button cavity 2828. In some embodiments, the button 2812 is coupled to the button cavity 2828 such that the button 2812 is rigidly connected to the button cavity 2828.

The body 2802 is configured to secure optics 2830, a motherboard 2832, a daughterboard 2834, a battery 2836, and a haptic motor 2838. The body 2802 may also include a disc 2840 positioned between the second body portion 2808 and the first body portion 2806. The optics 2830 may include the first camera 206, the second camera 208, and the projector 207. In some embodiments, first camera 206 and the second camera 208 may include lenses that are fixed such that a focal length defined by the lenses is also fixed. In other embodiments, the first camera 206 and the second camera 208 may include lenses that are movable such that a focal length defined by the lenses is also movable.

In some embodiments, the scanning device 2800 may also include a light source (not shown) to project light on the surface to be scanned. In some embodiments, the light source can project visible light on to the surface to be scanned. In some embodiments, the light source can project infrared light (or other non-visible light) on to the surface to be scanned.

In some embodiments, the scanning device 2800 includes sensors (not shown) to receive light reflected from the surfaces being scanned. In some embodiments, the sensors are configured to receive infrared light (or other non-visible light) reflected from the surfaces being scanned. In some embodiments, the sensors are configured to receive visible light reflected from the surfaces being scanned.

In some embodiments, the scanning device 2800 may include bone scanning technology. Bone scanning technology may include various methods to scan the exterior and interior of a bone. For example, in a dental environment, a bone scan may provide information regarding the internal health of teeth. A bone scan may also provide information regarding the health of the roots of the teeth, or other portions of the teeth that may not be visible such that they can be scanned by a conventional scanning device. In some embodiments, the bone scanning technology enables acquisition of the shape of teeth roots and the position of teeth roots with respect to one another, teeth of the user, or a jawbone of the user.

The motherboard 2832 is electrically coupled to the daughterboard 2834, the battery 2836, the optics 2830, and the haptic motor 2838. The motherboard 2832 may include a processor and a memory. In some embodiments, the processor can be any type of processor capable of performing the functions described herein. The processor may be a single or multi-core processor(s), digital signal processor, microcontroller, or other processor or processing/controlling circuit. Similarly, the memory can be any type of volatile or non-volatile memory or data storage capable of performing the functions described herein. In operation, the memory may store various data and software used during operation of the scanning device 2800, such as operating systems, applications, programs, libraries, and drivers. The memory is communicatively coupled to the processor such that the processor can execute files located in the memory.

The daughterboard 2834 is electrically coupled to the motherboard and is configured to expand the functionality of the motherboard 2832. In some embodiments, the daughterboard 2834 includes portions to connect to the optics 2830, the button 2812, and the haptic motor 2838. Arranged in this manner, the daughterboard 2834 serves to reduce the footprint of the components positioned within the body 2802 to reduce the overall size of the scanning device 2802.

The battery 2836 is electrically coupled to the motherboard 2832, the daughterboard 2834, the optics 2830, and the haptic motor 2838, and is operable to provide power to allow the scanning device 2800 to operate. In some embodiments, the battery 2836 is an alkaline battery (e.g., a AA battery, a AAA battery, etc.). In embodiments where the battery 2836 is an alkaline battery, the battery 2836 may be replaced as needed by separating the second body portion 2808 from the first body portion 2806. In some embodiments, the battery 2836 is a rechargeable battery (e.g., a lithium-ion battery, a nickel-cadmium battery, a nickel-metal-hydride battery, etc.). In such embodiments, the battery 2836 can be recharged by connecting the electrical connection 2814 to a power source. The electrical connection 2814 is electrically coupled to the battery 2836. In some embodiments, the battery 2836 is provided partially charged such that a user can complete a number of scans (e.g., 6 scans, 12 scans, 18 scans, etc.) before needing to charge the battery 2836. In some embodiments, the battery 2836 is provided fully charged such that a user can complete a larger number of scans (e.g., 20 scans, 25 scans, 30 scans, etc.) before needing to charge the battery 2836.

The haptic motor 2838 is electrically coupled to the battery 2836, the motherboard 2832, and the daughterboard 2834, and is configured to provide haptic feedback to the user regarding the use of the scanner. For example, the haptic motor may induce a vibration in the scanning device 2800 when the user is holding the scanning device 2800 to notify the user of an event.

The event may include the initiation of a scan, the completion of a scan, an error during scanning, or other events associated with the scanning device 2800.

The sealing component (not shown) may be positioned between the second body portion 2808 and the first body portion 2806 such that the sealing component prevents fluids from entering the body 2802. In embodiments where the base body portion 2810 is a separate component from the second body portion 2808 and the first body portion 2806, the sealing component may include multiple sealing components between the second body portion 2808, the first body portion 2806, and the base body portion 2810 such that fluid is prevented from entering the body 2802.

A disc 2840 may be positioned between the stem 2818 and the body 2802. In some embodiments, the disc 2840 may be magnetic such that the stem 2818 (which may also be magnetic, in some embodiments), can be releasable coupled to the disc 2840. The disc 2840 may be rigidly coupled to the body 2802 such that, when the stem 2818 is removed from the disc 2840, the disc 2840 remains coupled to the body 2802.

Depending on the length of the stem 2818 and other features included in the scanning device 2800, the scanning device 2800 can scan teeth either intraorally or extraorally. For example, the distance between the teeth and the lens 2816 and the teeth is at least partially dependent on the length of the stem 2818. A relatively short stem 2818 may result in the lens being at least partially within the mouth during a scan (e.g., an intraoral scan). A relatively long stem 2718 may result in the lens being outside of the mouth during a scan (e.g., an extraoral scan).

Referring to FIGS. 29A-B, illustrations of a front and a side view, respectively, of an arrangement of internal components in a scanning device 2920 are shown, according to some embodiments. The scanning device 2920 is a representative scanning device (e.g., the scanning device 2920 may be or include features from any of the scanning device 102, the scanning device 2600, the scanning device 2700, or the scanning device 2800, in various embodiments). The scanning device 2920 includes a body 2922 and a guide portion 2924. The body 2922 is a representative body (e.g., the body 2922 may be any of the body 202, the body 2602, the body 2702, or the body 2802, in various embodiments). The guide portion 2924 is a representative guide portion (e.g., the guide portion 2924 may be any of the guide portion 212, the guide portion 2604, the guide portion 2704, or the guide portion 2804, in various embodiments). As shown, the scanning device 2920 is oriented vertically. Accordingly, the "top" of the scanning device 2920 refers to portions of the scanning device 2920 closer to the guide portion 2924, and the "bottom" of the scanning device 2920 refers to portions of the scanning device 2920 further from the guide portion 2924.

The body 2922 is shown to enclose optics 2926, a motherboard 2928, a daughterboard 2930, and a battery 2932. The optics 2926, the motherboard 2928, the daughterboard 2930, and the battery 2932 are substantially similar to the similarly named components of FIGS. 26A-C, FIGS. 27A-C, and FIGS. 28A-C. For example, the optics 2926 are substantially similar to the optics 2630, the optics 2730, and the optics 2830. The optics 2926 are located toward the top of the body 2922 and are positioned and an angle 2934 relative to a vertical axis coaxial with the body 2922. The angle 2934 allows the optics 2926 to be oriented toward the teeth of the patient (e.g., the upper teeth or the lower teeth) during a scan of the teeth when the guide portion 2924 is in contact with the teeth of the patient. In some embodiments, the angle 2934 is between 120° and 170°. In some embodiments, the angle 2934 is between 130° and 160°. In some embodiments, the angle 2934 is between 140° and 150°. In some embodiments, the angle 2934 is at least 100°, at least 110°, or at least 120°.

The battery 2932 is positioned toward the bottom of the body 2922 such that no other components are positioned between the battery 2932 and the bottom of the body 2922. The motherboard 2928 and the daughterboard 2930 are positioned between the battery 2932 and the optics 2926.

The motherboard 2928 and the daughterboard 2930 are arranged such that the motherboard 2928 and the daughterboard 2930 are adjacent to each other.

Referring to FIGS. 30A-B, illustrations of a front and a side view, respectively, of another arrangement of internal components in another scanning device are shown, according to some embodiments. The scanning device 2950 is a representative scanning device (e.g., the scanning device 2950 may be any of the scanning device 102, the scanning device 2600, the scanning device 2700, or the scanning device 2800, in various embodiments). The scanning device 2950 includes a body 2952 and a guide portion 2954. The body 2952 is a representative body (e.g., the body 2952 may be any of the body 202, the body 2602, the body 2702, or the body 2802, in various embodiments). The guide portion 2954 is a representative guide portion (e.g., the guide portion 2954 may be any of the guide portion 212, the guide portion 2604, the guide portion 2704, or the guide portion 2804, in various embodiments). As shown, the scanning device 2950 is oriented vertically. Accordingly, the "top" of the scanning device 2950 refers to portions of the scanning device 2950 closer to the guide portion 2954, and the "bottom" of the scanning device 2950 refers to portions of the scanning device 2950 further from the guide portion 2954.

The body 2952 is shown to enclose optics 2956, a motherboard 2958, a daughterboard 2960, a battery 2962, a button 2964, and a haptic motor 2968. The optics 2956, the motherboard 2958, the daughterboard 2960, the battery 2962, the button 2964, and the haptic motor 2968 are substantially similar to the similarly named components of FIGS. 26A-C, FIGS. 27A-C, and FIGS. 28A-C. For example, the optics 2956 are substantially similar to the optics 2630, the optics 2730, and the optics 2830. The optics 2956 are located toward the top of the body 2952 and are positioned and an angle 2966 relative to a vertical axis coaxial with the body 2952. The angle 2966 allows the optics 2956 to be oriented toward the teeth of the patient (e.g., the upper teeth or the lower teeth) during a scan of the teeth when the guide portion 2954 is in contact with the teeth of the patient. In some embodiments, the angle 2966 is between 105° and 155°. In some embodiments, the angle 2954 is between 115° and 145°. In some embodiments, the angle 2954 is between 125° and 135°.

The motherboard 2958 is positioned toward the bottom of the body 2952 such that no other components are positioned between the motherboard 2958 and the bottom of the body 2922. The haptic motor 2968 is positioned adjacent to the motherboard 2958 toward the bottom of the body 2952. The battery 2962 is positioned between the motherboard 2958 and the optics 2956, and is adjacent to the daughterboard 2960. The button 2964 extends from the daughterboard 2960 such that the button 2964 is accessible to a user. In some embodiments, the button 2964 extends through the body 2952 for user access. In some embodiments, the button 2964 is flush with an outer surface of the body 2952 for user access.

Figure 31:
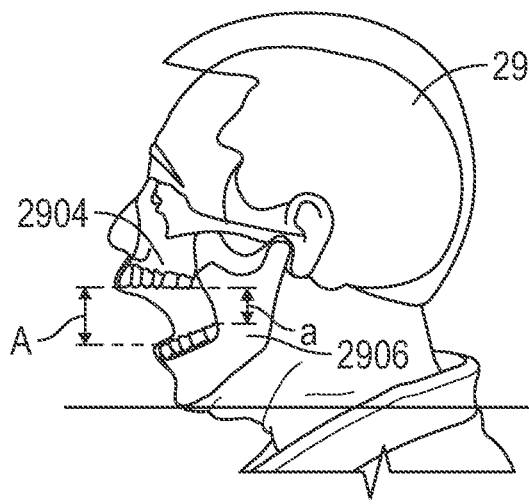
FIG. 31 is an illustration of a jaw separation of a user with no substantial head tilt, according to some embodiments.

Referring to FIG. 31, an illustration of a jaw separation of a user with no substantial head tilt is shown, according to some embodiments. The user's head 2902 is not substantially tilted (e.g., the head 2902 is tilted between −5° and 5°). The user is shown to be opening his mouth such that an upper jaw 2904 and a lower jaw 2906 are separated as much as possible. Without substantially tilting the head 2902, the distance between the back teeth (e.g., molars) is a, and the distance between the front teeth (e.g., incisors) is A, where A is greater than a. For example, in some embodiments a may be 23-33 millimeters (mm) and A may be 45-55 mm.

Figure 32:
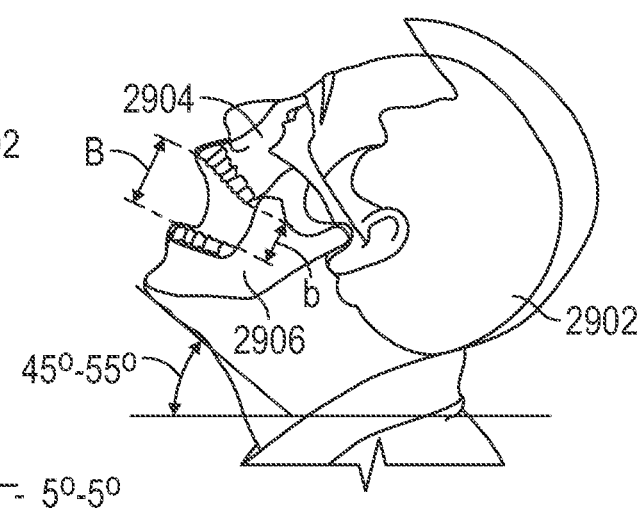
FIG. 32 is an illustration of a jaw separation of a user with a substantial upward head tilt, according to some embodiments.

Referring to FIG. 32, an illustration of a jaw separation of a user with a substantial upward head tilt is shown, according to some embodiments. The user's head 2902 is substantially tilted upward (e.g., the head is tilted between 45° and 55° upward). The user is shown to be opening his mouth such that the upper jaw 2904 and the lower jaw 2906 are separated as much as possible. In this position, the distance between the back teeth is b, and the distance between the front teeth is B, where B is greater than b. For example, in some embodiments b may be 25-35 mm and B may be 50-60 mm.

Figure 33:
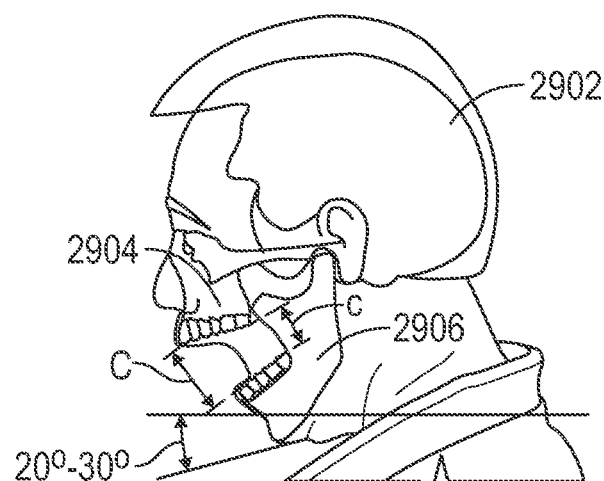
FIG. 33 is an illustration of a jaw separation of a user with a substantial downward head tilt, according to some embodiments.

Referring to FIG. 33, an illustration of a jaw separation of a user with a substantial downward head tilt is shown, according to some embodiments. The user's head 2902 is substantially tilted downward (e.g., the head is tilted between 20° and 30° downward). The user is shown to be opening his mouth such that the upper jaw 2904 and the lower jaw 2906 are separated as much as possible. In this position, the distance between the back teeth is C, and the distance between the front teeth is C, where C is greater than c. For example, in some embodiments c may be 18-28 mm and C may be 33-43 mm.

Figure 34:
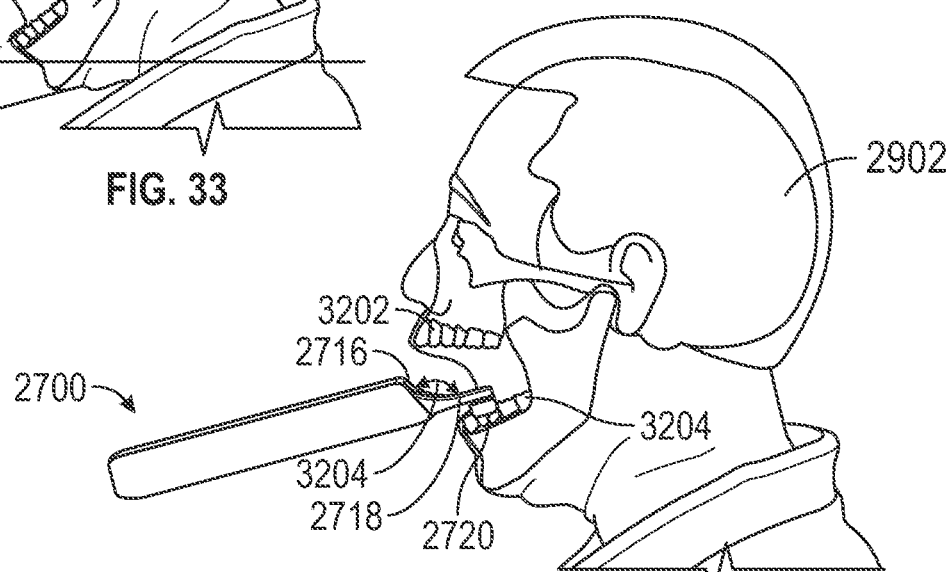
FIG. 34 is an illustration of a scanning device scanning teeth of a user, according to some embodiments.

Referring to FIG. 34, an illustration of the scanning device 2700 scanning teeth of a user is shown, according to some embodiments. The scanning device 2700 is shown as an example embodiment. In other embodiments, the scanning device 2600 or the scanning device 2800 may be used. The guide 2720 is positioned on lower teeth 3204 of the user. In this position, the scanning device scans the upper teeth 3202 as the optics inside the scanning device 2700 scan the upper teeth 3202. An angle 3204 is defined by the angle between the lens 2716 and the stem 2718. The angle 3204 may be substantially similar to the angle 2934 of FIGS. 29A-B or the angle 2966 of FIGS. 30A-B. For example, the angle 3204 may be between 140° and 150°, in some embodiments. In some embodiments, the user scans the upper teeth 3202 by moving the guide 2720 along the lower teeth 3204, and then scans the lower teeth 3204 by moving the guide 2720 along the upper teeth 3202 in a manner similar to that described with reference to FIG. 21.

Figure 35:
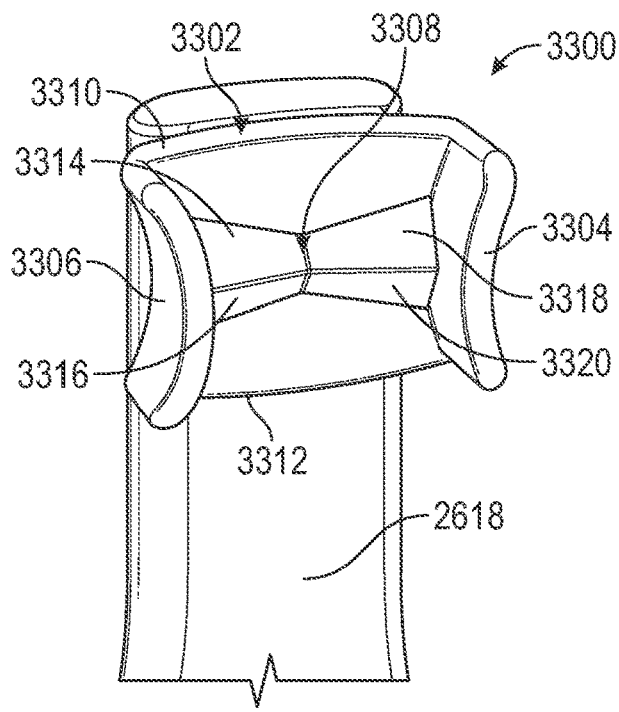
FIG. 35 is an illustration of a guide of a scanning device, according to some embodiments.

Referring to FIG. 35, an illustration of a guide 3300 of a scanning device is shown, according to some embodiments. The guide 3300 could be any of the guide 2620, the guide 2720, or the guide 2820, in various embodiments. Accordingly, reference to the stem 2618 in the description of the guide 3300 is for purposes of explanation only, and is not intended to be limiting. The guide 3300 is coupled to the stem 2618 via the coupler 2622 such that the guide 3300 can rotate relative to the stem 2618. The guide 3300 is configured to contact the teeth of a user and remain in contact with the teeth of the user during a scan of the teeth. Accordingly, the guide 3300 can be manufactured from any material suitable to contact the teeth of the user. Examples of suitable materials include, but are not limited to, various plastics (e.g., thermoplastic polyurethane, polyethylene, acrylonitrile butadiene styrene (ABS)) rubbers, and silicones.

The guide 3300 includes a base 3302 and a boss 3308 protruding from the base 3302. The base 3302 includes a base top 3310 and a base bottom 3312, with the base 3302 extending from the base top 3310 to the base bottom 3312. A first side portion 3304 protrudes from the base 3302 and extends from the base top 3310 to the base bottom 3312. The first side portion 3304 defines a concave shape such that the first side portion curves toward the boss 3308 as the first side portion extends from the base top 3310 toward the boss 3308, and the first side portion curves away from the boss 3308 as the first side portion extends from the boss 3308 toward the base bottom 3312. A second side portion 3306 defines a concave shape such that the second side portion curves toward the boss 3308 as the second side portion extends from the base top 3310 toward the boss 3308, and the second side portion curves away from the boss 3308 as the second side portion extends from the boss 3308 toward the base bottom 3312.

The boss 3308 includes a first protrusion 3314, a second protrusion 3316, a third protrusion 3318, and a fourth protrusion 3320. The first protrusion 3314 protrudes from the base 3302 and the second side portion 3306. The second protrusion 3316 protrudes from the base 3302 and the second side portion 3306. The first protrusion 3314 and the second protrusion 3316 meet at an axis extending across the base 3302 approximately midway between the base top 3310 and the base bottom 3312. The third protrusion 3318 protrudes from the base 3302 and the first side portion 3304. The fourth protrusion 3320 protrudes from the base 3302 and the first side portion 3304. The third protrusion 3318 and the fourth protrusion 3320 meet at the axis extending across the base 3302 approximately midway between the base top 3310 and the base bottom 3312. The first protrusion 3314, the second protrusion 3316, the third protrusion 3318, and the fourth protrusion 3320 meet at an intersection of the axis extending across the base 3302 approximately midway between the base top 3310 and the base bottom 3312 and an axis extending across the base 3302 approximately midway between the first side portion 3304 and the second side portion 3306. Accordingly, the shape of the boss 3308 may be described as a "bow tie" shape.

Figure 36A:
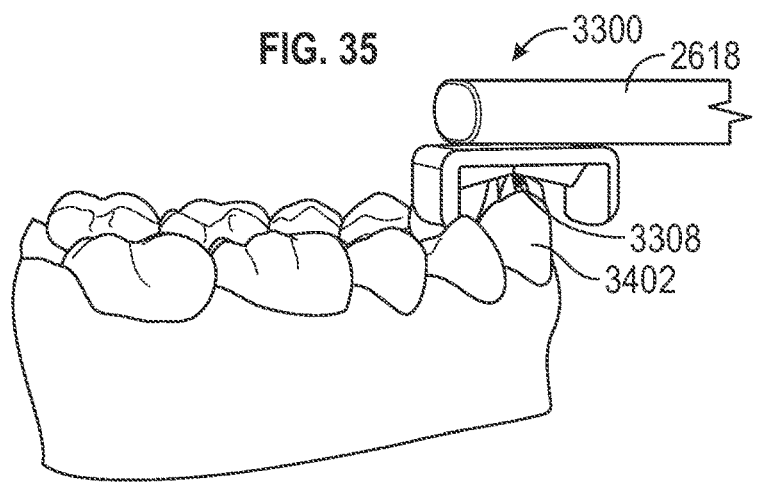
FIGS. 36A-B is an illustration of the guide of FIG. 35 moving over teeth, according to some embodiments.
Figure 36B:
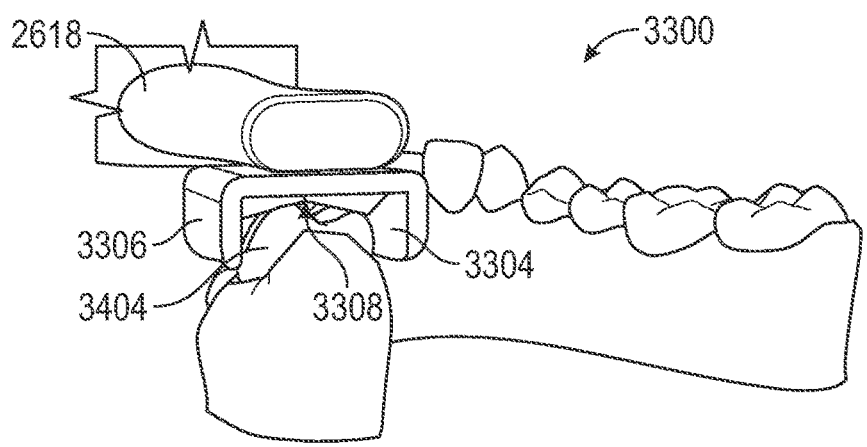

Referring to FIGS. 36A-B, an illustration of the guide 3300 of FIG. 35 moving over teeth is shown, according to some embodiments. The guide 3300 is shown moving over non-molar teeth 3402 (e.g., incisors, canines, or bicuspids) in FIG. 36A, and a central portion of the boss 3308 (e.g., the center of the "bow tie" shape) contacts the non-molar teeth when the guide 3300 is moving over the non-molar teeth 3402. The shape of the boss 3308 directs the teeth within the guide 3300 such that each tooth over which the guide 3300 passes contacts the central portion of the boss 3308.

The guide 3300 is shown moving over molar teeth 3404 in FIG. 36B, and the first side portion 3304 and the second side portion 3306 contact the molar teeth 3404 when the guide 3300 is moving over the molar teeth 3404. The first side portion 3304 and the second side portion 3306 are shaped such that the molar teeth 3404 are centrally located between the first side portion 3304 and the second side portion 3306 during a scan.

Figure 37:
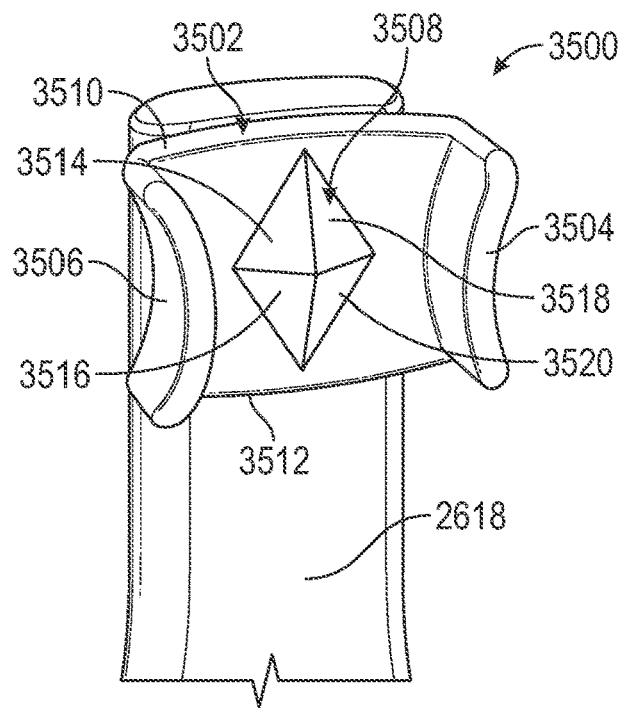
FIG. 37 is an illustration of another guide of a scanning device, according to some embodiments.

Referring to FIG. 37, an illustration of another guide 3500 of a scanning device is shown, according to some embodiments. The guide 3500 could be any of the guide 2620, the guide 2720, or the guide 2820, in various embodiments. Accordingly, reference to the stem 2618 in the description of the guide 3300 is for purposes of explanation only, and is not intended to be limiting. The guide 3500 is coupled to the stem 2618 via the coupler 2622 such that the guide 3500 can rotate relative to the stem 2618. The guide 3500 is configured to contact the teeth of a user and remain in contact with the teeth of the user during a scan of the teeth. Accordingly, the guide 3500 can be manufactured from any material suitable to contact the teeth of the user. Examples of suitable materials include, but are not limited to, various plastics (e.g., thermoplastic polyurethane, polyethylene, acrylonitrile butadiene styrene (ABS)) rubbers, and silicones.

The guide 3500 includes a base 3502 and a boss 3508 protruding from the base 3502. The base 3502 includes a base top 3510 and a base bottom 3512, with the base 3502 extending from the base top 3510 to the base bottom 3512. A first side portion 3504 protrudes from the base 3502 and extends from the base top 3510 to the base bottom 3512. The first side portion 3504 defines a concave shape such that the first side portion curves toward the boss 3508 as the first side portion extends from the base top 3510 toward the boss 3508, and the first side portion curves away from the boss 3508 as the first side portion extends from the boss 3508 toward the base bottom 3512. A second side portion 3506 defines a concave shape such that the second side portion curves toward the boss 3508 as the second side portion extends from the base top 3510 toward the boss 3508, and the second side portion curves away from the boss 3508 as the second side portion extends from the boss 3508 toward the base bottom 3512.

The boss 3508 includes first protrusion 3514, a second protrusion 3516, a third protrusion 3518, and a fourth protrusion 3520. The first protrusion 3514 protrudes from the base 3502 and extends toward the midpoint of the base 3502. The second protrusion 3516 protrudes from the base 3502 and extends toward the midpoint of the base 3502. The third protrusion 3518 protrudes from the base 3502 and extends toward the midpoint of the base 3502, and the fourth protrusion 3520 protrudes from the base 3502 and extends toward the midpoint of the base 3502. The first protrusion 3514, the second protrusion 3516, the third protrusion 3518, and the fourth protrusion 3520 meet at an intersection of an axis extending across the base 3502 approximately midway between the base top 3510 and the base bottom 3512 and an axis extending across the base approximately midway between the first side portion 3504 and the second side portion 3506. Accordingly, the shape of the boss 3508 may be described as a "diamond" or "pyramid" shape, with the apex located along an axis coaxial with an approximate center of the base 3502.

Figure 38A:
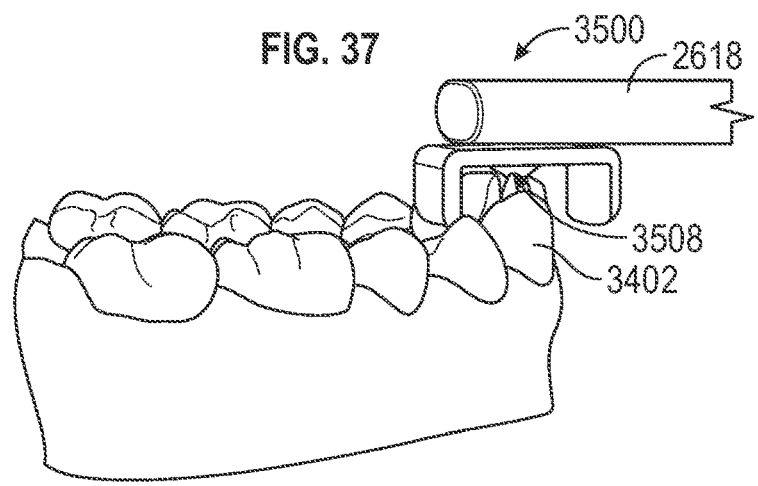
FIGS. 38A-B are illustrations of the guide of FIG. 37 moving over teeth, according to some embodiments.
Figure 38B:
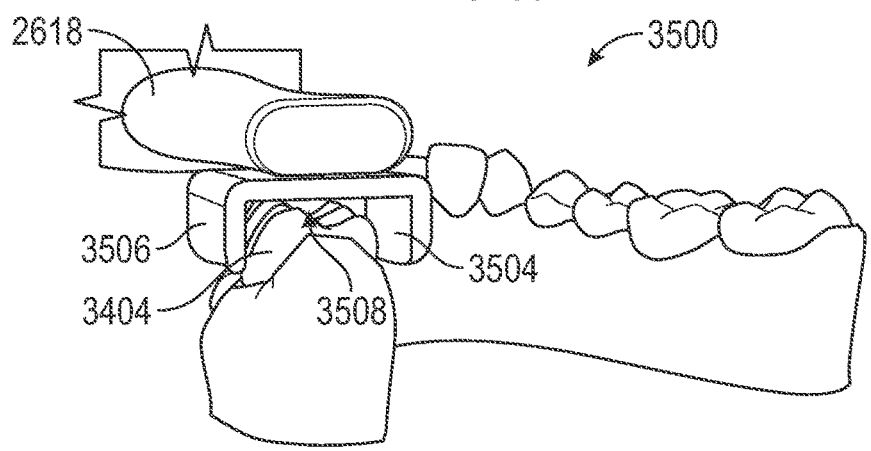

Referring to FIGS. 38A-B, an illustration of the guide 3500 of FIG. 37 moving over teeth is shown, according to some embodiments. The guide 3500 is shown moving over non-molar teeth 3402 (e.g., incisors, canines, or bicuspids) in FIG. 38A, and the apex of the boss 3508 (e.g., the center of the "diamond" or "pyramid" shape) contacts the non-molar teeth 3402 when the guide 3500 is moving over the non-molar teeth 3402. The shape of the boss 3508 directs the teeth within the guide 3500 such that each tooth over which the guide 3500 passes contacts the apex of the boss 3508.

The guide 3500 is shown moving over molar teeth 3404 in FIG. 37B, and the first side portion 3504 and the second side portion 3506 contact the molar teeth 3404 when the guide 3500 is moving over the molar teeth 3404. The first side portion 3504 and the second side portion 3506 are shaped such that the molar teeth 3404 are centrally located between the first side portion 3504 and the second side portion 3506 during a scan.

Figure 39:
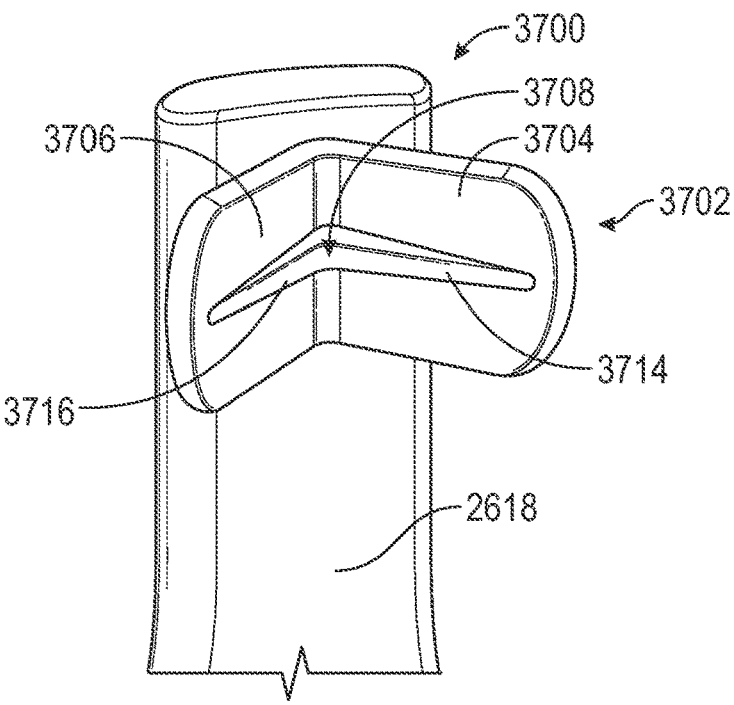
FIG. 39 is an illustration of another guide of a scanning device, according to some embodiments.

Referring to FIG. 39, an illustration of another guide 3700 of a scanning device is shown, according to some embodiments. The guide 3700 could be any of the guide 2620, the guide 2720, or the guide 2820, in various embodiments. Accordingly, reference to the stem 2618 in the description of the guide 3300 is for purposes of explanation only, and is not intended to be limiting. The guide 3700 is coupled to the stem 2618 via the coupler 2622 such that the guide 3500 can rotate relative to the stem 2618. The guide 3700 is configured to contact the teeth of a user and remain in contact with the teeth of the user during a scan of the teeth. Accordingly, the guide 3700 can be manufactured from any material suitable to contact the teeth of the user. Examples of suitable materials include, but are not limited to, various plastics (e.g., thermoplastic polyurethane, polyethylene, acrylonitrile butadiene styrene (ABS)) rubbers, and silicones.

The guide 3700 includes a base 3702 (not shown) rotatably coupled to the stem 2618, and a boss 3708. A first side portion 3704 extends away from the base 3702 at an angle (e.g., 30 degrees, 40 degrees, 50 degrees, etc.). A second side portion 3706 extends away from the base 3702 at an angle opposite the angle of the first side portion 3704 (e.g., −30 degrees, −40 degrees, −50 degrees, etc.). The lengths of the first side portion 3704 and the second side portion 3706 are substantially similar such that the first side portion 3704 and the second side portion 3706 create two sides of an isosceles triangle, with the third side being open to allow the guide 3700 to receive a tooth.

The boss 3708 includes a first protrusion 3714 and a second protrusion 3716. The first protrusion 3714 extends from the first side portion 3704 and away from the stem 2618. The second protrusion 3718 extends from the second side portion 3706 and away from the stem 2618. Both the first protrusion 3714 and the second protrusion 3718 extend from the first side portion 3704 and the second side portion 3706, respectively, such that the first protrusion 3714 and the second protrusion 3716 are thickest where the first protrusion 3714 meets the second protrusion 3716 (e.g., in the approximate center of the guide 3700). The thickness of the first protrusion 3714 decreases as the first protrusion 3714 extends away from the approximate center of the guide 3700. The thickness of the second protrusion 3716 also decreases as the second protrusion 3716 extends away from the approximate center of the guide 3700. In some embodiments, the first protrusion 3714 and the second protrusion 3716 are one continuous protrusion that extends from a center portion of the base 3702 along the first side portion 3704 and the second side portion 3706.

Figure 40A:
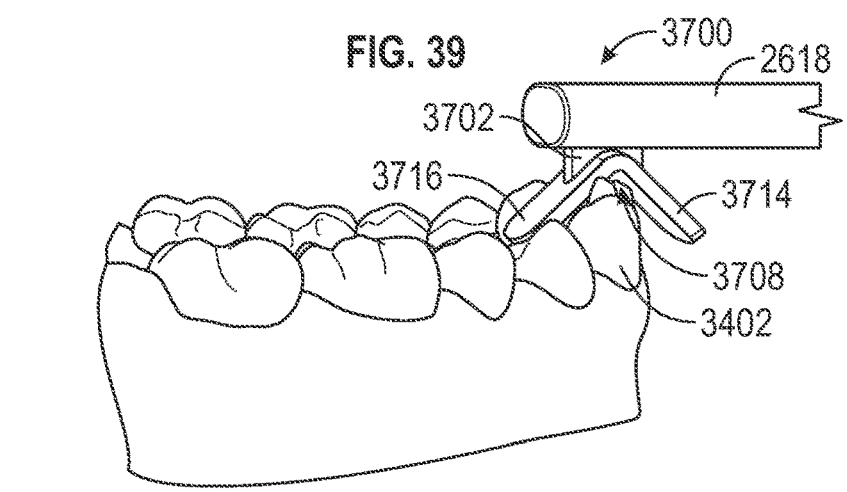
FIGS. 40A-B are illustrations of the guide of FIG. 39 moving over teeth, according to some embodiments.
Figure 40B:
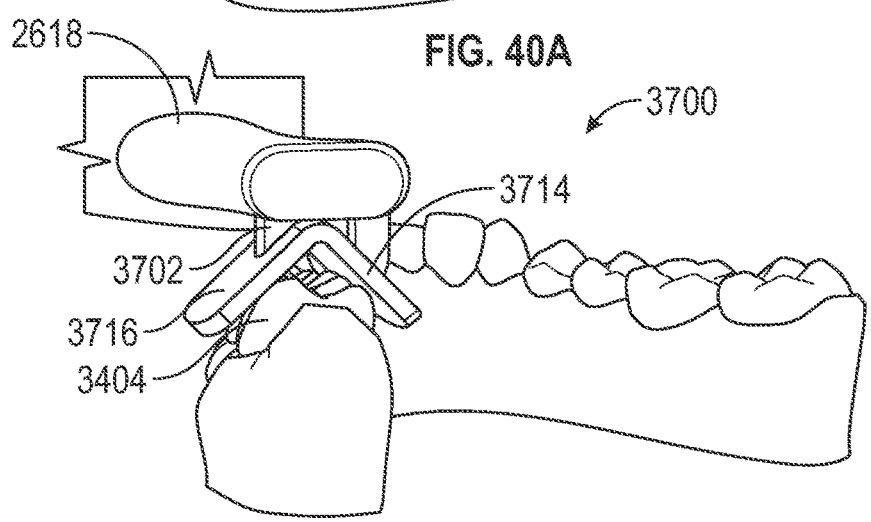

Referring to FIGS. 40A-B, an illustration of the guide 3700 of FIG. 39 moving over teeth is shown, according to some embodiments. The guide 3700 is shown moving over non-molar teeth 3402 (e.g., incisors, canines, or bicuspids) in FIG. 40A, and the first side portion 3704 and the second side portion 3706 contact the non-molar teeth 3402 when the guide 3700 is moving over the non-molar teeth 3402. The first side portion 3704 and the second side portion 3706 are sized to receive the non-molar teeth 3402 such that when receiving the non-molar teeth 3402, the non-molar teeth 3402 are substantially centered under the base 3702.

The guide 3700 is shown moving over molar teeth 3404 in FIG. 40B, the first side portion 3704 and the second side portion 3706 contact the molar teeth 3402 when the guide 3700 is moving over the molar teeth 3404. The first side portion 3704 and the second side portion 3706 are sized to receive the molar teeth 3404 such that when receiving the molar teeth 3404, the molar teeth 3402 are substantially centered under the base 3702.

Figure 41:
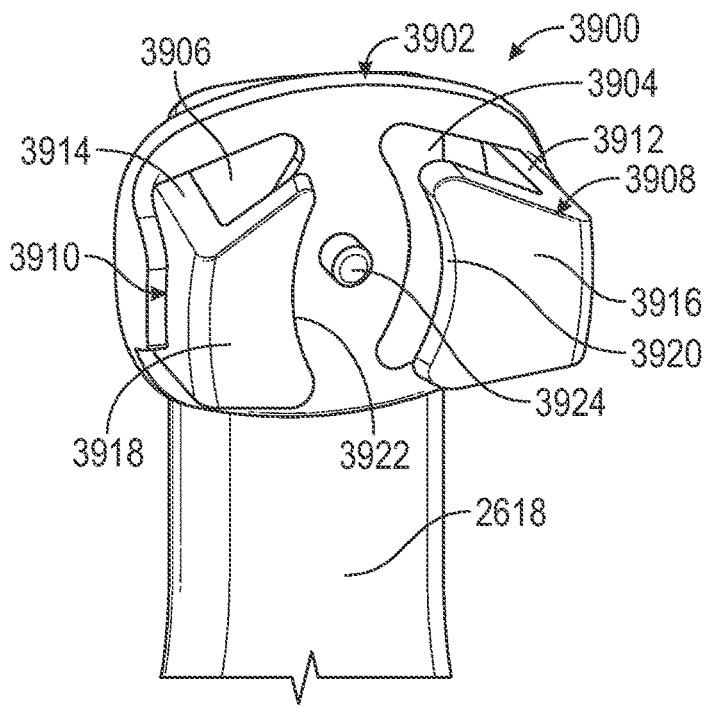
FIG. 41 is an illustration of another guide of a scanning device, according to some embodiments.

Referring to FIG. 41, an illustration of another guide 3900 of a scanning device is shown, according to some embodiments. The guide 3900 could be any of the guide 2620, the guide 2720, or the guide 2820, in various embodiments. Accordingly, reference to the stem 2618 in the description of the guide 3300 is for purposes of explanation only, and is not intended to be limiting. The guide 3900 is coupled to the stem 2618 via the coupler 2622 such that the guide 3900 can rotate relative to the stem 2618. The guide 3900 is configured to contact the teeth of a user and remain in contact with the teeth of the user during a scan of the teeth. Accordingly, the guide 3900 can be manufactured from any material suitable to contact the teeth of the user. Examples of suitable materials include, but are not limited to, various plastics (e.g., thermoplastic polyurethane, polyethylene, acrylonitrile butadiene styrene (ABS)) rubbers, and silicones.

The guide 3900 includes a base 3902, a first side portion 3904, and a second side portion 3908. The base 3902 is coupled to the coupler 2622 via a spindle 3924 that extends through the base 3902. In some embodiments, the spindle 3924 is rotatably coupled to the coupler 2622 and is rigidly coupled to the base 3902 such that the base 3902 rotates relative to the stem 2618. In some embodiments, the spindle 3924 is rigidly coupled to the coupler 2622 and is rotatably coupled to the base 3902 such that the base 3902 rotates relative to the spindle 3924 and the stem 2618. The base 3902 includes a first cavity 3904 and a second cavity 3906. The first cavity 3904 and the second cavity 3906 are openings in the base 3902 that extend entirely through the base 3902. The first cavity 3904 provides one or more surfaces to which the first side portion 3908 is coupled, and the second cavity 3906 provides one or more surfaces to which the second side portion 3910 is coupled.

The first side portion 3908 includes a first extension 3912, a first flange 3916, and a first tooth contact surface 3920. The first extension 3912 is rigidly coupled to the base 3902 and extends from the base 3902 such that the first extension 3912 is substantially perpendicular (e.g., between 80° and 100°) to the base 3902. The first flange 3916 extends from the first extension 3912 such that the first flange 3916 is substantially perpendicular (e.g., between 80° and 100°) to the first extension 3912. The first tooth contact surface 3920 is a concave surface positioned on the first flange 3916 opposite the first extension 3912. The first tooth contact surface 3920 is configured to contact one or more teeth during a scan.

The second side portion 3910 includes a second extension 3914, a second flange 3918, and a second tooth contact surface 3922. The second extension 3914 is rigidly coupled to the base 3902 and extends from the base 3902 such that the second extension 3914 is substantially perpendicular (e.g., between 80° and 100°) to the base 3902. The second flange 3918 extends from the second extension 3914 such that the second flange 3918 is substantially perpendicular (e.g., between 80° and 100°) to the second extension 3914. The second tooth contact surface 3922 is a concave surface positioned on the second flange 3918 opposite the second extension 3914. The second tooth contact surface 3922 is configured to contact one or more teeth during a scan. The first tooth contact surface 3920 and the second tooth contact surface 3922 are positioned opposite each other to contact opposite sides of one or more teeth during a scan.

Figure 42A:
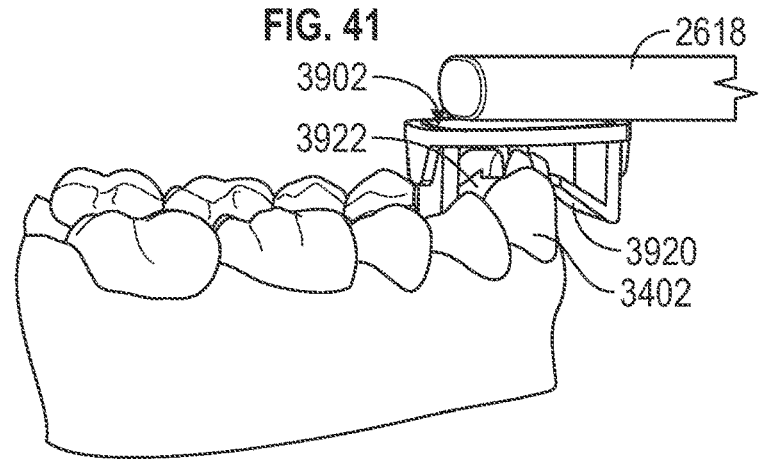
FIGS. 42A-B are illustrations of the guide of FIG. 41 moving over teeth, according to some embodiments.
Figure 42B:
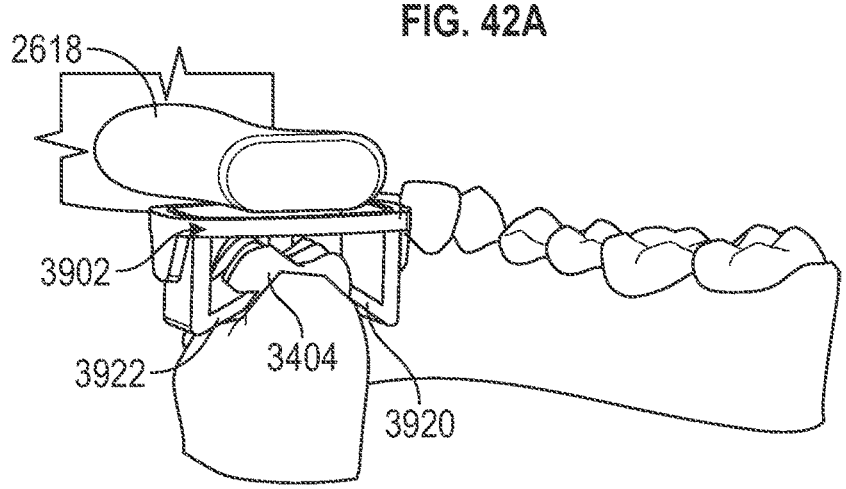

Referring to FIGS. 42A-B, an illustration of the guide 3900 of FIG. 41 moving over teeth is shown, according to some embodiments. The guide 3900 is shown moving over non-molar teeth 3402 (e.g., incisors, canines, or bicuspids) in FIG. 42A, and the first tooth contact surface 3920 and the second tooth contact surface 3922 contact the non-molar teeth 3402 when the guide 3900 is moving over the non-molar teeth 3402. As the first tooth contact surface 3920 and the second tooth contact surface 3922 contact the non-molar teeth 3402, the first extension 3912 and the second extension 3914 flex based on the size and shape of the non-molar teeth 3402. The first tooth contact surface 3920 and the second tooth contact surface 3922 are sized to receive the non-molar teeth 3402 such that when receiving the non-molar teeth 3402, the non-molar teeth 3402 are substantially centered under the base 3902.

The guide 3900 is shown moving over molar teeth 3404 in FIG. 42B, and the first tooth contact surface 3920 and the second tooth contact surface 3922 contact the molar teeth 3404 when the guide 3900 is moving over the molar teeth 3404. As the first tooth contact surface 3920 and the second tooth contact surface 3922 contact the molar teeth 3404, the first extension 3912 and the second extension 3914 flex based on the size and shape of the molar teeth 3404. The first tooth contact surface 3920 and the second tooth contact surface 3922 are sized to receive the molar teeth 3404 such that when receiving the molar teeth 3404, the molar teeth 3404 are substantially centered under the base 3902.

Figure 43:
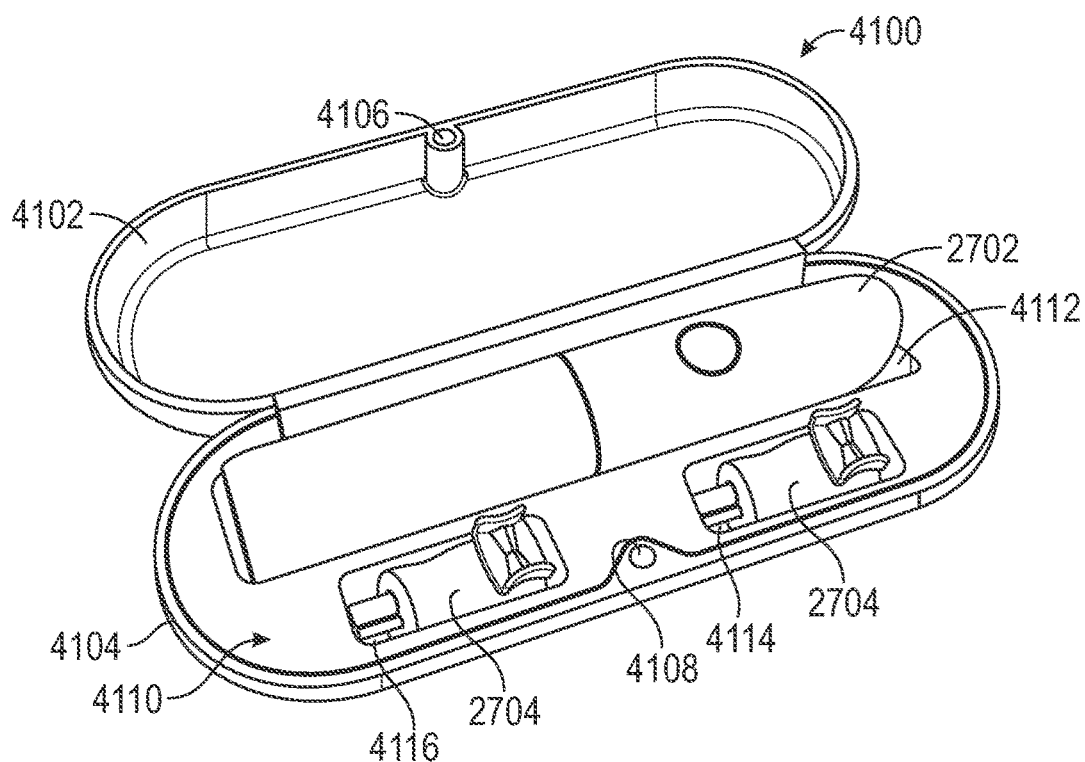
FIG. 43 is an illustration of a case for a scanning device in one configuration, according to some embodiments.

Referring to FIG. 43, an illustration of a case 4100 for a scanning device in one configuration is shown, according to some embodiments. The case 4100 is configured to store the scanning device 2700 in its component parts (e.g., the body 2702 and the guide portion 2704) such that the scanning device 2700 is protected when the scanning device 2700 is being transported by a user (e.g., when the user is traveling). The scanning device 2700 is used for exemplary purposes only. In some embodiments, the scanning device 2600, the scanning device 2800, or any other scanning device can be used. The case 4100 includes a top 4102, a bottom 4104, a top latch 4106, a bottom latch 4108, and an insert 4110.

The top 4102 and the bottom 4104 are coupled such that the top 4102 and the bottom 4104 cannot be separated, and the top 4102 and the bottom 4104 are pivotally coupled to each other. For example, the top 4102 and the bottom 4104 can be a single molded component with a living hinge that provides for pivotal movement between the top 4102 and the bottom 4104. As another example, the top 4102 and the bottom 4104 can be separate molded components coupled by a hinge that provides for pivotal movement between the top 4102 and the bottom 4104. In yet another example, the top 4102 and the bottom 4104 can be separate molded components coupled by incorporating a snap-fit connection that provides for pivotal movement between the top 4102 and the bottom 4104. The top 4102 and the bottom 4104 can be manufactured from any type of plastic that provides the desired properties to protect the scanning device 2700. For example, the top 4102 and the bottom 4104 can be manufactured from ABS, polycarbonate, polyurethane, polyethylene, or any other type of material that provides the desired properties.

The top latch 4106 is integrated with the top 4102 and is configured to mate with the bottom latch 4108 (which is integrated with the bottom 4104) to secure the case 4100 in a closed position. In some embodiments, the top latch 4106 and the bottom latch 4108 are magnets that attract each other when they are close together. For example, when closing the case 4100, the top latch 4106 and the bottom latch 4108 may force the case 4100 closed when the top latch 4106 and the bottom latch 4108 are within a threshold distance of each other (e.g., 6 mm, 8 mm, 4 mm, etc.). In some embodiments, the top latch 4104 includes a tab and the bottom latch 4106 includes a slot configured to receive the tab. In such embodiments, the user must close the case 4100 such that the top latch 4104 engages with the bottom latch 4106 to prevent the case 4100 from opening inadvertently.

The insert 4110 is configured to fit within the bottom 4104 and provide secure storage areas for various components. The insert 4110 includes a first cavity 4112, a second cavity 4114, and a third cavity 4116. The first cavity 4112 is a recessed portion of the insert 4110 and is sized to receive the body 2702 of the scanning device 2700. In various other embodiments, the first cavity 4112 is sized and configured to receive the body 2602 of the scanning device 2600, the body 2802 of the scanning device 2800, or any other body of another scanning device. The second cavity 4114 and the third cavity 4116 are sized and configured to receive various guide portions (e.g., the guide portion 2604, the guide portion 2704, the guide portion 2804, etc.) or other guides (e.g., the guide 3300, the guide 3500, the guide 3700, the guide 3900, etc.). In some embodiments, the guide portions or guides stored in the second cavity 4114 and the third cavity 4116 can be the same guide (e.g., the second cavity 4114 and the third cavity 4116 may each store a guide portion 2704). In some embodiments, the guide portions or guides stored in the second cavity 4114 and the third cavity 4116 can be different guides (e.g., the second cavity 4114 may store the guide portion 2704 and the third cavity 4116 may store the guide 3300).

In some embodiments, the case 4100 includes an electrical connection such that the case 4100 can be plugged in to a standard outlet to provide power to one or more components stored within the case 4100.

Figure 44:
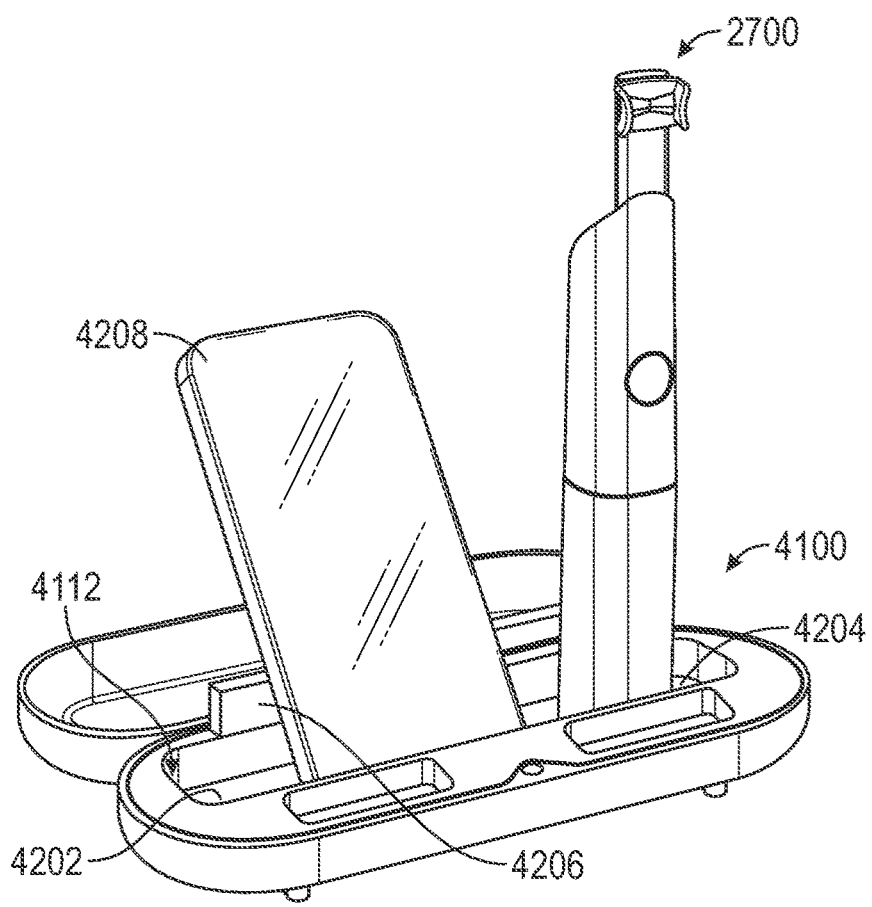
FIG. 44 is an illustration of the case of FIG. 43 in another configuration, according to some embodiments.

Referring to FIG. 44, an illustration of the case 4100 of FIG. 43 is shown in another configuration, according to some embodiments. The insert 4110 is further shown to include a mobile device cavity 4202, a scanning device cavity 4204, and a back portion 4206. The mobile device cavity 4202 and the scanning device cavity 4204 are further recessed within the first cavity 4112 such that the mobile device cavity 4202 is configured to receive a mobile device (e.g., a mobile device 4208) and the scanning device cavity is configured to receive a scanning device (e.g., the scanning device 2600, the scanning device 2700, the scanning device 2800, or any other scanning device).

The mobile device cavity 4206 is positioned such that a bottom of the mobile device 4208 can rest within the mobile device cavity such that a back of the mobile device contacts the back portion 4206 to maintain the mobile device 4208 in a substantially upright (e.g., between 45° and 90° to horizontal) position. In some embodiments, the first cavity 4112 does not include the mobile device cavity 4202, and the mobile device 4208 rests within the first cavity 4112 such that the back of the mobile device 4208 contacts the back portion 4206 to maintain the mobile device 4208 in a substantially upright position.

The scanning device cavity 4204 is sized and configured such that a base of a scanning device (e.g., the base body portion 2610, the base body portion 2710, the base body portion 2810, etc.) fits within the scanning device cavity 4204. The scanning device cavity 4204 may also include an electrical charger to mate with an electrical connection of a scanning device (e.g., the electrical connection 2614, the electrical connection 2714, the electrical connection 2814, etc.). For example, when the scanning device 2700 is secured within the scanning device cavity 4204, the electrical charger mates with the electrical connection 2714 such that the scanning device 2700 charges when the case 4100 is connected to a power source.

Figure 45:
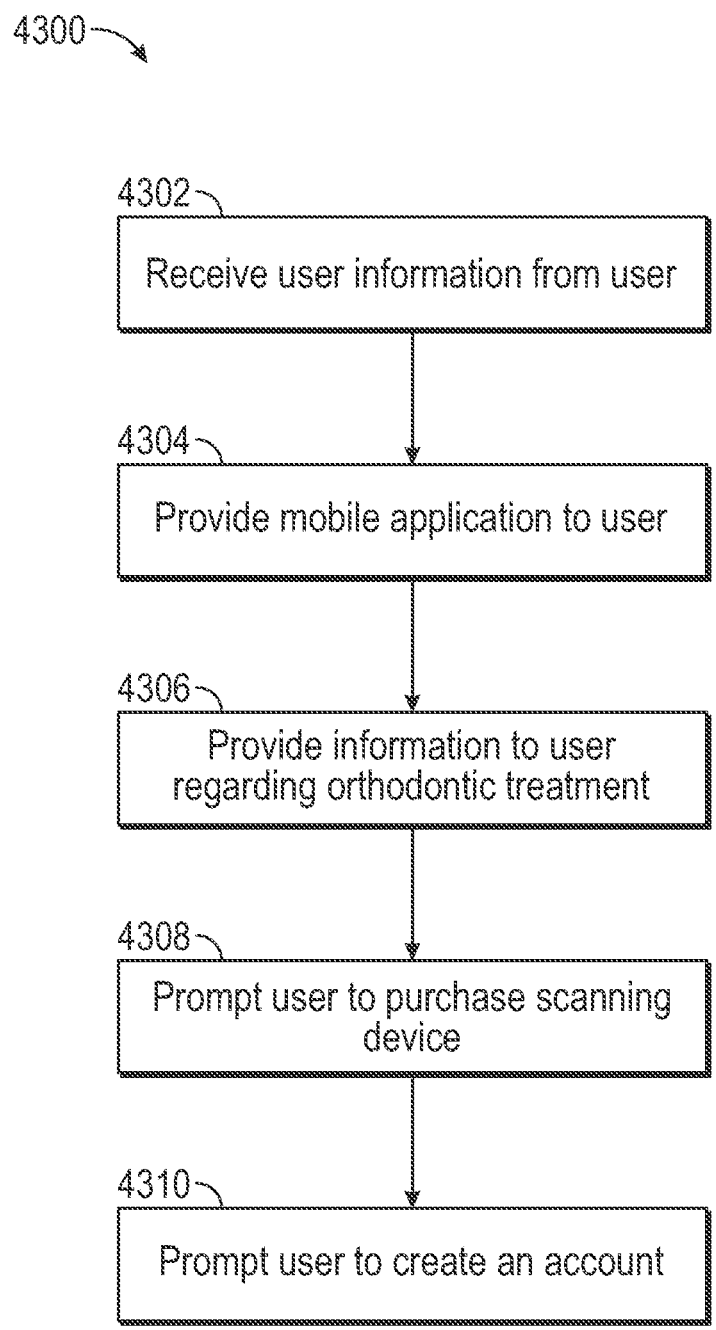
FIG. 45 is a flow diagram of a method for creating a user account, according to some embodiments.

Referring to FIG. 45, a flow diagram of a method 4300 for creating a user account is shown, according to some embodiments. At 4302, user information is received. For example, a user may desire to begin orthodontic treatment to straighten the user's teeth. The user may find an orthodontic treatment provider via an Internet search (or any other method), and may provide information to the orthodontic treatment provider (e.g., name, age, address, email address, other contact information, etc.) via the treatment provider's website.

At 4304, a mobile application is provided to the user. For example, after providing the user's email address, the treatment provider may send the user an email and prompt the user to download a mobile application for use on a mobile device (e.g., a mobile phone, a tablet computer, etc.). The mobile application may be associated with the treatment provider and may provide data to the treatment provider to develop a treatment plan. The mobile application may also provide information to the user regarding the progress of the user according to the treatment plan.

At 4306, information is provided to the user regarding orthodontic treatment. For example, after the user downloads the mobile application and opens the mobile application, the mobile application may provide the user with information regarding orthodontic treatment. The mobile application may show the user different orthodontic treatment options, including wire and bracket systems (e.g., braces) and aligner systems, and show the user how each system works. The mobile application may also show the user advantages and disadvantages of each system.

At 4308, the user is prompted to purchase a scanning device. For example, the mobile application may provide the user the option to order a scanning device to conduct a scan to begin orthodontic treatment with aligners. The user may choose to purchase the scanning device at that time, or the user may choose to defer the purchase of the scanning device to a later date. If the user chooses to purchase the scanning device at that time, the user will be prompted to enter payment information to purchase the scanner.

At 4310, the user is prompted to create an account with the treatment provider. For example, the user can create an account through the mobile application by entering additional information and creating a username and password. As another example, the user can create an account through the website of the treatment provider by entering additional information and creating a login and password.

Though the steps of method 4300 are shown in a particular order, the steps can be performed in any order. For example, the user may be provided with information regarding orthodontic treatment before the treatment provider receives information from the user and before the user is provided with the mobile application. Additionally, the user may be prompted to purchase a scanning device after creating an account or before providing the mobile application to the user. Other orders of the steps of method 4300 are also possible, and the examples above are not intended to be limiting.

Figure 46:
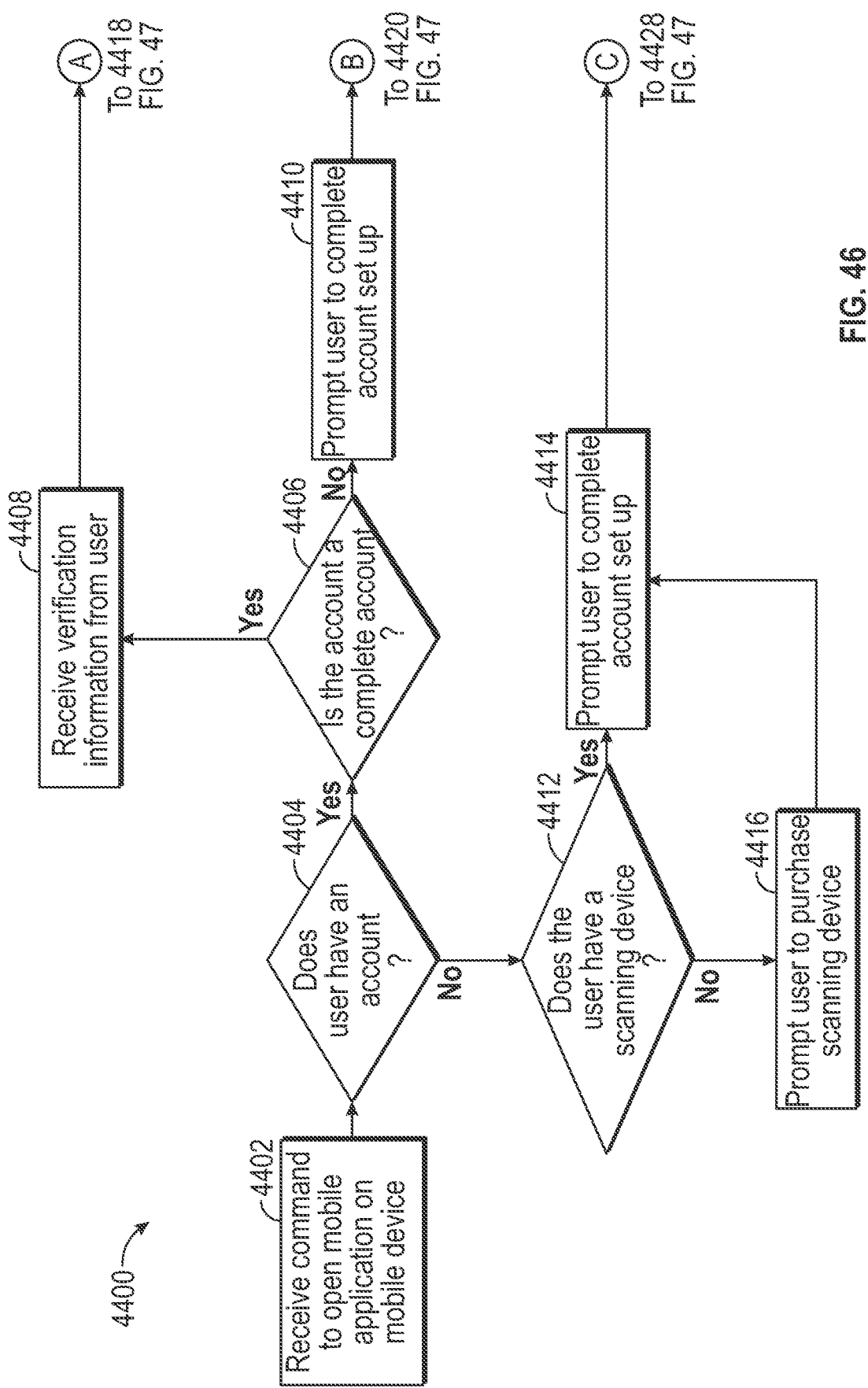
FIG. 46 is a flow diagram of a method for setting up a user account and a scanning device, according to some embodiments.
Figure 47:
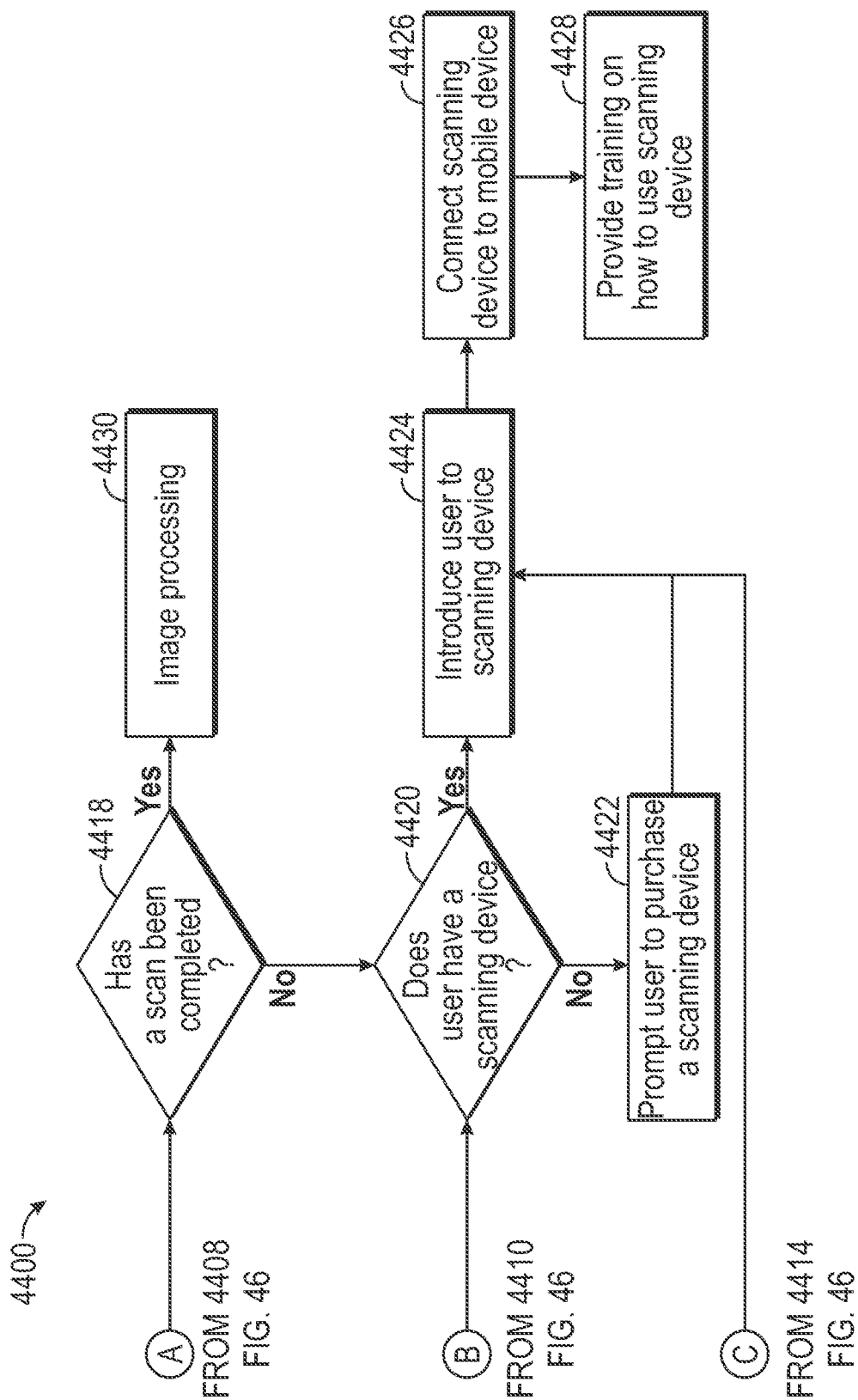
FIG. 47 is a continuation of the flow diagram of FIG. 46, according to some embodiments.

Referring to FIGS. 46-47, a flow diagram of a method 4400 for setting up a user account and a scanning device is shown, according to some embodiments. At 4402, a command is received to open the mobile application on a mobile device. For example, after downloading the mobile application, the user selects the icon for the mobile application on the mobile device, and the mobile device receives the command to open the mobile application.

At 4404, a determination is made as to whether the user has an account. If the user has an account, then at 4406 a determination is made as to whether the user account is a complete account. For example, the user may have entered the minimum amount of information when initially setting up the account, and therefore the user only has a partial account. As another example, the user may have entered all of the required information, and therefore the user has a complete account. If it is determined that the user has a complete account, at 4408 verification information is received from the user. For example, the user may enter the username and password to verify the complete account and sign in to the mobile application. As another example, the user may provide a biometric marker (e.g., a fingerprint, retina scan, facial scan, etc.) to verify the complete account and sign in to the mobile application.

At 4418, a determination is made as to whether a scan has already been completed. For example, if a scan has already been completed, the user is notified by the mobile application at 4430 that the scanned images are being processed. Image processing will be further described with reference to FIG. 50. If a scan has not already been completed, a determination is made at 4420 as to whether the user has a scanning device. For example, the mobile application may display a question to the user to ask the user if the user has a scanning device. If the user does not have a scanning device, the user is then prompted to purchase a scanning device at 4422. The user then enters information required to purchase the scanning device (payment information, shipping address, etc.) and submits the purchase to the treatment provider.

The treatment provider receives the order for the scanning device and ships the scanning device to the user. Upon shipping the scanning device, the mobile application may provide a notification to the user that the scanning device has been shipped, along with an estimated delivery date. The mobile application may also send the user a notification when the scanning device is delivered.

Returning to 4420, if the user has a scanning device (e.g., if the user previously purchased a scanning device or if the user received the scanning device after ordering the scanning device from the mobile application prompt), the user responds to the question regarding the scanning device by indicating the user has a scanning device. The user is then introduced to the scanning device at 4424. For example, the mobile application may instruct the user how to turn on the device. The mobile application may also provide the user with an overview of the scanning device by showing the user the different parts of the scanning device.

At 4426, the scanning device is connected to the mobile device. For example, the mobile application may instruct the user how to initiate pairing of the scanning device and the mobile device via Bluetooth or other short range connection mechanism. Additionally, the mobile application may instruct the user how to initiate pairing of the scanning device and the mobile device via an Internet connection (e.g., a WiFi connection or a wired Internet connection). When the scanning device and the mobile device are paired, the mobile application may provide feedback to the user to indicate that the devices are paired. The scanning device may also provide feedback (e.g., by vibration, sound, light, etc.) that it has been paired to the mobile device.

At 4428, the mobile application provides training to the user regarding how to use the scanning device. For example, the mobile application may play a video that provides a detailed overview of the scanning process. The mobile application may also provide step-by-step instructions (e.g., a combination of pictures, illustrations, and text) where the user can swipe the screen of the mobile device to move forward or backward through the steps so the user can learn each step of the operation of the scanning device. The mobile application may also provide an augmented reality training video that incorporates the user into the training video. For example, a front facing camera of the mobile device can record an image of the user as the user views the training video on the mobile device. The image of the user can be include in the training video such that the user can see how to use the scanning device relative to the user's face and/or mouth.

Returning to 4406, if the account is not a complete account, the user is prompted to complete the account at 4410 by entering additional information via the mobile application. After entering the additional information, the determination is made as to whether the user has a scanning device at 4420, as described.

Returning to 4404, if the determination is made that the user does not have an account, a determination is then made as to whether the user has a scanning device at 4412. For example, the mobile application may display a question to the user to ask the user if the user has a scanning device. If the user does not have a scanning device, the user is then prompted to purchase a scanning device at 4416. The user then enters information required to purchase the scanning device (payment information, shipping address, etc.) and submits the purchase to the treatment provider. After the user receives the scanning device, the user is prompted to complete the account set up at 4414. The user is then introduced to the scanning device at 4424, as described. If the user already has a scanning device, the user is prompted to complete the account set up at 4414, and then the user is introduced to the scanning device at 4424, as described.

Figure 48:
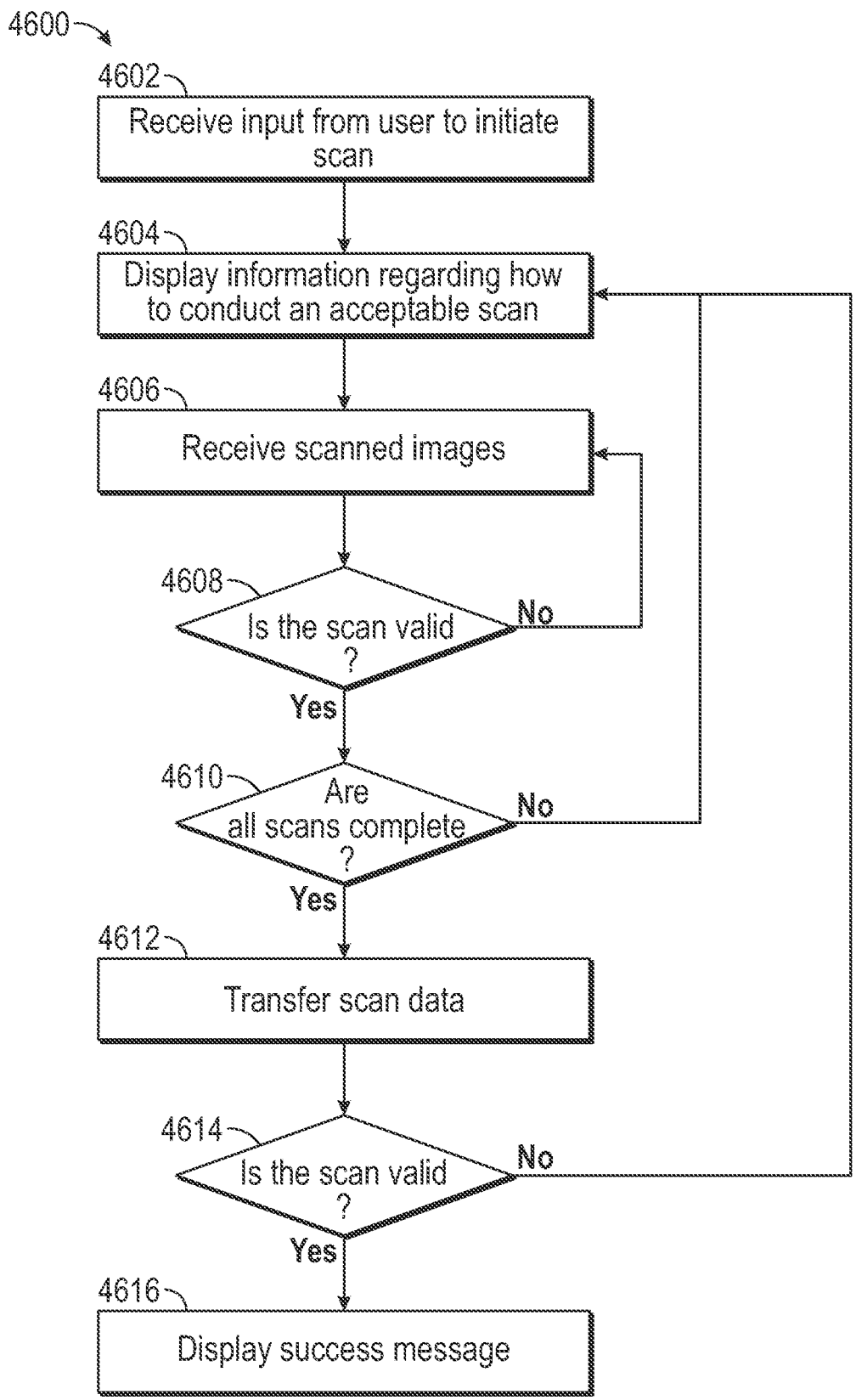
FIG. 48 is a flow diagram of a method for receiving scanned images, according to some embodiments.

Referring to FIG. 48, a flow diagram of a method 4600 for receiving scanned images is shown, according to some embodiments. At 4602, the mobile application receives input from the user to initiate a scan. For example, the home screen of the mobile application may provide the option to a user to initiate a scan by selecting an icon on the home screen (e.g., the icon may be labeled "conduct a scan," "start a scan," etc.). After selecting the icon, the scanning process is initiated by the mobile application.

At 4604, information is displayed regarding how to conduct an acceptable scan. In some embodiments, the user may be prompted to prepare a space in which the scan will be conducted. For example, the user may be prompted to clear an area in which the case 4100 can be placed, and to put the mobile device in the case such that the mobile device is visible to the user, as described with reference to FIG. 44. The user may also be prompted to perform certain preparation steps before beginning the scan. For example, the mobile application may prompt the user to brush the user's teeth, to wash the user's hands, to put gloves on the user's hands, etc. In some embodiments, a device to spread the lips of the user may be used to prevent the lips from affecting the scan. In such embodiments, the mobile application may also prompt the user to insert the device to spread the lips of the user in preparation for the scan. The mobile application may also provide the user with additional videos showing the scanning process prior to beginning the scan. In some embodiments, prior to initiating the scan, the mobile application may prompt the user to take a selfie photo to memorialize the position of the user's teeth prior to beginning the orthodontic treatment.

At 4606, the mobile application receives scanned images. For example, the user may initiate the scan by pressing a button on the scanning device. In some embodiments, the user may initiate the scan by pressing an icon on the mobile device, which communicates with the scanning device and initiates the scan. In some embodiments, the scanning device can detect its position and communicate with the mobile application when the scanning device is oriented to initiate a scan (e.g., the user holds the scanning device in a substantially horizontal position). The user proceeds to scan the user's teeth using the scanning device. For example, the user may scan the user's teeth using the scanning device 2600. The user places the guide 2620 on the lower teeth and moves the guide around the lower teeth as the scanning device scans the upper teeth. The user then places the guide 2620 on the upper teeth and moves the guide around the upper teeth as the scanning device scans the lower teeth. The images are then provided to the mobile application for further analysis.

At 4608, the mobile application determines if the scan is valid. In some embodiments, the data from the scanner is transferred from the scanning device to the mobile device via near-field communication, such as Bluetooth or WiFi. While the data is being transferred from the scanning device to the mobile device, the scanning device may provide indications that the transfer is occurring. For example, the scanning device may vibrate or flash a light (in embodiments where the scanning device is equipped with a light) to indicate the transfer is occurring. The mobile device may also provide indications that the transfer is occurring and a status of the transfer (e.g., 25%, complete, 50% complete, 75% complete). For example, the mobile application may display a message to the user that the data transfer is occurring and explain that the user may have to wait for a specified period of time before conducting an additional scan.

After the mobile application receives the data, the mobile application analyzes the images obtained by the scanning device and determines whether the data is sufficient to create a 3D model of the teeth. If the scan is not valid (e.g., the scan includes areas with missing data such that a 3D model cannot be created), the user is instructed to conduct the scan again. If the scan is valid, the mobile application determines whether all scans are complete at 4610. For example, the scanning process may include conducting a scan of the upper teeth and determining the validity of the scan prior to scanning the lower teeth, or vice versa. If the mobile application determines that not all scans are complete, the user is instructed to conduct the next scan, and may be provided with additional information regarding how to conduct an acceptable scan. If the mobile application determines that all scans are complete, the scan data is transferred to a server (e.g., the server 142) at 4612. In some embodiments, the scan data is transferred via a wired connection. In some embodiments, the scan data is transferred via a wireless connection.

At 4614, the server determines whether the scan is valid. For example, the server (e.g., the server 142) analyzes the scan data for the user's upper teeth and lower teeth and determines whether a 3D model can be created from the scan data provided. If a 3D model cannot be created, the server notifies the mobile application, and the mobile application prompts the user to rescan. For example, the server 142 may determine that not all teeth (e.g., canine, molar, cuspid, pre-molar, etc.) can be identified by the scan, thus requiring a rescan. Furthermore, the server 142 may determine that appropriate differentiation between upper teeth and lower teeth cannot be achieved (e.g., the boundaries of upper and/or lower teeth cannot be properly determined), thus requiring a rescan. Additionally, the server 142 may determine that a surface scanned by the scanner and identified as a tooth is not, in fact, a tooth, thus requiring a rescan. If a 3D model can be created, the server notifies the mobile application, and the mobile application displays a success message to the user. In some embodiments, while the server is attempting to validate the scan, the mobile application provides the user with a progress bar to indicate to the user the progress of the scan validation process. The mobile application may also prompt the user to take selfie photos of the user's teeth to provide photos of the user's teeth prior to beginning the orthodontic treatment. For example, the mobile application may prompt the user to take a selfie photo including all of the user's teeth. In some embodiments, the mobile application may prompt the user to take a photo of only the upper teeth or the lower teeth. Additionally, the mobile application may prompt the use to answer additional medical questions (e.g., medical history, dental history, etc.) during the scan validation process.

Figure 49:
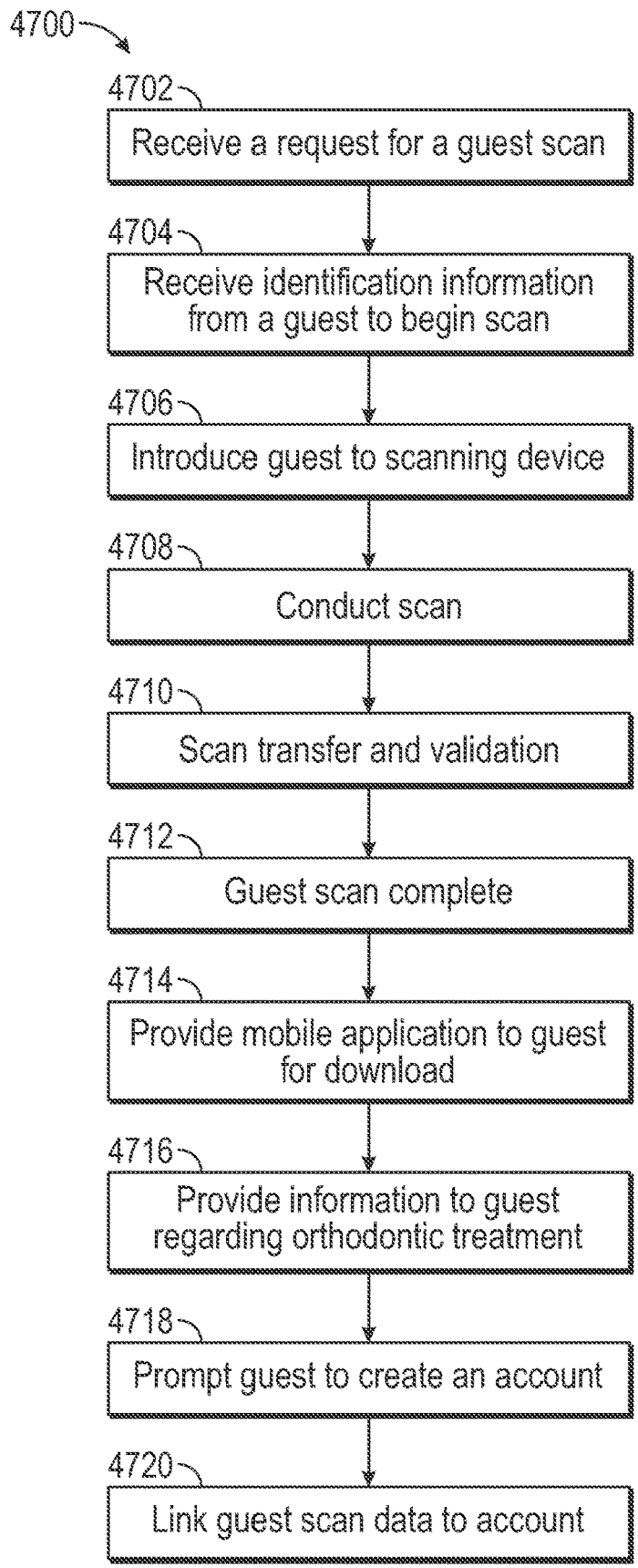
FIG. 49 is a flow diagram of a method for a guest completing a scan, according to some embodiments.

Referring to FIG. 49, a flow diagram of a method 4700 for a guest completing a scan is shown, according to some embodiments. At 4702, a request is received for a guest scan. For example, the user may desire to show a friend the scanning process, or the friend may desire to scan the friend's teeth to begin orthodontic treatment. The mobile application may provide for a guest scan on the home screen of the user's account (e.g., an icon on the home screen may be labeled "guest scan"). The user may select the option to conduct a guest scan, and a guest scan may be initiated by the mobile application.

At 4704, identification information is received from the guest. For example, the type of identification information provided by the guest may be substantially similar to the type of identification information provided by the user to create an account. For example, the guest may be prompted to provide the guest's name, address, phone number, email address, etc.

At 4706, the guest is introduced to the scanning device. The guest may be introduced to the scanning device in substantially the same manner in which the user was introduced to the scanning device in step 4424 of FIG. 47.

At 4708, a scan is conducted. For example, the guest may conduct the scan in a substantially similar manner as the user conducted the scan in FIG. 48.

At 4710, the scan is transferred and validated. For example, the guest scan may be transferred and validated in a substantially similar manner as steps 4606-4614 of FIG. 48.

At 4712, the guest scan is complete. For example, the mobile application may provide a message to the guest stating that the guest scan is complete.

At 4714, the mobile application is provided to the guest for the guest to download. For example, after the guest scan is complete, the mobile application may send a communication to the guest (e.g., an email to the guest's email account, a text to the user's mobile phone, etc.) prompting the guest to download the application on the guest's device.

At 4716, information is provided to the guest regarding orthodontic treatment. For example, the mobile application may provide the guest information regarding different orthodontic treatment options, including wire and bracket systems (e.g., braces) and aligner systems, and show the user how each system works. The mobile application may also show the user advantages and disadvantages of each system.

At 4718, the guest may be prompted to create an account. For example, the mobile application on the user's mobile device may prompt the guest to create an account such that the login process on the guest's mobile device is faster for the guest when the guest downloads the mobile application. The account created by the guest may be substantially similar to the complete account described in step 4410 of FIG. 46.

At 4720, the guest's data is linked to the guest account. For example, when the guest downloads the mobile application on the guest's mobile device and logs in to the mobile application using the login credentials created on the user's mobile device, the mobile application may determine that the user's scan data is linked to the user's mobile device and not the guest's mobile device. The mobile application may then prompt the guest to link the guest's scan data to the guest's mobile device, thereby eliminating the link between the guest's scan data and the user's mobile device.

Figure 50:
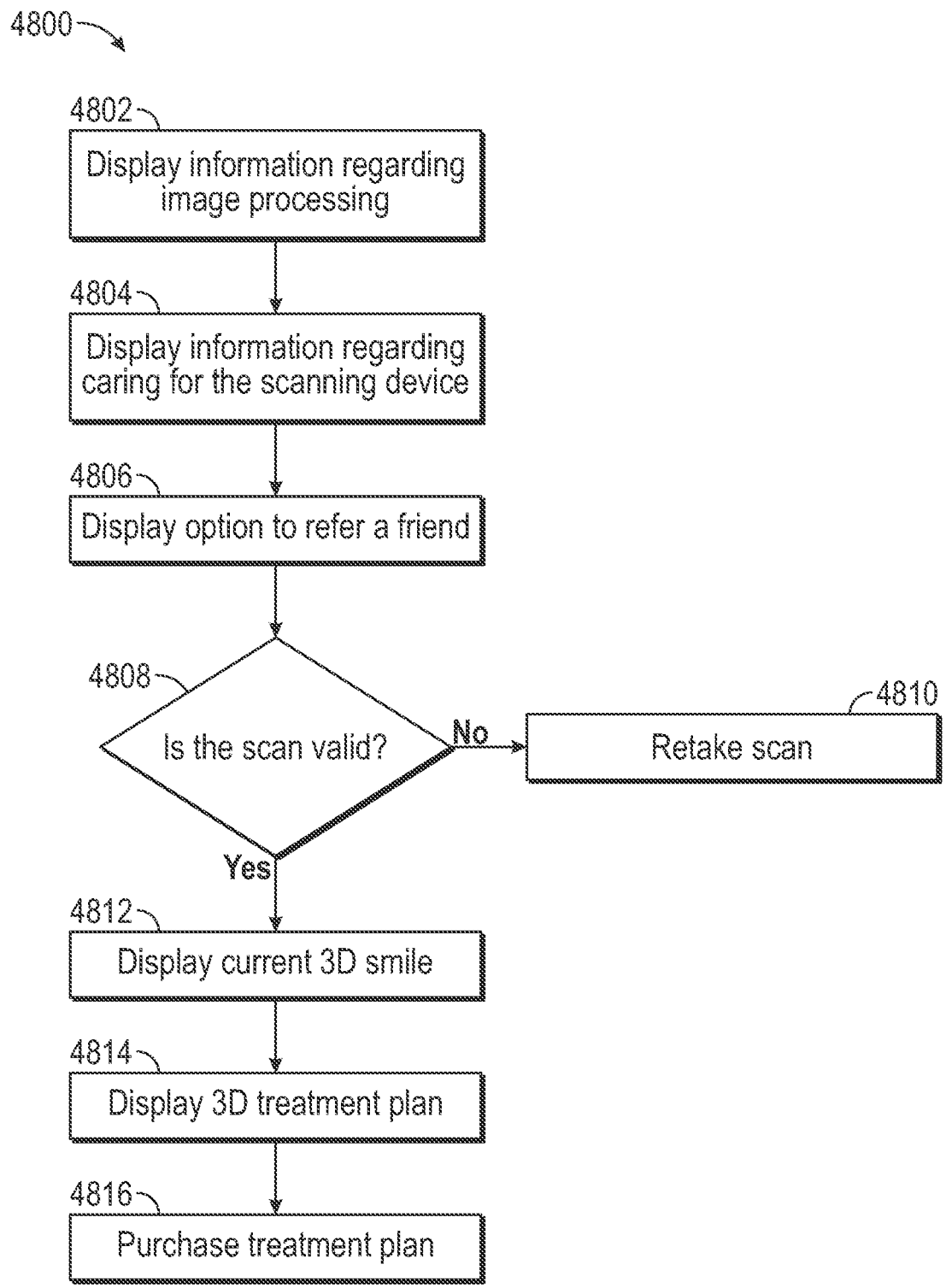
FIG. 50 is a flow diagram of a method for generating an orthodontic treatment plan, according to some embodiments.
Figure 51A:
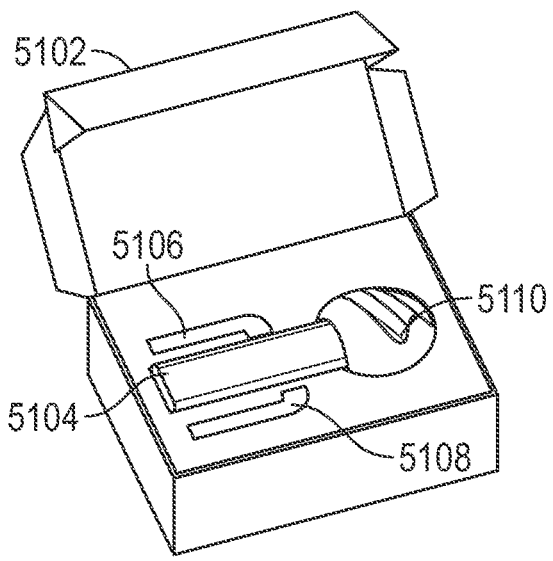
FIGS. 51A-D are illustrations of various configurations for storing and using a scanning device, according to some embodiments.
Figure 51B:
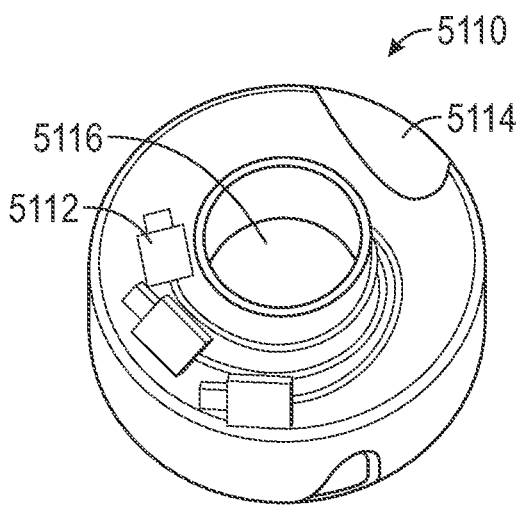
Figure 51C:
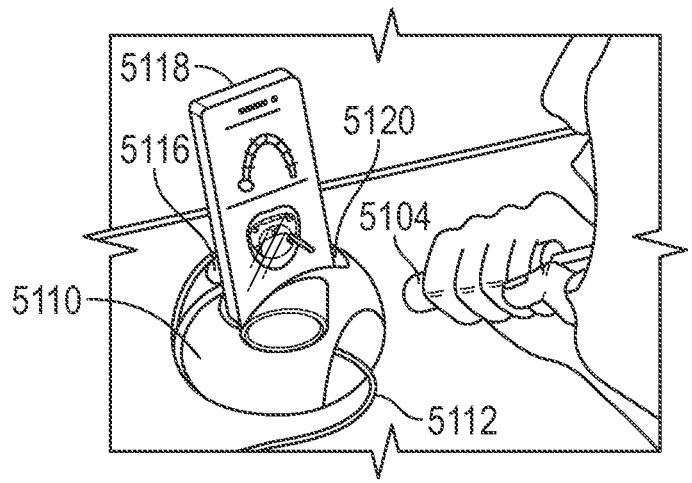
Figure 51D:
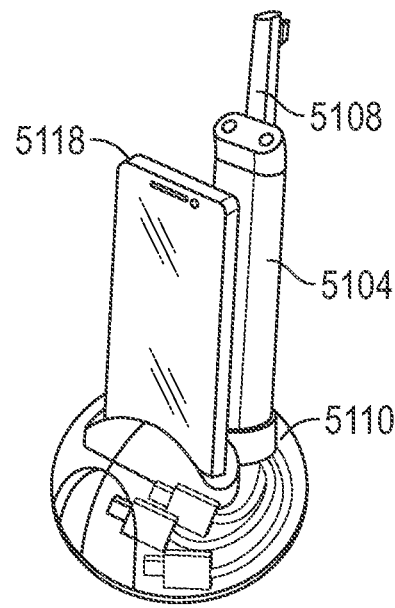
Figure 52A:
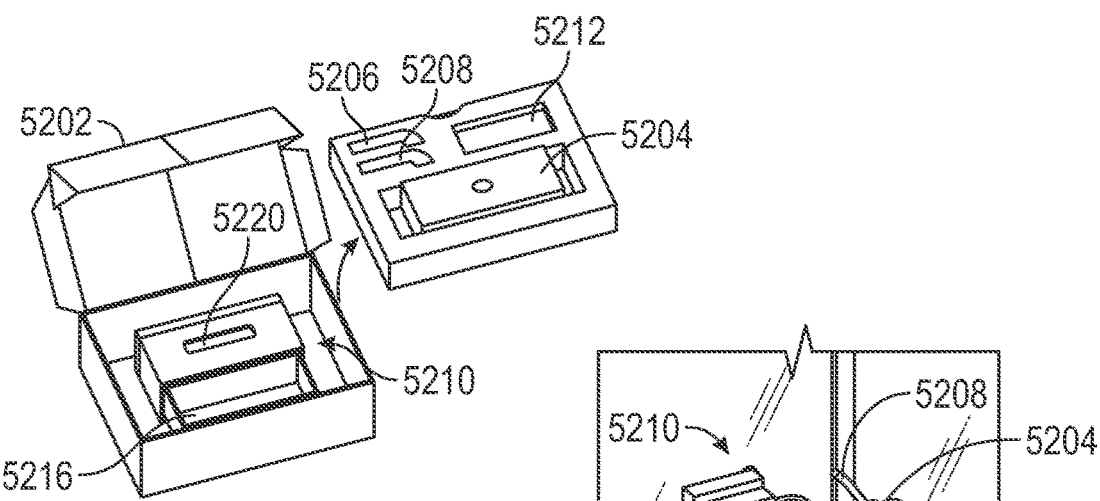
FIGS. 52A-D are illustrations of additional configurations for storing and using a scanning device, according to some embodiments.
Figure 52B:
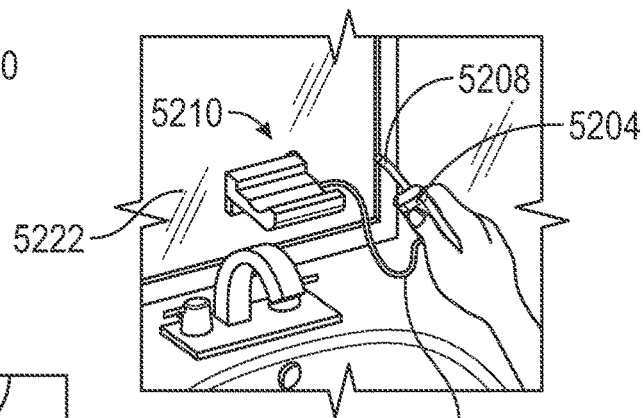
Figure 52C:
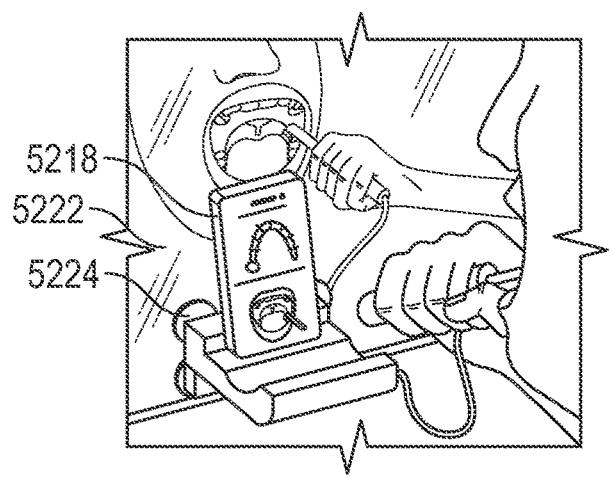
Figure 52D:
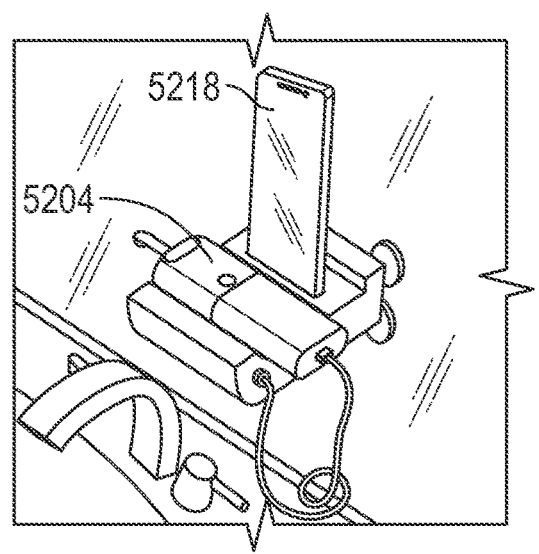
Figure 53A:
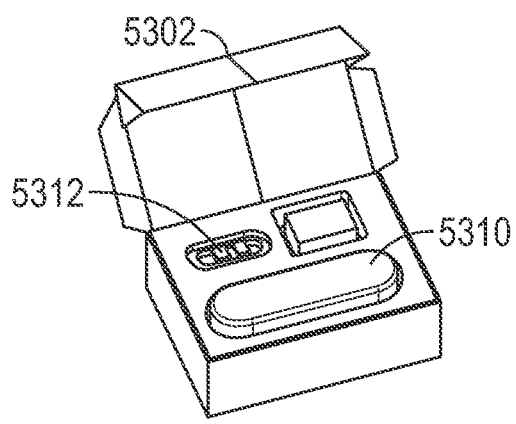
FIGS. 53A-D are illustrations of further configurations for storing and using a scanning device, according to some embodiments.
Figure 53B:
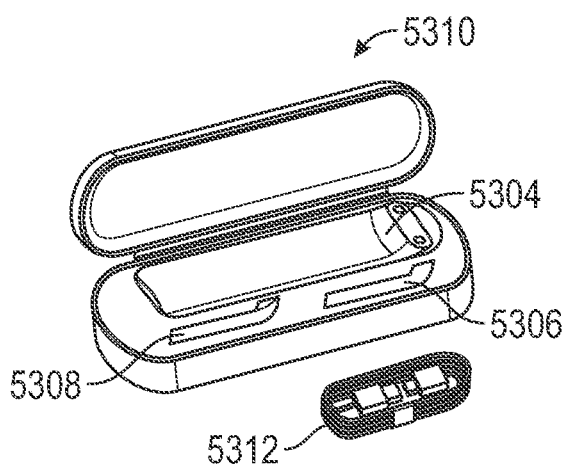
Figure 53C:
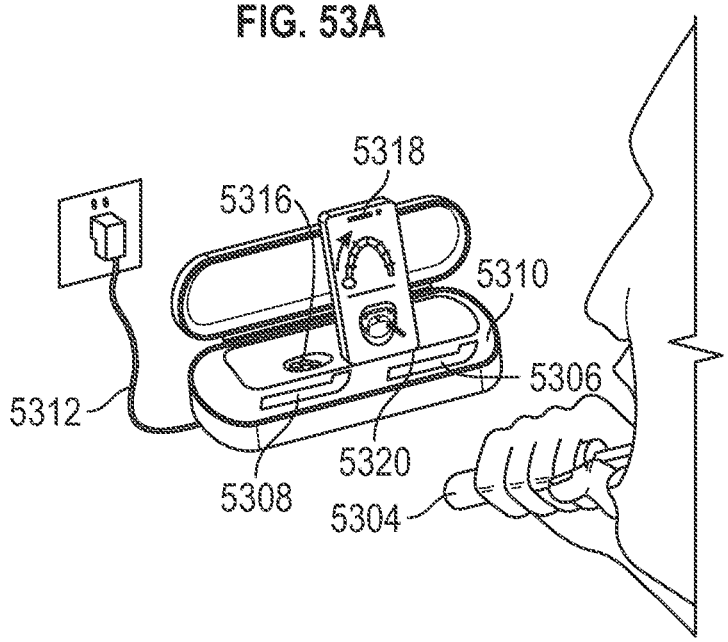
Figure 53D:
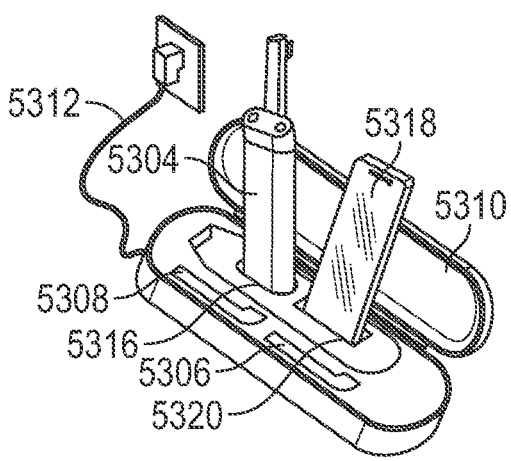

Referring to FIG. 50, a flow diagram of a method 4800 for generating an orthodontic treatment plan is shown, according to some embodiments. At 4802, information is displayed to the user regarding image processing. For example, after the user has completed the scans and the scans have been validated, the mobile application may provide the user with a message regarding what to expect while the scanned images are processing (e.g., while the images are being further validated and then converted to 3D images or models). For example, the mobile application may provide a message to the user regarding the amount of time the image processing step will take (e.g., 5 minutes, 10 minutes, 15 minutes, etc.). The mobile application may also provide the user with videos showing what happens when the user receives the orthodontic treatment kit (e.g., the orthodontic aligners). For example, the videos may show the orthodontic treatment kit arriving in the mail, the kit being unboxed, and the user inserting one or more aligners according to a treatment plan. In some embodiments, the mobile application may prompt the user to enter payment information to complete the transaction for the orthodontic treatment.

At 4804, information regarding scanner care is provided. For example, the mobile application may provide information to the user regarding how to clean the scanning device and any guides that were used during the scan. Information may be provided to the user regarding how to store the scanning device and guides to prevent damage.

At 4806, the mobile application provides an option to refer a friend. For example, during the image processing step, the mobile application may prompt the user to enter contact information for one or more friends the user wants to refer for treatment. After the user enters the contact information for the one or more friends, information is sent from the treatment provider to the one or more friends regarding the treatment, and a link to download the mobile application is provided. If the friends determine that they desire orthodontic treatment and download the mobile application, the friends will be directed to purchase a scanner and conduct a scan, as described.

At 4808, a determination is made whether the scan is valid. For example, after the server attempts to create a 3D model from the scanned images, the server will determine whether the scanned images are usable or unusable for that purpose. If the server determines that a 3D model cannot be created from the scanned images, the mobile application will prompt the user to retake the scans at 4810. If the server determines that a 3D model can be created from the scanned images, the mobile device may display a confirmation message to the user to notify the user that the images were acceptable and a 3D model was created.

At 4812, the user's current 3D smile is displayed. For example, the mobile application may display a message to the user that the user's scan is ready to be viewed, and provide the user with a button to push to view the scan. After pressing the button, the user's scan will be displayed on the mobile device. In some embodiments, the user's scan is shown as a 3D model of the current configuration of the user's teeth. The user may be able to manipulate the 3D model (e.g., zoom, pan, rotate) to view the 3D model from various orientations.

At 4814, the user's treatment plan is displayed. For example, the mobile application may display a message to the user that the user's treatment plan is ready to be viewed, and provide the user with a button to push to view the treatment plan. After pressing the button, the user's treatment plan will be displayed on the mobile device. In some embodiments, the user's treatment plan will be shown as a progression of 3D models of the user's teeth throughout the treatment plan. The user may be able to select any of the individual 3D models to provide a larger image of the 3D model, which the user may be able to manipulate (e.g., pan, zoom, rotate) to view the 3D model from various orientations. For example, the user may desire to view the 3D model of the final step in the treatment plan, which represents the final tooth configuration for the user after treatment. The user can select the final 3D model by selecting the model on the mobile device, and a larger image of the final 3D model will be displayed on the screen of the mobile device. The user can then manipulate the 3D model to view the final configuration of the user's teeth from various angles and orientations.

At 4816, the user is prompted to purchase the treatment plan. For example, if the user has not already purchased the plan at a different point in the process, the mobile application will prompt the user to enter payment information to purchase the treatment plan. After entering the payment information, the user's scan data is sent to the aligner fabrication center 162 such that the user's aligners can be manufactured and sent to the user to begin the orthodontic treatment.

Referring to FIGS. 51A-D, illustrations of a user experience are shown, according to some embodiments. After the user orders a scanning device via the mobile application, the user receives the scanning device in the mail. The scanning device arrives in packaging 5102, and the user opens the packaging 5102 to reveal the scanning device 5104, a first first guide 5106, a second guide 5108, and a base 5110. The base 5110 includes charging equipment 5112 (e.g., charging cords, plugs, etc.) such that the base 5110 can be plugged in and provide power to charge the scanning device 5104 and a mobile device 5118. The base 5110 also includes an opening 5114 through which the charging equipment 5112 can extend. The base 5110 also includes a recess 5116 sized and configured to receive the scanning device 5104. The recess 5116 includes an electrical connection that is electrically coupled with the charging equipment 5112 and is configured to mate with an electrical connector on the scanning device 5104 such that the scanning device 5104 can be charged when it is in the recess 5116. The base 5110 also includes a slot 5120 sized and configured to receive the mobile device 5118. The slot 5120 may also include an electrical connection that is electrically coupled with the charging equipment 5112 and is configured to mate with an electrical connector on the mobile device 5118 such that the mobile device 5118 can be charged when it is in the slot 5120.

To use the scanning device 5104, the user removes the components from the packaging 5102 and plugs the base 5110 into a power source. The user assembles the scanning device 5104 with the first guide 5106 or the second guide 5108 and places the mobile device 5118 in the slot 5120. The slot 5120 is positioned such that the display of the mobile device 5118 can be viewed when the user is scanning the user's teeth, as shown. As the user scans the user's teeth, the user follows along on the display of the mobile device 5118 to create an accurate scan. After the scan is complete, the user stores the charging equipment 5112 inside the opening 5114 and places the scanning device 5104 in the recess 5116. The user may also leave the mobile device 5118 in the slot 5120 if the user chooses.

Referring to FIGS. 52A-D, illustrations of another user experience are shown, according to some embodiments. After the user orders a scanning device via the mobile application, the user receives the scanning device in the mail. The scanning device arrives in packaging 5202, and the user opens the packaging 5202 to reveal the scanning device 5204, a first guide 5206, a second guide 5208, and a base 5210. The base 5210 includes charging equipment 5212 (e.g., charging cords, plugs, etc.) such that the base 5210 can be plugged in and provide power to charge the scanning device 5204 and a mobile device 5218. The charging equipment 5212 may also be used to charge the base 5210 (e.g., the base 5210 may include a rechargeable battery) such that the base 5210 can charge the mobile device 5218 and the scanning device 5204 without being plugged in to a power source. The base 5110 also includes a recess 5116 sized and configured to receive the scanning device 5104. The base 5110 also includes a slot 5120 sized and configured to receive the mobile device 5118. The slot 5120 may also include an electrical connection that is electrically coupled with the charging equipment 5112 and is configured to mate with an electrical connector on the mobile device 5118 such that the mobile device 5118 can be charged when it is in the slot 5120.

To use the scanning device 5204, the user removes the components from the packaging 5202 and plugs the base 5210 into a power source to charge the base 5210. After the base 5210 is charged, the base 5210 can be coupled to a smooth surface 5222 (e.g., a wall, a mirror, a countertop) using securement devices 5224 (e.g., suction cups, adhesive strips, etc.). The user assembles the scanning device 5204 with the first guide 5206 or the second guide 5208 and places the mobile device 5218 in the slot 5220. The slot 5120 is positioned such that the display of the mobile device 5218 can be viewed when the user is scanning the user's teeth, as shown. As the user scans the user's teeth, the user follows along on the display of the mobile device 5218 to create an accurate scan. The user can also view the positioning of the scanning device 5104 and the first guide 5206 in the smooth surface 5222 during the scan. After the scan is complete, the user stores the charging equipment 5212 inside the opening 5214 and places the scanning device 5204 in the recess 5216. The user may also leave the mobile device 5218 in the slot 5220 if the user chooses.

Referring to FIGS. 53A-D, illustrations of yet another user experience are shown, according to some embodiments. After the user orders a scanning device via the mobile application, the user receives the scanning device in the mail. The scanning device arrives in packaging 5302, and the user opens the packaging 5302 to reveal a base 5310 and charging equipment 5312. The base 5310 includes the scanning device 5304, a first guide 5306, a second guide 5308, and the charging equipment 5312 can include charging cords, plugs, or other such charging equipment such that the base 5110 can be plugged in and provide power to charge the scanning device 5304 and a mobile device 5318. The base 5310 also includes a recess 5316 sized and configured to receive the scanning device 5304. The recess 5316 includes an electrical connection that is electrically coupled with the charging equipment 5312 and is configured to mate with an electrical connector on the scanning device 5304 such that the scanning device 5304 can be charged when it is in the recess 5316. The base 5310 also includes a slot 5320 sized and configured to receive the mobile device 5318. The slot 5320 may also include an electrical connection that is electrically coupled with the charging equipment 5312 and is configured to mate with an electrical connector on the mobile device 5318 such that the mobile device 5318 can be charged when it is in the slot 5320.

To use the scanning device 5304, the user removes the components from the packaging 5302 and plugs the base 5310 into a power source. The user assembles the scanning device 5304 with the first guide 5306 or the second guide 5308 and places the mobile device 5318 in the slot 5320. The slot 5320 is positioned such that the display of the mobile device 5318 can be viewed when the user is scanning the user's teeth, as shown. As the user scans the user's teeth, the user follows along on the display of the mobile device 5318 to create an accurate scan. After the scan is complete, the user stores the charging equipment 5312 inside the opening 5314 and places the scanning device 5304 in the recess 5316. The user may also leave the mobile device 5318 in the slot 5320 if the user chooses.

Figure 54:
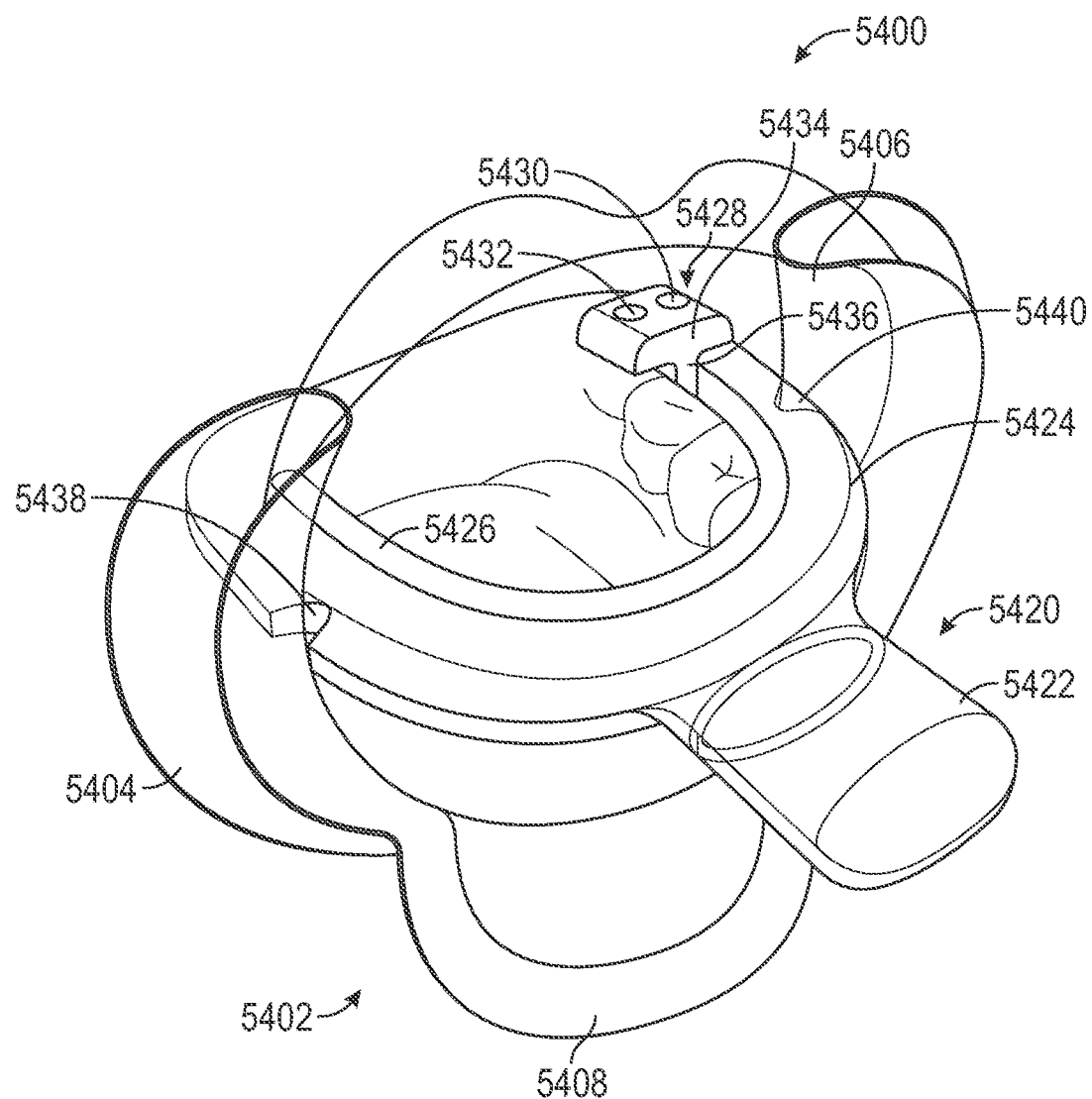
FIG. 54 is an illustration of another scanning device for scanning teeth, according to some embodiments.

Referring to FIG. 54, an illustration of another scanning device 5400 for scanning teeth is shown, according to some embodiments. The scanning device 5400 is configured to provide guidance and stability for the user during the scan to generate reliable results. The scanning device 5400 includes an insert 5402 and a scanning device 5420. The insert 5402 is configured to engage with the lips of a user and spread the lips of the user apart to facilitate a scan of the user's teeth. The insert 5402 includes a center portion 5408, a first engagement portion 5404, and a second engagement portion 5406. The insert 5402 may be manufactured from a plastic material that provides for the insert 5402 to undergo some amount of elastic deformation and then return to its original position. Examples of plastic materials include, but are not limited to, ABS, polycarbonate, and polyethylene. The first engagement portion 5404 extends from the center portion 5408 in one direction, and the second engagement portion 5406 extends from the center portion 5408 in a direction opposite the direction of the first engagement portion 5404. To place the insert 5402 in the user's mouth, the user may force the first engagement portion 5404 and the second engagement portion 5406 towards each other to reduce the space between the first engagement portion 5404 and the second engagement portion 5406. The user then places the insert 5402 in the user's mouth such that the first engagement portion 5404 engages a portion of the top lip and the bottom lip of the user on one side of the user's mouth. The user also places the insert 5402 in the user's mouth such that the second engagement portion 5406 engages a portion of the top lip and the bottom lip of the user on the other side of the user's mouth. When the user releases the force on the insert 5402, the first engagement portion 5402 and the second engagement portion 5406 move away from each other, thereby spreading the user's lips to provide greater access for the scanning device 5420.

The scanning device 5420 includes a handle 5422, an extension 5424, a track 5426, a first cutout 5438, a second cutout 5440, and a scanner 5428. The scanning device 5420 may be manufactured from any material suitable to facilitate scanning of the user's teeth. Suitable materials may include, but are not limited to, metals, plastics, and composites. The handle 5422 is coupled to the extension 5424 and is configured to provide a surface for the user to grasp when inserting the scanning device 5420 into the user's mouth. The extension 5424 provides a surface that can be positioned over the teeth of the user such that the scanner 5428 can scan the teeth. The track 5426 is coupled to the extension 5424 and is configured to receive the scanner 5428 and provide a space along which the scanner 5428 can travel during a scan. The first cutout 5438 is a space positioned along the extension 5424 that is configured to engage with the first engagement portion 5404 to secure the scanning device 5420 in place. The second cutout 5440 is a space positioned along the extension 5424 that is configured to engage with the second engagement portion 5406 to secure the scanning device 5420 in place.

The scanner 5428 includes a first camera 5430, a second camera 5432, a top 5434, and a base 5436. The scanner 5428 may also include a projector (not shown), a power source (not shown), and a motor (not shown). The first camera 5430 and the second camera 5432 may be substantially similar to the first camera 206 and the second camera 208, and they may communicate with the projector to scan the teeth of the user accurately. The first camera 5430 and the second camera 5432 are positioned on the top 5434 such that, as shown, the scanning device 5420 can scan the upper teeth of the user. The top 5434 is coupled to the base 5436, and the base is configured to be received by the track 5426. The base may include protrusions that are configured to engage with slots located along the track 5426. When the motor of the scanner 5428 is activated, the protrusions may rotate in one direction to propel the scanner 5428 along the track 5426 from one end of the track 5426 to the other end of the track 5426.

To scan the user's teeth using the scanning device 5400, the user places the insert 5402 in the user's mouth and then couples the scanning device 5420 to the insert 5402. The user may then engage with the mobile application to begin the scan, and the mobile application may send a signal to the scanner 5428 to begin the scan. The scanner 5428 will move along the track at a predetermined rate to scan the top teeth of the user. When the scan of the top teeth is complete, the mobile application may instruct the user to remove the scanning device 5420, rotate it such that the scanner is facing the user's bottom teeth, and couple the scanning device 5420 to the insert 5402 in that orientation. The mobile device may send another signal to the scanner 5428 to begin the scan, and the scanner will move along the track at the predetermined rate to scan the bottom teeth of the user. The scans are then provided to the mobile device and the server for further processing, as described with respect to the other embodiments of the device 5420 disclosed herein.

The scanning devices described herein (e.g., the scanning devices 102, 2600, 2700, 2800, 2920, 2950) are sized to be held and easily transported by the user. For example, the scanning devices described herein are approximately the same size as an electric toothbrush. In some embodiments, the scanning devices described herein are between approximately five inches and twelve inches long. In some embodiments, the scanning devices described herein are between approximately six inches and ten inches long. In some embodiments, the scanning devices described herein weigh between 0.25 pounds and three pounds. In some embodiments, the scanning devices described herein weight between one pound and two pounds.

Furthermore, the scanning devices described herein are configured to conduct a scan without being tethered to additional large equipment (e.g., equipment that requires a cart or other transportation device to move the equipment). In some embodiments, the scanning devices described herein are configured to conduct a scan without a wired tether to any other systems or devices, and can conduct a scan while being wirelessly coupled to other components of the scanning system (e.g., a mobile device). In some embodiments, the scanning devices described herein are configured to conduct a scan while being tethered to a mobile device with a wire.

Additionally, the scanning devices described herein provide an efficient, inexpensive way to conduct a scan of teeth. A scanning operation conducted with the scanning devices described herein can be executed by a user that is not a dental or orthodontic professional. The data generated by the scanning devices described herein can be provided to various entities (e.g., dental or orthodontic professionals, manufacturing facilities for manufacturing orthodontic aligners, etc.) for a variety of purposes (e.g., dental diagnosis and/or treatment and/or checkups, orthodontic treatment planning or mid-course correction, orthodontic aligner manufacturing, orthodontic checkups, etc.).

It is important to note that the construction and arrangement of the systems, apparatuses, and methods shown in the various exemplary embodiments is illustrative only. Additionally, any element disclosed in one embodiment may be incorporated or utilized with any other embodiment disclosed herein. For example, any of the exemplary embodiments described in this application can be incorporated with any of the other exemplary embodiment described in the application. Although only one example of an element from one embodiment that can be incorporated or utilized in another embodiment has been described above, it should be appreciated that other elements of the various embodiments may be incorporated or utilized with any of the other embodiments disclosed herein.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

References herein to the positions of elements (e.g., "top," "bottom," "above," "below") are merely used to describe the orientation of various elements in the figures. It should be noted that the orientation of various elements may differ according to other exemplary embodiments, and that such variations are intended to be encompassed by the present disclosure.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

As utilized herein, the term "substantially" and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general-purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general-purpose computer, special purpose computer, or special purpose processing machines to perform a certain function or group of functions.

What is claimed is:

1. A system comprising:
   an imaging system operable by a user to image teeth of the user to acquire images of the teeth of the user, the imaging system configured to allow the user to visually monitor the teeth of the user while acquiring the images of the teeth of the user, the imaging system comprising:
   a camera configured to acquire the images;
   an orientation element configured to orient the camera with respect to the teeth of the user to facilitate acquisition of the images; and
   a server system configured to:
   receive the images acquired by the imaging system; and
   determine an oral condition of the user based on the received images.

2. The system of claim 1, wherein the orientation element is configured to interface with the teeth of the user to orient the camera with respect to the teeth of the user.

3. The system of claim 1, wherein the imaging system further comprises a communications circuit configured to communicate the images to the server system via a mobile device associated with the user, wherein the mobile device is separate from the imaging system.

4. The system of claim 3, wherein the server system is in wireless communication with the mobile device, the server system configured to receive the images from the mobile device and generate a high-resolution reconstruction of the images.

5. The system of claim 1, wherein the oral condition comprises at least one of a dental condition of the user or an orthodontic condition of the user.

6. The system of claim 1, wherein the imaging system comprises a plurality of cameras configured to acquire the images.

7. The system of claim 1, wherein a mobile device associated with the user is configured to display a user interface including an indication referring the user to a dentist or an orthodontist based on the oral condition of the user.

8. The system of claim 1, wherein at least part of the imaging system is configured to be positioned in a mouth of the user.

9. The system of claim 8, wherein the camera is configured to acquire the images while the at least part of the imaging system is positioned in the mouth of the user.

10. The system of claim 1, wherein a mobile application installed on a mobile device associated with the user is configured to allow the user to visually monitor the teeth of the user while acquiring the images of the teeth of the user.

11. The system of claim 10, wherein the mobile application is configured to determine that the images are suitable to diagnose the oral condition and to display an indication to the user indicating that the images are suitable to diagnose the oral condition.

12. The system of claim 10, wherein the mobile application is configured to determine that the images are not suitable to diagnose the oral condition and to display an indication to the user indicating that the images are not suitable to diagnose the oral condition.

13. The system of claim 10, wherein the images displayed to the user indicate a progress of the imaging.

14. The system of claim 13, wherein the mobile application is configured to display the progress of the imaging to the user by displaying a generic tooth model that is replaced with a model of the teeth of the user as the imaging of the teeth of the user progresses.

15. The system of claim 13, wherein the mobile application is configured to display the progress of the imaging to the user by displaying a generic tooth model where portions of the generic tooth model change color as the imaging of the teeth of the user progresses.

16. The system of claim 1, wherein the server system is configured to provide the oral condition to a mobile device associated with the user.

17. An imaging device comprising:
a body configured to be held by a user to acquire images of teeth of the user;
a camera configured to acquire the images;
an orientation element configured to orient the camera with respect to the teeth of the user to facilitate acquisition of the images; and
a communications circuit configured to communicate the images to a server system, the server system configured determine an oral condition of the user based on the images;
wherein the imaging device is configured to allow the user to visually monitor the teeth of the user while acquiring the images of the teeth of the user.

18. The imaging device of claim 17, wherein the oral condition comprises at least one of a dental condition of the user or an orthodontic condition of the user.

19. The imaging device of claim 17, wherein the orientation element is configured to interface with the teeth of the user to orient the camera with respect to the teeth of the user.

20. The imaging device of claim 17, wherein at least part of the imaging device is configured to be positioned in a mouth of the user.

21. The imaging device of claim 20, wherein the camera is configured to acquire the images while the at least part of the imaging device is positioned in the mouth of the user.

22. A method comprising:
providing an imaging device to a user that is operable by the user to acquire images of teeth of the user, the imaging device configured to allow the user to visually monitor the teeth of the user while acquiring the images of the teeth of the user, the imaging device comprising:
a camera configured to acquire the images of the teeth of the user;
an orientation element configured to orient the camera with respect to the teeth of the user to facilitate acquisition of the images;
communicating the images from the imaging device to a mobile device of the user;
communicating the images from the mobile device of the user to a server system;
determining an oral condition of the user based on the images communicated to the server system.

23. The method of claim 22, further comprising:
determining whether the images of the teeth of the user are suitable for determining the oral condition; and
providing feedback to the user regarding whether the images of the teeth of the user are suitable for determining the oral condition.

24. The method of claim 22, further comprising:
displaying, by the mobile device, a generic image of a tooth model; and
changing, by the mobile device, the generic image of the tooth model to a model of the teeth of the user in real time to reflect a progress of the imaging.

25. The method of claim 24, wherein an appearance of the model of the teeth of the user is changed based on whether the images of the teeth of the user are suitable for determining the oral condition.

26. The method of claim 25, wherein changing the appearance of the model of the teeth of the user comprises providing an indication of whether the images of the teeth of the user are suitable for determining the oral condition.

27. The method of claim 22, further comprising:
determining, by the imaging device or the mobile device, a confidence level associated with the images, the confidence level indicating a likelihood that the images are suitable for determining the oral condition; and
displaying, by the mobile device, the confidence level to the user as the images are acquired.

28. The method of claim 22, wherein the oral condition comprises at least one of a dental condition of the user or an orthodontic condition of the user.

29. The method of claim 22, further comprising communicating the determined oral condition to the mobile device of the user.

* * * * *